(12) United States Patent
Richard et al.

(10) Patent No.: US 11,384,346 B2
(45) Date of Patent: Jul. 12, 2022

(54) TAL EFFECTOR MEANS USEFUL FOR PARTIAL OR FULL DELETION OF DNA TANDEM REPEATS

(71) Applicant: INSTITUT PASTEUR, Paris (FR)

(72) Inventors: Guy-Franck Richard, Paris (FR); Valentine Mosbach, Paris (FR); David Viterbo, Paris (FR)

(73) Assignee: INSTITUT PASTEUR, Paris (FR)

( * ) Notice: Subject to any disclaimer, the term of this patent is extended or adjusted under 35 U.S.C. 154(b) by 342 days.

(21) Appl. No.: 16/003,789

(22) Filed: Jun. 8, 2018

(65) Prior Publication Data
US 2018/0273923 A1 Sep. 27, 2018

Related U.S. Application Data

(62) Division of application No. 15/039,393, filed as application No. PCT/EP2014/075718 on Nov. 26, 2014, now abandoned.

(30) Foreign Application Priority Data

Nov. 29, 2013 (EP) .................................... 13306644

(51) Int. Cl.
| C12N 15/00 | (2006.01) |
| C12N 9/22 | (2006.01) |
| C12N 15/62 | (2006.01) |
| C12N 15/90 | (2006.01) |
| A61K 48/00 | (2006.01) |

(52) U.S. Cl.
CPC ............... *C12N 9/22* (2013.01); *C12N 15/62* (2013.01); *C12N 15/907* (2013.01); *C12Y 301/21004* (2013.01); *A61K 48/005* (2013.01); *C07K 2319/80* (2013.01)

(58) Field of Classification Search
CPC ........ C12N 9/22; C12N 15/62; C12N 15/907; C12Y 301/21004; A61K 48/005; C07K 2319/80
See application file for complete search history.

(56) References Cited

U.S. PATENT DOCUMENTS

| 2011/0016540 A1 | 1/2011 | Weinstein |
| 2011/0301073 A1 | 12/2011 | Gregory |
| 2016/0273002 A1* | 9/2016 | Duchateau ............... A61P 25/14 |

FOREIGN PATENT DOCUMENTS

| EP | 2206723 A1 | 7/2010 |
| WO | 2013/130824 A1 | 9/2013 |
| WO | WO-2013130824 A1 * | 9/2013 | ......... C07K 14/4703 |

OTHER PUBLICATIONS

Deng et al entitled Revisiting the TALE repeat (Protein Cell 2014, vol. 5, No. 4: pp. 297-306). (Year: 2014).*
The Dissertation of Sun (2013) (Year: 2013).*
Deng et al in "Structural basis for sequence-specific recognition of DNA by TAL effectors" (Science vol. 335 Feb. 10, 2012, pp. 720-723) (Year: 2012).*
Sun & Zhao in "Transcription Activator-Like Effector Nucleases (TALENS): A highly efficient and versatile tool for genome editing" (published Apr. 7, 2013: Biotechnology & Bioengineering vol. 110, Issue 7, Jul. 2013, pp. 1811-1821) (Year: 2013).*
Score result for Duchateau & Juillerat (2013) (Year: 2013).*
Richards et al, entitled: "Highly specific contractions of a single CAG/CTG trinucleotide repeat by TALEN in yeast" PloS Apr. 18, 2014; vol. 9, No. 4: e95611). (Year: 2014).*
David Mittelman et al: "Zinc-finger directed double-strand breaks within CAG repeat tracts promote repeat instability in human cells", Proceedings of the National Academy of Sciences, National Academy of Sciences, US, vol. 106, No. 24, Jun. 16, 2009 (Jun. 16, 2009), pp. 9607-9612.
Liu Guoqi et al: "Replication-dependent 1-23 instability at (CTG)center dot(CAG) repeat hairpins in human cells", Nature Chemical Biology, Nature Pub. Group, vol. 6 , No. 9 , Aug. 1, 2010 (Aug. 1, 2010-08)-Sep. 1, 2010 (Sep. 1, 2010), pp. 652-659.
G.-F Richard et al: "Double-strand break repair can lead to high frequencies of deletions within short CAG/CTG trinucleotide repeats", Molecular and General Genetics, Jun. 1, 1999 (Jun. 1, 1999), pp. 871-882.
J. Keith Joung et al: "TALENs: a widely 1-23 applicable technology for targeted genome editing", Nature Reviews Molecular Cell Biology, vol. 14, No. 1, Nov. 21, 2012 (Nov. 21, 2012), pp. 49-55.

(Continued)

*Primary Examiner* — Catherine S Hibbert
(74) *Attorney, Agent, or Firm* — Arrigo, Lee, Guttman & Mouta-Bellum LLP

(57) ABSTRACT

The application relates to means, which derive from TAL effectors and TALENs. The structure of the means of the application is especially adapted for partial or full deletion of at least one DNA tandem repeat, more particularly for partial or full deletion of at least one DNA tandem repeat in a double-stranded DNA, more particularly for partial or full deletion of at least one DNA tandem repeat, which is contained in a double-stranded DNA and, which forms a complex secondary structure, such as a hairpin, a triple helix or a tetraplex secondary structure. The means of the application are notably useful in the treatment and/or prevention and/or palliation of a disease or disorder involving at least one DNA tandem repeat, such as DM1, SCA8, SCA12, HDL2, SBMA, HD, DRPLA, SCA1, SCA2, SCA3, SCA6, SCA7, SCA17, PSACH, DM2, SCA10, SPD1, OPMD, CCD, HPE5, HFG syndrome, BPES, EIEE1, FRAXA, FXTAS and FRAXE.

16 Claims, 8 Drawing Sheets

Specification includes a Sequence Listing.

(56) References Cited

OTHER PUBLICATIONS

Marine Beurdeley et al: "Compact designer 1-23 TALENs for efficient genome engineering", Nature Communications, vol. 4, Apr. 23, 2013 (Apr. 23, 2013), p. 1762.

M. Holkers et al: "Differential integrity 11,23 of TALE nuclease genes following adenoviral and lentiviral vector gene transfer into human cells", Nucleic Acids Research, vol. 41, No. 5, Dec. 28, 2012 (Dec. 28, 2012)-Mar. 1, 2013 (Mar. 1, 2013), pp. e63-e63.

Wanxu Huang et al: "Tandem Repeat Modification during Double-Strand Break Repair Induced by an Engineered TAL Effector Nuclease i n Zebrafish Genome", PLOS ONE, vol. 8, No. 12, Dec. 26, 2013 (Dec. 26, 2013), p. e84176.

Guy-Franck Richard et al: "Highly Specific Contractions o f a Single CAG/CTG Trinucleotide Repeat by TALEN in Yeast", PLOS ONE, vol. 9, No. 4, Apr. 18, 2014 (Apr. 18, 2014), p. e95611.

David J. Segal et al: "Genome Engineering 1-23 at the Dawn of the Golden Age", Annual Review of Genomics and Human Genetics, vol. 14, No. 1, Sep. 26, 2012.

Deng et al in "Structural basis for sequence-specific recognition of DNA by TAL effectors" (Science vol. 335 Feb. 10, 2012, pp. 720-723).

Sun & Zhao in "Transcription Activator-Like Effector Nucleases (TALENS): A highly efficient and versatile tool for genome editing" (published Apr. 7, 2013: Biotechnology & Bioengineering vol. 110, Issue 7, Jul. 2013, pp. 1811-1821 ).

\* cited by examiner

TAL EFFECTOR MEANS USEFUL FOR PARTIAL OR FULL DELETION OF DNA TANDEM REPEATS

SEQUENCE LISTING

The instant application contains a Sequence Listing which has been submitted electronically in ASCII format and is hereby incorporated by reference in its entirety. Said ASCII copy, created on Nov. 18, 2021, is named DI2011-23 B SL.txt and is 67,470 bytes in size.

FIELD OF THE INVENTION

The application relates to means, which derive from transcription activator-like (TAL) effectors, more particularly from TAL effector endonucleases (TALENs).

The means of the application are notably useful for fully or partially deleting a DNA tandem repeat, more particularly for fully or partially deleting a DNA tandem repeat in a double-stranded DNA molecule, more particularly for fully or partially deleting an expanded DNA tandem repeat in a double-stranded DNA molecule.

The application also relates to medical and biotechnological applications, more particularly in the field of diseases and disorders involving expanded DNA tandem repeats in double-stranded DNA molecules, such as trinucleotide repeat diseases or disorders, tetranucleotide repeat diseases or disorders or pentanucleotide repeat diseases or disorders.

BACKGROUND OF THE INVENTION

DNA tandem repeats occur frequently in double-stranded DNAs of eukaryotic genomes, more particularly of the human genome. DNA tandem repeat units of 2, 3, 4, 5 or even more nucleotides can be observed in a genome at different frequencies and locations (exons, introns, intergenic regions). DNA tandem repeats are prone to recombination and/or random integration events, and are considered to be at the center of species evolution.

However, expansion in the length of a DNA tandem repeat can result in deleterious effects on gene function, leading to disease or disorder. Expansion in DNA tandem repeat is known to underlie about 20 severe neurological and/or muscular and/or skeletal diseases or disorders (McMurray 2010).

Over the last 20 years or so, it was demonstrated that replication slippage, double-strand break repair, base excision repair, nucleotide excision repair, basically any mechanism involving de novo DNA synthesis within a DNA tandem repeat, are involved in DNA tandem repeat expansion. However, the precise mechanisms are still obscure.

A large amount of studies were devoted to understanding the mechanisms responsible for large trinucleotide repeat expansions, using model systems as diverse as bacteria, yeast, *drosophila*, mice or human cell lines.

Richard et al. 1999 and Richard et al. 2003 demonstrated that the insertion of a recognition site for the rare cutter endonuclease I-SceI or HO between two short $(CAG)_n$ repeats leads to the induction of a double-strand break (DSB) by said endonuclease, resulting in contractions or expansions of the repeat domain. However, the efficacy of such engineered nucleases is highly variable depending on the genomic target tested, and requires the insertion of the endonuclease recognition site.

Zinc-finger nucleases (ZFN) were developed for targeted gene editing in eukaryotes. They were built by fusing modular zinc-finger DNA-binding domains to the catalytic domain of the Fok I endonuclease (Mittelman et al. 2009). However, they induce high toxicity and a high frequency of off-target mutations, probably due to recognition and cutting of many degenerate sequences differing only slightly from the targeted sequence.

Hence, the available prior art means are not fully adapted to the deletion of an (expanded) DNA tandem repeat in a double-stranded DNA, and are not adapted to medical applications. Furthermore, an expanded DNA tandem repeat domain in a double-stranded DNA, such as those observed in pathological conditions, poses particular technical problems. Indeed, such an expanded DNA tandem repeat domain forms a complex secondary structure, such as a hairpin, a triple helix or a tetraplex secondary structure, which hinders or complicates accessibility to appropriate cleavage and which may promote repeat expansion during DSB repair (Richard et al. 2000).

Appropriate means should allow size reduction of the (expanded) DNA tandem repeat down to a non-pathological level, even when said (expanded) DNA tandem repeat has a complex secondary structure, such as a hairpin, a triple helix or a tetraplex secondary structure.

Appropriate means should also be as less toxic as possible to allow survival of the cell, and induce as less side mutations or alterations as possible. Advantageously, they should be sufficiently specific to avoid off-targets cleavage as much as possible.

The application provides means, which can achieve these goals.

SUMMARY OF THE INVENTION

The means of the application derive from TAL effectors and TALENs. The structure of the means of the application is especially adapted for partial or full deletion of at least one DNA tandem repeat, more particularly for partial or full deletion of at least one DNA tandem repeat in a double-stranded DNA, more particularly for partial or full deletion of at least one DNA tandem repeat, which is contained in a double-stranded DNA and, which forms a non-linear secondary structure, such as a hairpin, a triple helix or a tetraplex secondary structure. The means of the application are especially adapted for partial or full deletion of at least one (expanded) DNA tandem repeat in a double-stranded DNA, such as those observed in pathological conditions.

The application relates to the subject-matter as defined in the claims as filed and as herein described.

More particularly, the application relates to DNA-binding polypeptides and to products deriving therefrom such as nucleic acids, vectors, cells, liposomes, nanoparticles, sets, compositions, kits, pharmaceutical compositions, medicaments and drugs.

The application also relates to uses of said products and to methods involving at least one of said products, more particularly in the medical field.

The products of the application are notably useful in the treatment and/or prevention and/or palliation of a disease or disorder involving at least one DNA tandem repeat, more particularly of a trinucleotide, tetranucleotide or pentanucleotide disease or disorder, such as DM1, SCA8, SCA12, HDL2, SBMA, HD, DRPLA, SCA1, SCA2, SCA3, SCA6, SCA7, SCA17, PSACH, DM2, SCA10, SPD1, OPMD, CCD, HPE5, HFG syndrome, BPES, EIEE1, FRAXA, FXTAS and FRAXE (cf. Tables 6, 7 and 8 below).

The means of the application allow size reduction of the DNA tandem repeat down to a non-pathological level at a high efficacy rate (near 100% in heterozygous and homozygous yeast cells).

No increase in the mutation rate was detected. No large genomic rearrangement, such as aneuploidy, segmental duplication or translocation, was detected.

According to an advantageous aspect of the application, the means of the application do not induce any length alteration or mutation at off-target locations, e.g., in non-pathological genes, which comprise the same repeat unit as the pathological gene.

It is believed that it is the first demonstration of the induction of a shortening of a DNA tandem repeat in a double-stranded DNA to lengths below pathological thresholds in humans, with 100% efficacy and a high specificity.

BRIEF DESCRIPTION OF THE FIGURES

FIG. 1A: Plasmids pCLS9996 (C.N.C.M. deposit number I-4804; C.N.C.M. deposit date: 10 Oct. 2013) and pCLS16715 (C.N.C.M. deposit number I-4805; C.N.C.M. deposit date: 10 Oct. 2013), carrying the two TALEN arms were respectively transformed into GFY40 strain or GFY6162-3D. Haploids were crossed and diploids containing both TALEN arms were selected on SC-Leu supplemented with G418 sulfate. As a control, the split-TALEN left arm carried by pCLS9984 was transformed in GFY6162-3D, crossed to GFY40 carrying the TALEN right arm, and diploids were selected as before.

FIG. 1B: Sequences recognized by both TALE DNA-binding domains and by the split-TALE. The length of the spacer, which is appropriate to induce a DSB was deduced from repeat tract lengths analyzed in surviving cells after TALEN induction (length of 18 bp). FIG. 1B discloses SEQ ID NOS 57-60 and 61-62 as the full-length sequences, respectively, in order of appearance.

FIG. 2A: Survival after galactose induction (ratio of CFU on galactose plates over CFU on glucose plates, after 3-5 days of growth at 30° C.).

FIG. 2B: Molecular analysis of heterozygous diploids (SUP4-opa1/sup4-(CAG)).

FIG. 2C: PCR amplification of DNA extracted from survivors. When both alleles are present, bands of slightly different sizes corresponding to uncut alleles are visible in both lanes (arrow labeled "Uncut"), along with restriction products of cut alleles (arrows labeled "Cut"). When only the SUP4-opa1 allele is present, no cut product is detected in the 'I' lane (clones 8 and 11 to 20).

FIG. 2D: Molecular analysis of homozygous diploids (sup4-(CAG)/sup4-(CAG)). Same as FIG. 2B, except that total genomic DNA was digested with Ssp I.

FIG. 3A: Sanger sequencing of survivors.

FIG. 3B: Two models proposing how heterozygous and homozygous repeats may be formed following TALEN induction.

FIG. 3C: Deep sequencing of yeast genomes from yeast colonies isolated on glucose or galactose plates.

FIG. 3D: Pulse-field gel electrophoresis of red and white colonies after galactose induction.

DETAILED DESCRIPTION OF THE INVENTION

Figure 1A:
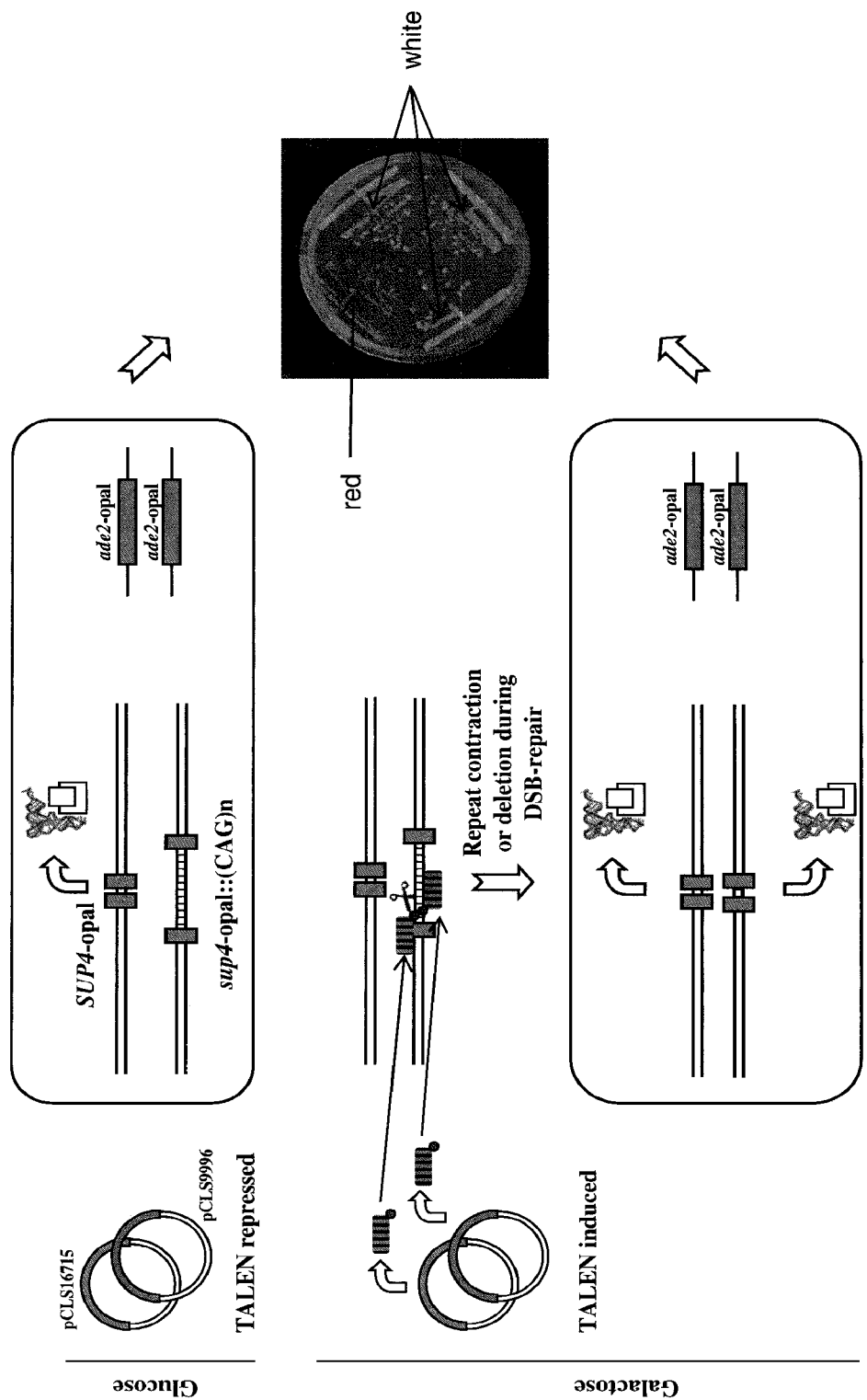
FIGS. 1A and 1B: schematic representation of the experiments of example 1.

The application relates to the subject-matter as defined in the claims as filed and as herein described.

The means of the application derive from means, which were created for genome editing, i.e., Transcription Activator-Like (TAL) effectors and TAL effector endonucleases (TALENs).

TAL effectors and TALENs have been described e.g., in Boch et al. 2009, Moscou et al. 2009, Bogdanove and Voytas 2011, Cermark et al. 2011, Bedell et al. 2012, Beurdeley et al. 2012, WO 2011/072246 (and its national counterparts, more particularly its US counterpart(s) (including the US continuation and divisional application(s))), WO 2010/079430 (and its national counterparts, more particularly its US counterpart(s) (including the US continuation and divisional application(s))).

TAL effectors have been discovered in phytopathogenic bacteria of the genus *Xanthomonas*, and are key virulence factors of these bacteria. Once inside the plant cell, they enter the nucleus, bind effector-specific DNA sequences and reprogram the host cell by mimicking eukaryotic transcription factors (Boch et al. 2009; Moscou et al. 2009). A naturally-occurring TAL effector typically comprises:

- a tandem repeat (or central domain), which is the direct tandem repeat of adjacent amino acid units, wherein each unit of the (tandem) repeat consists of 33, 34 or 35 amino acids, the N- to C-ordered series of which determine the (specific) recognition of a nucleotide sequence,
- said tandem repeat being followed (in C-term) by a truncated amino acid unit (usually, the truncation is at 20 amino acids), which is not involved in the (specific) recognition of said nucleotide sequence,
- at least one Nuclear Localization Signal (NLS), and
- an acidic transcriptional Activation Domain (AD) (cf. Boch et al. 2009).

The number of (full-length) units of the tandem repeat of a naturally-occurring TAL effector (i.e., the number of amino acid units, which determine the (specific) recognition of the nucleotide sequence) may e.g., range from 8 to 39, more particularly from 10 to 33, usually from 12 to 27.

TAL effectors are highly conserved among the different bacterial species. Examples of TAL effectors, which derive from a naturally-occurring source, include AvrBs3 (from *Xanthomonas campestris* pv. *vesicatoria*), PthXol (from *Xanthomonas oryzae* pv. *oryzae*), AvrXa27 (from *Xanthomonas oryzae* pv. *oryzae*), PthXo6 (from *Xanthomonas oryzae* pv. *oryzae*), PthXo7 (from *Xanthomonas oryzae* pv. *oryzae*).

The amino acid sequence of each (tandem) repeat unit is largely invariant within a TAL effector, with the exception of two adjacent amino acids, which are known as the Repeat Variable Diresidue (RVD), and which typically are at positions 12 and 13 within the repeat unit.

When a TAL effector repeat unit consists of 34 or 35 amino acids, the RVDs are at positions 12 and 13.

When a TAL effector repeat unit consists of 33 amino acids, the amino acid that is at the second position in the RVD is missing (i.e., the variable amino acid, which would have been at position 13, is missing). Hence, in such a situation, the RVD does not consist of two adjacent amino acids, but of only one amino acid. In accordance with the acknowledged terminology in the field of TAL effectors and TALENs, said amino acid at position 12 is being referred to as a RVD, although it is not followed by a variable amino acid at position 13.

Repeat units with different RVDs recognize different nucleotides, and there is a direct correspondence between the RVDs in the repeat domain and the nucleotides in the target DNA sequence. Examples of RVDs and of their corresponding target nucleotides are given in Table 5 below.

TABLE 5

| RVD | nucleotide |
| --- | --- |
| HD | C |
| NG | T |
| NI | A |
| NN | G or A |
| NS | A or C or G |
| N* | C or T |
| HG | T |
| H* | T |
| IG | T |
| HA | C |
| ND | C |
| NK | G |
| HI | C |
| HN | G |
| NA | G |
| SN | G or A |
| YG | T |

*denotes a gap in the repeat sequence corresponding to a lack of the amino acid residue at the second position of the RVD (e.g., when the repeat consists of 33 amino acid, instead of 34 or 35 amino acids).

In accordance with the acknowledged terminology in the field of TAL effector and TALEN, each of the amino acid units that forms the tandem repeat of a TAL effector or TALEN (i.e., each of the amino acid units, which determine the (specific) recognition of the nucleotide sequence) is being referred to as a (tandem) repeat unit, although the repeat units of the same tandem repeat do not have the same sequence.

Engineered (or man-made or artificial) TAL effectors have been produced by modification of naturally-occurring TAL effectors.

For example, engineered (or man-made or artificial) TAL effectors have been produced by truncation of a naturally-occurring TAL effector, to produce fragments of naturally-occurring TAL effector, which have retained the DNA-binding function of the full length TAL effector. More particularly, engineered (or man-made or artificial) TAL effectors have been produced by truncation of the acidic transcriptional Activation Domain, to produce a fragment of a naturally-occurring TAL effector, which is devoid of the acidic transcriptional Activation Domain, but which has retained the DNA-binding function of the full length TAL effector.

Engineered (or man-made or artificial) TAL effectors have been produced by modification of the RVD sequence and/or by modification of the number of repeat units of naturally-occurring TAL effectors or of fragments thereof, to recode them for defined target DNA sequences (cf. e.g., WO 2011/072246 (and its national counterparts, more particularly its US counterpart(s) (including the US continuation and divisional application(s)), WO 2010/079430 (and its national counterparts, more particularly its US counterpart(s) (including the US continuation and divisional application(s))).

TAL effectors have been used in genome editing (Bedell et al. 2012, Cade et al. 2012, Chen et al. 2013, Qiu et al. 2013).

However, it is believed that TAL effectors and TALENs have not been previously used for partial or full deletion of an (expanded) DNA tandem repeat, more particularly for partial or full deletion of an (expanded) DNA tandem repeat, which is contained in a double-stranded DNA molecule, more particularly for partial or full deletion of an (expanded) DNA tandem repeat, which is contained in a double-stranded DNA molecule and, which forms a non-linear secondary structure, such as a hairpin, a triple helix or a tetraplex secondary structure.

It is also believed that TAL effectors and TALENs have not been previously used for partial or full deletion of an (expanded) DNA tandem repeat that is contained in a double-stranded DNA molecule, such as those observed in pathological conditions.

The structure of the means of the application is especially adapted for partial or full deletion of at least one DNA tandem repeat, more particularly for partial or full deletion of at least one DNA tandem repeat in a double-stranded DNA, more particularly for partial or full deletion of at least one DNA tandem repeat, which is contained in a double-stranded DNA and, which forms a non-linear secondary structure, such as a hairpin, a triple helix or a tetraplex secondary structure.

The structure of the means of the application is especially adapted for partial or full deletion of at least one (expanded) DNA tandem repeat that is contained in a double-stranded DNA molecule, such as those observed in pathological conditions.

One of the means of the application is a DNA-binding polypeptide, which binds, or specifically binds, to a DNA nucleic acid comprising at least one DNA tandem repeat, wherein said DNA-binding polypeptide comprises a TAL effector tandem repeat. A TAL effector tandem repeat consists of adjacent amino acid units (of TAL effector tandem repeat), each containing a Repeat Variable Diresidue (RVD) that determines recognition of a nucleotide (cf. above).

According to an embodiment of the application, said TAL effector tandem repeat units are immediately or directly adjacent to each other, i.e., are contiguous.

Said DNA-binding polypeptide may further comprise at least one Nuclear Localization Signal (NLS), more particularly at least one NLS of a TAL effector.

The term "polypeptide" is herein intended in accordance with its ordinary meaning in the field of biology. The term "polypeptide" generally refers to a chain of amino acids linked by peptidic linkage. It does not imply any restriction in maximal length of the amino acid chain. As described below, a DNA-binding polypeptide of the application comprises several units of TAL effector, and therefore has a minimal length that typically is above 50 amino acids, more particularly above 60 amino acids, more particularly above 70 amino acids, more particularly above 100 amino acids, more particularly above 150 amino acids, more particularly of at least 200 amino acids. The maximal length of a DNA-binding polypeptide of the application typically is below 2,000 amino acids, more particularly below 1,500 amino acids, more particularly below 1,400 amino acids, more particularly below 1,000 amino acids.

The DNA nucleic acid, to which the polypeptide of the application binds or specifically binds, is a DNA nucleic acid that comprises at least one DNA tandem repeat.

Said DNA nucleic acid can e.g., be a double-stranded DNA nucleic acid or a strand of a double-stranded DNA nucleic acid, more particularly a double-stranded DNA nucleic acid, more particularly a chromosomal double-stranded DNA nucleic acid, more particularly a double-stranded DNA nucleic acid that is contained in a chromosome. Said double-stranded DNA nucleic acid can e.g., be a gene, more particularly a eukaryotic gene, more particularly a non-mammalian eukaryotic gene (e.g., a yeast gene) or a non-human mammalian gene (e.g., a rodent gene, a rat gene, a mouse gene, a pig gene, a rabbit gene) or a human gene. According to an embodiment of the application, said at least one DNA nucleic acid is a gene (or a strand of a gene), more particularly a human gene (or a strand of a human gene). Advantageously, said gene (more particularly, said human gene) is contained in a chromosome.

Said at least one DNA tandem repeat can be contained at any location(s) of said gene, e.g., in a promoter and/or in the 5'UTR and/or in at least one exon and/or in at least one intron and/or in the 3'UTR of said gene.

In a DNA-binding polypeptide of the application, the ordered series of RVDs formed by the RVDs respectively contained in said adjacent units of TAL effector tandem repeat, in N- to C-orientation, is an ordered series of amino acids, which, according to the acknowledged RVD/nucleotide correspondence, determines the recognition of the 5'-3' nucleotide sequence of a DNA target site contained in said DNA nucleic acid.

An acknowledged RVD/nucleotide correspondence is shown in Table 5 above.

According to an advantageous aspect of the application, a DNA-binding polypeptide of the application does not comprise the acidic transcriptional Activation Domain (AD) of a TAL effector. Such a DNA-binding polypeptide of the application does not have the function of transcriptional activation that a naturally-occurring TAL effector has, but has retained the DNA-binding function of a full length TAL effector.

The sequence of said DNA target site consists of:
i. a fragment of the sequence of said at least one DNA tandem repeat, or
ii. a fragment of the sequence of said DNA nucleic acid, which starts outside the sequence of said at least one DNA tandem repeat and which ends within the sequence of said at least one DNA tandem repeat, or conversely, which starts within the sequence of said at least one DNA tandem repeat and which ends outside the sequence of said at least one DNA tandem repeat. For the sake of concision, a DNA target site, the sequence of which satisfies feature i. above, will herein after be referred to as "non-overlapping DNA target site", and a DNA target site, the sequence of which satisfies feature ii. above, will herein after be referred to as "overlapping DNA target site".

Figure 1B:
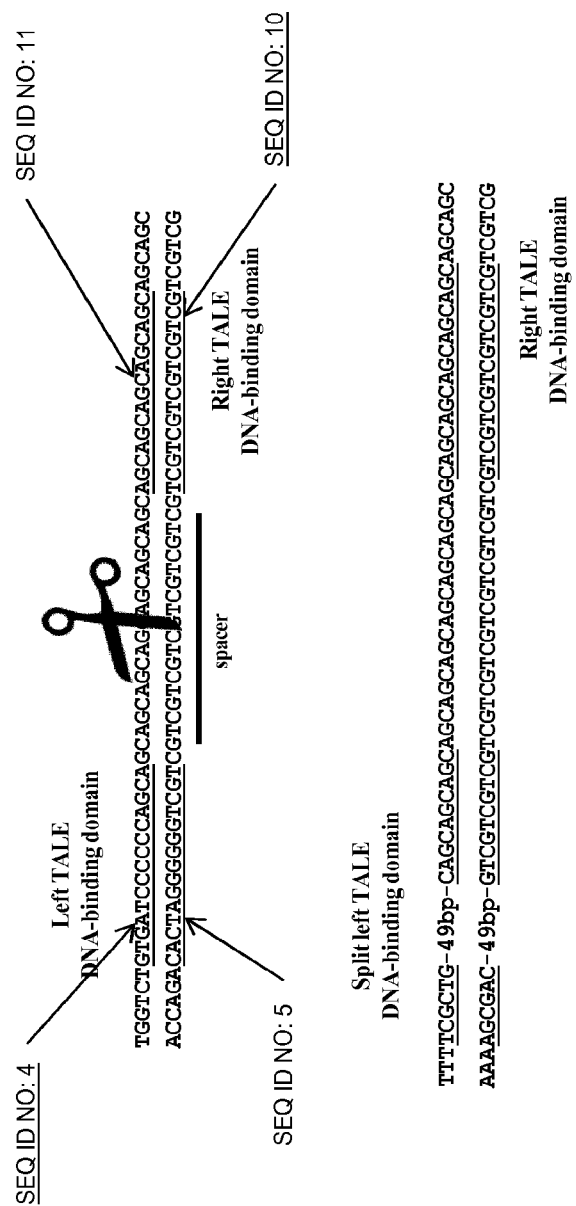

An example of non-overlapping DNA target site is the DNA target site of SEQ ID NO: 10 or 11 (cf. example 1 and FIG. 1B).

According to an embodiment of the application, the DNA target site of a DNA-binding polypeptide of the application is a non-overlapping DNA target site.

An example of overlapping DNA target site is the DNA target site of SEQ ID NO: 4 or 5 (cf. example 1 and FIG. 1B).

For example, said DNA target site is:
either fully comprised within the DNA tandem repeat sequence: cf. e.g., the DNA target site $^{5'}G(CTG)_4CT^{3'}$ (SEQ ID NO: 10) shown underlined in FIG. 1B (right TALE binding domain), or, is an overlapping site consisting of a fragment of the 5' or 3' end of the DNA tandem repeat sequence (wherein said fragment contains the first nucleotide at said 5' end or the last nucleotide at said 3' end respectively) and of a fragment of the DNA sequence that is immediately adjacent to said 5' or 3' end of DNA tandem repeat sequence outside said DNA tandem repeat sequence respectively, i.e., a target site, which, for a portion of it, is the 5' or 3' end (or extremity) of the DNA tandem repeat sequence and for the rest of it the DNA sequence that is immediately or directly adjacent to said 5' or 3' end of DNA tandem repeat sequence (outside the DNA tandem repeat sequence): cf. e.g., the DNA target site $^{5'}GTGATCCCCCCAGCA^{3'}$ (SEQ ID NO: 4) shown underlined in FIG. 1B (non-split left TALE binding domain), wherein the last five nucleotides, i.e., $^{5'}CAGCA^{3'}$ (SEQ ID NO: 6) is the sequence of the 5' end of the DNA tandem repeat and wherein $^{5'}GTGATCCCCC^{3'}$ (SEQ ID NO: 7) is the DNA sequence that is immediately adjacent to the 5' end of the DNA tandem repeat sequence outside said DNA tandem repeat sequence (i.e., the gene sequence that is immediately or directly adjacent to the 5' end of $^{5'}CAGCA^{3'}$).

According to an embodiment of the application, the DNA target site of a DNA-binding polypeptide of the application is an overlapping DNA target site.

A DNA tandem repeat occurs in a DNA nucleic acid, when a DNA sequence unit (or pattern) of 2, 3, 4, 5 or more nucleotides is repeated, i.e., the same DNA sequence unit of 2, 3, 4, 5 or more nucleotides is identically repeated. Said DNA sequence unit can be any sequence of at least two nucleotides, more particularly of at least two different nucleotides.

When they relate to a DNA nucleic acid, the phrases "repeat", "tandem repeat", "sequence unit(s)" and "unit(s)" (or equivalent or similar phrases) are given their respective general meaning of the field of DNA nucleic acids and DNA tandem repeats. For example, the nucleic acid GTGATCCCCC<u>CAGCAGCAGCAGCAGCAGCAGCAG</u> [SEQ ID NO: 23] contains a DNA tandem repeat consisting of eight copies of the sequence unit CAG (said eight copies are shown underlined in SEQ ID NO: 23 above).

According to an aspect of the application, said DNA sequence unit consists of 2, 3, 4 or 5 nucleotides, wherein at least two nucleotides of said unit are different nucleotides.

According to an aspect of the application, said DNA sequence unit consists of 3, 4 or 5 nucleotides, wherein at least two nucleotides of said unit or (at least) three nucleotides of said unit are different nucleotides.

According to an aspect of the application, said DNA sequence unit is selected from the group consisting of $^{5'}CTG^{3'}$, $^{5'}CAG^{3'}$, $^{5'}CAA^{3'}$, $^{5'}TTG^{3'}$, $^{5'}GAC^{3'}$, $^{5'}GTC^{3'}$, $^{5'}CCTG^{3'}$, $^{5'}CAGG^{3'}$, $^{5'}ATTCT^{3'}$, $^{5'}AGAAT^{3'}$, $^{5'}GCG^{3'}$, $^{5'}CGC^{3'}$, $^{5'}CGG^{3'}$ and $^{5'}CCG^{3'}$.

According to an aspect of the application, said DNA sequence unit consists of 3 or 4 nucleotides, wherein at least two nucleotides of said unit or (at least) three nucleotides of said unit are different nucleotides.

According to an aspect of the application, said DNA sequence unit is selected from the group consisting of $^{5'}CTG^{3'}$, $^{5'}CAG^{3'}$, $^{5'}CAA^{3'}$, $^{5'}TTG^{3'}$, $^{5'}GAC^{3'}$, $^{5'}GTC^{3'}$, $^{5'}CCTG^{3'}$, $^{5'}CAGG^{3'}$, $^{5'}GCG^{3'}$, $^{5'}CGC^{3'}$, $^{5'}CGG^{3'}$ and $^{5'}CCG^{3'}$.

According to an aspect of the application, said DNA sequence unit consists of 3 nucleotides, wherein at least two nucleotides of said unit or the three nucleotides of said unit are different nucleotides.

According to an aspect of the application, said DNA sequence unit is selected from the group consisting of 5'CTG3', 5'CAG3', 5'CAA3', 5'TTG3', 5'GAC3', 5'GTC3', 5'GCG3', 5'CGC3', 5'CGG3' and 5'CCG3.

The number of DNA sequence units that are repeated in said at least one DNA tandem repeat is of at least 2 units. According to an aspect of the application, said number is of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 or 52 units.

Within a DNA tandem repeat, the copies of the sequence unit are adjacent to each other. They can either be spaced apart from each other by only a few nucleotides, e.g., by less than 11, 10, 9, 8, 7, 6, 5, 4, 3, 2 nucleotides, or can be directly adjacent to each other. According to an aspect of the application, said copies of DNA sequence unit are spaced apart from each other by only a few nucleotides, e.g., by less than 6, 5, 4, 3, 2 nucleotides, or are directly adjacent to each other. According to an aspect of the application, said copies of DNA sequence unit are directly adjacent to each other. For example, in the above-mentioned nucleic acid of SEQ ID NO: 23, said copies of DNA sequence unit (i.e., the copies of the sequence unit CAG) are directly adjacent to each other.

According to an aspect of the application, one DNA sequence unit (or pattern) does not consist of the same nucleotide. For example, the sequence unit CAG consists of three different nucleotides (C, A and G).

In the application, a DNA tandem repeat is a direct tandem repeat, i.e., it is not an inverted tandem repeat: the order in which the nucleotides are contained in one DNA sequence unit is conserved throughout the DNA tandem repeat.

When they relate to TAL effector or TALEN, the phrases "repeat", "tandem repeat", "unit(s) of tandem repeat", "TAL effector repeat unit(s)" or "repeat unit(s)" (or equivalent or similar phrases) are given their respective general meaning of the field of TAL effectors and TALENs. TAL effector repeat units are the amino acid units that form the tandem repeat of the TAL effector, i.e., the amino acid units, which determine the (specific) recognition of the nucleotide sequence of the DNA target site through the N- to C-ordered series of RVDs they respectively contain.

As mentioned above, the units, which are considered (and computed) as TAL effector repeat units, are those, which determine the recognition of the DNA target site by direct correspondence of the N- to C-ordered series of RVDs they form with the 5'-3' nucleotide sequence of the DNA target site (e.g., in accordance with Table 5 above). TAL effector repeat units do not include any TAL effector amino acid unit, which would not be involved in said (specific) recognition, such as e.g., the unit, which is in C-term of the central domain of a naturally-occurring TAL effector and, which is truncated at 20 amino acids.

The tandem repeat (or central domain) of a TAL effector consists of adjacent amino acid sequence(s), which are known as the repeat units of said TAL effector, and which each consist of a frame sequence in which a RVD is contained. Please see above for the description of the typical structure of a TAL effector, more particularly of a TAL effector repeat unit.

Said repeat units can be directly or non-directly adjacent to each other; they are more particularly directly adjacent to each other.

For example, the polypeptide LTPEQVVAIASHDGGKQALETVQRLLPVLCQAHGLTP EQVVAIASNGGGKQALETVQ RLLPVLCQAHGLT-PEQVVAIASNIGGKQALETVQRLLPVLCQAHGLT-PEQVVAIASNN GGKQALETVQRLLPVLCQAHGLT-PEQVVAIASNSGGKQALETVQRLLPVLCQAHGLT PEQVVAIASNGGKQALETVQRLLPVLCQAHGLT-PEQVVAIASHGGGKQALETVQRLL PVLCQAHGLT-PEQVVAIASHGGKQALETVQRLLPVLCQAHG [SEQ ID NO: 24] is a TAL effector tandem repeat consisting of eight (directly adjacent) copies of the repeat unit LTPEQVVAIASXXGGKQALETVQRLLPVLCQAHG [SEQ ID NO: 25], wherein XX is the RVD and wherein the RVD is:

HD in the first repeat unit,
NG in the second repeat unit,
NI in the third repeat unit,
NN in the fourth repeat unit,
NS in the fifth repeat unit,
N* in the sixth repeat unit,
HG in the seventh repeat unit, and
H* in the eighth repeat unit, (the first repeat unit is shown underlined in SEQ ID NO: 24, the RVDs are shown in bold characters in each of the eight units). In this example, the frame sequence of the TAL effector tandem repeat unit is the sequence of SEQ ID NO: 25 (in this example, the frame sequence is the same for each of the eight repeat units).

In a DNA-binding polypeptide of the application, the number of amino acids that are contained in one TAL effector tandem repeat unit can be 33, 34 or 35 (i.e., the same as in a naturally-occurring TAL effector), or can be lower, e.g., 29, 30, 31 or 32.

Hence, in a DNA-binding polypeptide of the application, the number of amino acids that are contained in one TAL effector tandem repeat unit can be an integer selected from 29-35, or from 30-35, or from 31-35, or from 32-35, or from 29-34, or from 30-34, or from 31-34, or from 32-34, or from 30-33, or from 30-34, or from 31-33, or from 32-33.

According to an aspect of the application, the number of amino acids that are contained in one repeat unit is 33, 34 or 35 (i.e., the same as in a naturally-occurring TAL effector), more particularly 34.

The TAL effector repeat units of a DNA-binding polypeptide of the application can each consist of the same number of amino acids, or can consist of different numbers of amino acids. According to an embodiment of the application, the TAL effectors repeat units of a DNA-binding polypeptide of the application each consist of the same number of amino acids, e.g., 33, 34 or 35 amino acids, e.g., 34 amino acids.

The N- to C-ordered series of TAL effector repeat units of a DNA-binding polypeptide of the application can be followed in C-term by a truncated unit, which consists of less than 29 amino acids, more particularly a unit, which is truncated after the RVD (i.e., after the amino acid at position 13), e.g., which is truncated immediately after the amino acid at position 28, 27, 26, 25, 24, 23, 22, 21, 20, 19, 18, 17, 16, 15, 14 or 13. An example of such a truncated unit is the unit of SEQ ID NO: 56 (LTPQQVVAIASNGG), which can be viewed as a truncation of the TAL effector repeat unit of SEQ ID NO: 46 (LTPQQVVA-IASXXGGKQALETVQRLLPVLCQAHG) at amino acid position 14 with XX=NG. Such a truncated unit is not involved in the (specific) recognition of the nucleotide sequence of the DNA target site and therefore is not considered as, and not computed as a TAL effector repeat unit.

As mentioned above, the units, which are considered (and computed) as TAL effector repeat units, are those, which determine the recognition of the DNA target site by direct correspondence of the N- to C-ordered series of RVDs they form with the 5'-3' nucleotide sequence of the DNA target site (e.g., in accordance with Table 5 above).

Units, which would not determine said recognition, such as the above-mentioned truncated unit, are not considered, and are not computed, as a TAL effector repeat unit.

Hence, in the application, units, which consist of 29-35 amino acids as described above, can be considered (and computed) as TAL effector repeat units, whereas the above-mentioned truncated unit is not considered (and is not computed) as a TAL effector repeat unit.

The frame sequence of a TAL effector repeat unit is largely invariant among the TAL effectors. Examples of (the frame sequence of a) TAL effector repeat unit comprise:

```
the sequence of SEQ ID NO: 25
(LTPEQVVAIASXXGGKQALETVQRLLPVLCQAHG; cf.
example 1 below), the sequence of SEQ ID NO: 46
(LTPQQVVAIASXXGGKQALETVQRLLPVLCQAHG; cf.
example 1 below), the sequence of SEQ ID NO: 55
(LTPEQVVAIASXXGGKQALETVQALLPVLCQAHG; cf.
example 1 below), the sequence of SEQ ID NO: 26
(LTPDQVVAIASXXGGKQALETVQRLLPVLCQDHG)
``` wherein XX stands for the RVD. Please note that, in a RVD sequence "XX", the first X is an amino acid, whereas the second X is an amino acid or is absent (cf. e.g., N* or H* in Table 5 above).

Other examples of (the frame sequence of a) TAL effector repeat unit comprise amino acid units, the respective sequences of which are variant sequences of at least one of the sequences of SEQ ID NOs: 25, 46, 55, 26. Said variant sequences:

consist of 33, 34 or 35 amino acids,
are at least 50%, more particularly at least 51%, or at least 52%, or at least 53%, or at least 54%, or at least 55%, or least 55.5% identical to at least one of SEQ ID NOs: 25, 46, 55 and 26 over the whole length of said at least one SEQ ID sequence,
have retained the "XX" RVD sequence at positions 12 and 13, and
have retained the nucleotide recognition capacity of a TAL effector tandem repeat unit (i.e., which determine the recognition of a nucleotide through said "XX" RVD).

According to an aspect of the application, said XX is selected from the group consisting of HD, NG, NI, NN, NS, N*, HG, H*, IG, HA, ND, NK, HI, HN, NA, SN and YG. The symbol * denotes that the second X is missing (cf. e.g., Table 5 above).

A TAL effector tandem repeat can be:
formed by the same unit frame sequence, which is identically repeated (like a homopolymer wherein only the RVDs vary), such as illustrated above by the sequence of SEQ ID NO: 24, or can be
formed by different unit frame sequences, i.e., the TAL effector repeat units do not all have the same frame sequence (like a heteropolymer, e.g., as in the TAL effector tandem repeat sequence coded by SEQ ID NO: 45 or SEQ ID NO: 54).

The TAL effector repeat units of a DNA-binding polypeptide of the application can have each different frame sequences. Nevertheless, a TAL effector tandem repeat of a DNA-binding polypeptide of the application generally consists of repeat units wherein at least one frame sequence is identically repeated.

Although the TAL effector repeat units of a DNA-binding polypeptide can have different frame sequences, said units are considered to be "repeat units" in accordance with the acknowledged terminology in the field of TALE effector and TALENs. Indeed, the sequence variation between (the frame sequences of) two different TAL effector units is low (cf. e.g., the sequence variation between the 34aa-long sequences of SEQ IDs: 25, 26, 46 and 55) and the function is conserved.

Hence, in a DNA-binding polypeptide of the application, the adjacent units of TAL effector tandem repeat may for example comprise or consist of one or several copy(ies) of at least one sequence selected from the group consisting of SEQ ID NOs: 25, 26, 46, 55 and said variant sequences thereof, and/or comprise one or several copy(ies) of at least one of the sequences of TAL effector tandem repeat units of the DNA-binding polypeptide, which is coded by the plasmid deposited at the Collection Nationale de Culture de Microorganismes (C.N.C.M.), Paris, France, under deposit number I-4804 or under deposit number I-4805.

The total number of the adjacent units forming the TAL effector tandem repeat of a DNA-binding polypeptide of the application can be from 8 to 39, usually from 10 to 33, 13 to 33, 13 to 34, 13 to 35, 14 to 33, 14 to 34 or 14 to 35, for example from 12 to 27, 13 to 28, from 14 to 28, from 14 to 22, from 15 to 21, e.g., 15, 16, 17, 18, 19, 20 or 21.

For example, in FIG. 1B, each of the two engineered TAL effectors binds to a target DNA site consisting of 15 nucleotides (SEQ ID NO: 4 and 10, respectively); therefore, the number of repeat units of each of said two engineered TAL effectors is 15.

Every combination of amino acid length of a TAL effector tandem repeat unit and of number of TAL effector tandem repeat units is herein explicitly encompassed, e.g., a number of amino acids of 29-35 per TAL effector tandem repeat unit and a number of 13-33 TAL effector tandem repeat units per polypeptide, or a number of amino acids of 33-35 per TAL effector tandem repeat unit and a number of 12-27 TAL effector tandem repeat units per polypeptide.

A DNA-binding polypeptide of the application can be a non-naturally-occurring polypeptide, e.g., a man-made or artificial or engineered polypeptide.

According to an aspect of the application, a DNA-binding polypeptide of the application does not comprise the acidic transcriptional activation domain (AD) of a TAL effector. According to this aspect of the application, a DNA-binding polypeptide of the application can be viewed as a fragment of TAL effector or of engineered TAL effector, which still comprises the tandem repeat and the NLS of said (engineered) TAL effector, and which is advantageously devoid of the acidic transcriptional activation domain (AD) of said TAL effector. Examples of such fragments notably include the BamHI fragment of said TAL effector.

The total length of the TAL effector tandem repeat of a polypeptide of the application (i.e., the total length formed by the adjacent amino acid units forming said TAL effector tandem repeat) can e.g., be above 50, 60, 70, 100, 150, 200, 250, 300, 350, 400, 450, 500, 550, 600, 650 or 700 amino acids and/or below 2,000, 1,800, 1,600, 1,500, 1,400, 1,200, 1,000, 900, 800 or 750 amino acids.

Every combination of one of these minimal lengths and of one of these maximal lengths is herein explicitly encompassed, e.g., a length above 50 and below 1,400 amino acids, or a length above 60 and below 1,400 amino acids, or above 70 and below 1,400 amino acids, or above 1000 and below 1,400 amino acids, or above 150 and below 1,400 amino acids, or above 200 and below 1,400 amino acids, or above 300 and below 1,500 amino acids, or above 400 and below 1,200 amino acids, or above 500 and below 1,200 amino acids, or above 600 and below 1,200 amino acids, or above 600 and below 1,000 amino acids, or above 650 and below 800 amino acids, or above 700 and below 750 amino acids.

Hence, a DNA-binding polypeptide of the application can e.g., comprise a TAL effector tandem repeat, wherein the total number of adjacent amino acid units forming said TAL effector tandem repeat is 8 to 39 (more particularly, 10 to 33, 13 to 33, 13 to 34, 13 to 35, 14 to 33, 14 to 34 or 14 to 35, for example from 12 to 27, 13 to 28, from 14 to 28, from 14 to 22, from 15 to 21, e.g., 15, 16, 17, 18, 19, 20 or 21), wherein each of said adjacent units of said TAL effector tandem repeat is selected from the group consisting of the sequences of SEQ ID NOs: 25, 26, 46, 55 and said variant sequences thereof, and wherein the N- to C-ordered series of RVDs formed by said adjacent repeat units determine the recognition of an overlapping DNA target site or of a non-overlapping DNA target site.

Said DNA-binding polypeptide may further comprise at least one NLS, more particularly at least one NLS of TAL effector.

According to an aspect of the application, the DNA target site, which is recognized by the ordered series of RVDs of the TAL effector tandem repeat units of a DNA-binding polypeptide of the application, consists of 8 to 39 nucleotides, more particularly of 13 to 33, 13 to 34, 13 to 35, 14 to 33, 14 to 34 or 14 to 35 nucleotides, for example of 13 to 28 nucleotides, of 14 to 28 nucleotides, of 14 to 22 nucleotides, of 15 to 21 nucleotides, e.g., of 15, 16, 17, 18, 19, 20 or 21 nucleotides.

According to an aspect of the application, said DNA target site consists of a number of nucleotides, which is identical to the number of TAL effector tandem repeat units of said DNA-binding polypeptide.

According to an aspect of the application, a non-overlapping DNA target site as defined above is a fragment of said at least one DNA tandem repeat, and comprises more than one copy of the DNA sequence unit of said at least one DNA tandem repeat, more particularly at least 2, 3, 4, 5, 6, 7, 8, 9, 10, 11, 12 or 13 (adjacent or directly adjacent) copies of the DNA sequence unit of said at least one DNA tandem repeat, more particularly at least 2, 3, 4, 5, 6, 7, 8, 9, 10, 11, 12 or 13 directly adjacent copies of the DNA sequence unit of said at least one DNA tandem repeat.

According to an aspect of the application, the number of copy(ies) of DNA sequence unit in said fragment of said at least one DNA tandem repeat is an integer.

According to an alternative or complementary aspect of the application, said copy number is not an integer, i.e., it is a number with decimals (more particularly a number with two decimals). For example, if the DNA sequence unit consists of 3 nucleotides, and if the fragment of the DNA tandem repeat that is contained in the non-overlapping DNA target site consists of five nucleotides, i.e., if it consists of one unit copy (3 nucleotides) and (directly adjacent thereto) two thirds of another unit copy (2 nucleotides), the copy number is 3/3+2/3=1.67, i.e., the copy number is not an integer.

When it relates to a non-overlapping DNA target site, the expression "more than one copy" encompasses a copy number, which is or not an integer, more particularly a copy number, which is more than one and less than two, such as a copy number of 1.67, as well as a copy number of two and above.

A non-overlapping DNA target site can e.g., be a fragment of said at least one DNA tandem repeat, which comprises or consists of more than one copy of the DNA sequence unit, e.g., which comprises or consists of:
  one copy, or several directly adjacent copies, of the DNA sequence unit, and, directly adjacent thereto (in 5' and/or in 3'),
  zero, one fragment of said DNA sequence unit (in 5' and/or in 3'), or two fragment(s) of said DNA sequence unit (one fragment in 5' and one fragment in 3').

For example, if the DNA sequence unit of the DNA tandem repeat is $^5{}'CTG^{3'}$, the sequence of the non-overlapping DNA target site can e.g., be $^5{}'G(CTG)_4CT^{3'}$ (SEQ ID NO: 10), i.e., a fragment of the DNA tandem repeat, which consists of four $^5{}'CTG^{3'}$ units ($(CTG)_4$) and, directly adjacent thereto, two fragments of DNA sequence unit (fragment G in 5' and fragment CT in 3').

An example of non-overlapping DNA target site is the DNA target site of SEQ ID NO: 10 or of SEQ ID NO: 11 (cf. FIG. 1B). Hence, a DNA-binding polypeptide of the application can e.g., comprise a TAL effector tandem repeat as defined above, wherein said units are selected from the group consisting of the sequences of SEQ ID NOs: 25, 26, 46, 55 and said variant sequences thereof, and wherein the N- to C-ordered series of RVDs formed by the RVDs respectively contained in said units determines the recognition of a non-overlapping DNA target site as defined above, e.g., the DNA target site of SEQ ID NO: 10 or of SEQ ID NO: 11. An example of N- to C-ordered series of RVDs, which determines the recognition of the DNA target site of SEQ ID NO: 10 [$^5{}'G(CTG)_4CT^{3'}$], is: NN; HD; NG; NN; HD; NG; NN; HD; NG; NN; HD; NG; NN; HD and NG (cf. Table 5 above).

An example of TAL effector tandem repeat, which can be comprised in a DNA-polypeptide of the application and, which (specifically) binds to a non-overlapping DNA target site, is the polypeptide coded by the sequence of SEQ ID NO: 45 (cf. example 1 below), which (specifically) binds to the non-overlapping DNA target site of SEQ ID NO: 10.

An example of TAL effector tandem repeat, which can be comprised in a DNA-polypeptide of the application and, which (specifically) binds to a non-overlapping DNA target site, is the TAL effector tandem repeat coded by plasmid pCLS9996exp (C.N.C.M. deposit number I-4804), which (specifically) binds to the non-overlapping DNA target site of SEQ ID NO: 10.

The sequence of an overlapping DNA target site as defined above is the sequence of a fragment of said DNA nucleic acid, which, for a portion of it, is within said at least one DNA tandem repeat [the "inside" portion], and which, for the remaining portion of it, is outside said at least one DNA tandem repeat [the "outside" portion].

For example, if the sequence of the overlapping DNA target site is $^5{}'GTGATCCCCCCAGCA^{3'}$ (SEQ ID NO: 4) within a DNA nucleic acid comprising the $(CAG)_n$ tandem repeat (cf. FIG. 1B), the portion of the DNA target site, which is within the DNA tandem repeat [the "inside" portion], consists of $^5{}'CAGCA^{3'}$ (SEQ ID NO: 6), and the remaining portion, which is outside said DNA tandem repeat [the "outside" portion], is $^5$'GTGATCCCCC$^{3'}$ (SEQ ID NO: 7), i.e., 10 nucleotides.

The portion of an overlapping DNA target site, which is within said at least one DNA tandem repeat [the "inside" portion], is a fragment of said at least one DNA tandem repeat, and consists of at least a fragment of a copy of the DNA sequence unit of said at least one DNA tandem repeat, more particularly of one, at least one or more than one copy of the DNA sequence unit of said at least one DNA tandem repeat, more particularly of two, at least two, three, at least three, four or at least four (adjacent or directly adjacent) copies of the DNA sequence unit of said at least one DNA tandem repeat.

According to an aspect of the application, said copy number is an integer (e.g., in the DNA tandem repeat fragment $^5$'CAGCAG$^{3'}$ (SEQ ID NO: 35), the copy number is two (two $^5$'CAG$^{3'}$ units)).

According to an alternative or complementary aspect of the application, said copy number is not an integer i.e., it is a number with decimals (more particularly a number with two decimals). For example, if the sequence of the overlapping DNA target site is $^5$'GTGATCCCCCCAGCA$^{3'}$ (SEQ ID NO: 4) within a DNA nucleic acid comprising the (CAG)$_n$ tandem repeat (cf. FIG. 1B), the portion of the DNA target site, which is within the DNA tandem repeat [the "inside" portion], consists of $^5$'CAGCA$^{3'}$ (SEQ ID NO: 6), i.e., consists of one DNA sequence unit (unit CAG) and (directly adjacent thereto) a fragment of the DNA sequence unit (CA), i.e., the "inside" portion consists of one unit copy (unit CAG) and, directly adjacent thereto, two thirds of another unit copy (CA), the copy number is 1+⅔=1.67, i.e., the copy number is not an integer.

When it relates to the portion of an overlapping DNA target site, which is within the DNA tandem repeat, the expression "more than one copy" encompasses a copy number, which is or not an integer, more particularly a copy number, which is more than one and less than two, such as a copy number of 1.67, as well as a copy number of two and above.

More particularly, the portion of an overlapping DNA target site, which is within said at least one DNA tandem repeat [the "inside" portion], is a fragment of said at least one DNA tandem repeat, which comprises or consists of more than one copy of the DNA sequence unit, e.g., which comprises or consists of:
  one copy, or several directly adjacent copies, of the DNA sequence unit, and, directly adjacent thereto (in 5' and/or in 3'),
  zero, one fragment of said DNA sequence unit (in 5' and/or in 3'), or two fragment(s) of said DNA sequence unit (one fragment in 5' and one fragment in 3').

For example, if the DNA sequence unit of the DNA tandem repeat is $^5$'CTG$^{3'}$, the sequence of the portion of the overlapping DNA target site, which is within said at least one DNA tandem repeat [the "inside" portion], can e.g., be $^5$'G(CTG)$_4$CT$^{3'}$ (SEQ ID NO: 10), i.e., a fragment of the DNA tandem repeat, which consists of four $^5$'CTG$^{3'}$ units ((CTG)$_4$) and, directly adjacent thereto, two fragments of DNA sequence unit (fragment G in 5' and fragment CT in 3').

The portion of an overlapping DNA target site, which is outside said DNA tandem repeat [the "outside" portion], consists of at least 1, 2, 3, 4, 5, 6, 7, 8, 9 or 10 nucleotide(s), for example of at least 5 nucleotides or of more than 5 nucleotides, more particularly of at least 6, 7, 8, 9 or 10 nucleotides.

Any combination of:
  said number of nucleotides of the "outside" (or first) portion and of
  said copy number of DNA repeat unit(s) of the "inside" (or second) portion
is herein explicitly encompassed, e.g., an overlapping DNA target site, comprising at least one or more than one copy of the DNA repeat unit of said at least one DNA tandem repeat (cf. above) and comprising an "outside" portion of at least 5, 6 or 7 nucleotides.

Alternatively or complementarily, the sequence of an overlapping DNA target site as defined above can be viewed as the sequence of a fragment of said DNA nucleic acid, which comprises or consists of:
  a. a sequence comprising, or consisting of, at least one, or more than one, copy of the DNA sequence unit (cf. above),
  and, directly adjacent thereto, in 5' or in 3',
  b. a sequence, which is of at least 5 nucleotides or of more than five nucleotides, and which differs from the sequence of a.

Alternatively or complementarily, the sequence of an overlapping DNA target site can be viewed as the sequence of a fragment of said DNA nucleic acid, which comprises, but does not consist of, a fragment of said at least one DNA tandem repeat, wherein the copy number of said DNA sequence unit in said fragment of said at least one DNA tandem repeat is at least one or more than one, more particularly more than one.

More particularly, said fragment of said DNA nucleic acid further comprises another sequence, which is of at least five or of more than five nucleotides, and which is directly adjacent in 5' or in 3' to said fragment of said at least one DNA tandem repeat. More particularly, the end of said sequence of at least five or of more than five nucleotides, which is directly linked to said fragment of said at least one DNA tandem repeat, is a sequence (e.g., of the same length as said DNA sequence unit, but) which differs from the sequence of said DNA sequence unit.

Alternatively or complementarily, the sequence of an overlapping DNA target site can be viewed as the sequence of a fragment of said DNA nucleic acid, which consists of:
  a. a nucleotide sequence, which is a fragment of said at least one DNA tandem repeat, wherein the copy number of said DNA sequence unit in said fragment of said at least one DNA tandem repeat is more than one (said more than one copy being adjacent or directly adjacent to each other, more particularly directly adjacent to each other), and
  b. a nucleotide sequence of at least five or of more than five nucleotides, which differs from said sequence of a., and which is directly linked, in 5' or in 3', to said nucleotide sequence of a.,
  wherein the end of said nucleotide sequence of b., which is directly linked to said nucleotide sequence of a., is a sequence (e.g., of the same length as said DNA sequence unit, but) which differs from the sequence of said DNA sequence unit.

Alternatively or complementarily, an overlapping DNA target site can be viewed as a fragment of said DNA nucleic acid, which consists of a portion, which is outside the DNA tandem repeat [the "outside" portion] and of a portion, which is inside the DNA tandem repeat [the "inside" portion], wherein the nucleotide length of said "outside" portion is more than 20%, more particularly more than 30%, more particularly more than 40%, more particularly more than 45%, more particularly more than 50%, more particularly more than 55%, more particularly more than 60% (but less than 100%) of the total length of said (full-length) DNA target site.

For example, if the sequence of the overlapping DNA target site is $^5$'GTGATCCCCCCAGCA$^3$' (SEQ ID NO: 4) within a DNA nucleic acid comprising the (CAG)$_n$ tandem repeat (cf. FIG. 1B), the portion of the DNA target site, which is outside the DNA tandem repeat, consists of $^5$'GTGATCCCCC$^3$' (SEQ ID NO: 7), i.e., consists of 10 nucleotides, whereas the DNA target site consists of 15 nucleotides; hence, the portion of the overlapping DNA target site, which is outside the DNA tandem repeat, consists of a number of nucleotides, which is ($^{10}$/$_{15}$×100=) 66.7%, i.e., of more than 60% (but less than 100%) of the total number of nucleotides of the DNA target site.

Advantageously, an overlapping DNA target site is a fragment of said DNA nucleic acid, which consists of a portion, which is outside the DNA tandem repeat [the "outside" portion] and of a portion, which is inside the DNA tandem repeat [the "inside" portion], wherein the nucleotide length of said "outside" portion is more than 40%, more particularly more than 45%, more particularly more than 50%, more particularly more than 55%, more particularly more than 60% (but less than 100%) of the total length of said (full-length) DNA target site.

Alternatively or complementarily, an overlapping DNA target site is a fragment of said DNA nucleic acid, which consists of a portion, which is outside the DNA tandem repeat [the "outside" portion] and of a portion, which is inside the DNA tandem repeat [the "inside" portion], wherein the nucleotide length of said "inside" portion is less than 80%, more particularly less than 70%, more particularly less than 60%, more particularly less than 55%, more particularly less than 50%, more particularly less than 45%, more particularly less than 40% (but more than 0% or more than 1%) of the total length of said (full-length) DNA target site. For example, if the sequence of the overlapping DNA target site is $^5$'GTGATCCCCCCAGCA$^3$' (SEQ ID NO: 4) within a DNA nucleic acid comprising the (CAG)$_n$ tandem repeat (cf. FIG. 1B), the portion of the DNA target site, which is inside the DNA tandem repeat, consists of $^5$'CAGCA$^3$' (SEQ ID NO: 6), i.e., of 5 nucleotides, whereas the DNA target site consists of 15 nucleotides; hence, the portion of the overlapping DNA target site, which is inside the DNA tandem repeat, consists of a number of nucleotides, which is ($^5$/$_{15}$×100=) 33.3%, i.e., of less than 40% (but more than 0% or more than 1%) of the total number of nucleotides of the DNA target site.

Advantageously, an overlapping DNA target site is a fragment of said DNA nucleic acid, which consists of a portion, which is outside the DNA tandem repeat [the "outside" portion] and of a portion, which is inside the DNA tandem repeat [the "inside" portion], wherein the nucleotide length of said "inside" portion is less than 60%, more particularly less than 55%, more particularly less than 50%, more particularly less than 45%, more particularly less than 40% (but more than 0% or more than 1%) of the total length of said (full-length) DNA target site.

Alternatively or complementarily, an overlapping DNA target site is a fragment of said DNA nucleic acid, which comprises, but does not consist of, a fragment of said at least one DNA tandem repeat, wherein the nucleotide length of said at least one DNA tandem repeat is more than 10% and less than 80%, more particularly more than 15% and less than 70%, more particularly more than 20% and less than 60%, more particularly more than 20% and less than 50%, more particularly more than 20% and less than 40%, of the total nucleotide length of said DNA target site.

An example of overlapping DNA target site is the DNA target site of SEQ ID NO: 4 or of SEQ ID NO: 5 (cf. FIG. 1B).

Hence, a DNA-binding polypeptide of the application can e.g., comprise a TAL effector tandem repeat as defined above, wherein said adjacent units are selected from the group consisting of the sequences of SEQ ID NOs: 25, 26, 46, 55 and said variant sequences thereof, and wherein the N- to C-ordered series of RVDs formed by said adjacent units determine the recognition of the (overlapping) DNA target site of SEQ ID NO: 4 or of SEQ ID NO: 5.

An example of N- to C-ordered series of RVDs, which determine the recognition of the DNA target site of SEQ ID NO: 4 [$^5$'GTGATCCCCCCAGCA$^3$'], is NN; NG; NN; NI; NG; HD; HD; HD; HD; HD; HD; NI; NN; HD and NI (cf. Table 5 above).

An example of TAL effector tandem repeat, which can be comprised in a DNA-polypeptide of the application, is the polypeptide coded by the sequence of SEQ ID NO: 54 (cf. example 1 below), which (specifically) binds to the overlapping DNA target site of SEQ ID NO: 4.

An example of TAL effector tandem repeat, which can be comprised in a DNA-polypeptide of the application, is the TAL effector tandem repeat coded by plasmid pCLS16715 (C.N.C.M. deposit number I-4805), which (specifically) binds to the overlapping DNA target site of SEQ ID NO: 4.

According to an aspect of the application, the sequence of the DNA target site that is recognized by the ordered series of RVDs of a DNA-binding polypeptide of the application is immediately preceded in 5' by the nucleotide T.

Indeed, it has been observed that the presence of the nucleotide T directly adjacent to the 5' end (or extremity) of the DNA target site might be advantageous to adequately or efficiently bind to a naturally-occurring DNA target.

For example, the DNA target site of SEQ ID NO: 10 (cf. right TALE binding domain of FIG. 1B) is immediately preceded in 5' by the nucleotide T. The DNA target site of SEQ ID NO: 4 (cf. the non-split left TALE binding domain of FIG. 1B) also is immediately preceded in 5' by the nucleotide T.

Said preceding T is not part of the DNA target site (the RVDs of the TALE effector do not determine the recognition of said T), but is believed to improve the stability of the binding.

The (at least one) DNA nucleic acid, to which the DNA-binding polypeptide of the application binds, or specifically binds, can e.g., be a double-stranded DNA nucleic acid or a strand of a double-stranded DNA nucleic acid.

Said DNA strand can be isolated from the other strand of the double-stranded DNA nucleic acid, whereby forming a single-stranded molecule, or can still be contained in said double-stranded DNA nucleic acid molecule (i.e., be still in duplex with its complementary strand). Advantageously, said DNA strand is still contained in said double-stranded DNA nucleic acid molecule.

Hence, the DNA nucleic acid, to which the DNA-binding polypeptide of the application binds, or specifically binds, advantageously is a double-stranded DNA nucleic. When said DNA nucleic acid is a double-stranded DNA nucleic acid, the DNA-binding polypeptide of the application binds to one of the two strands of the double-stranded DNA nucleic acid.

Said double-stranded DNA nucleic acid can e.g., be a chromosomal DNA nucleic acid, more particularly a chromosomal double-stranded DNA nucleic acid, more particularly a double-stranded DNA nucleic acid that is contained in a chromosome.

Said double-stranded DNA nucleic acid can e.g., be a gene, more particularly a eukaryotic gene, more particularly a non-mammalian eukaryotic gene (e.g., a yeast gene) or a non-human mammalian gene (e.g., a rodent gene, a rat gene, a mouse gene, a pig gene, a rabbit gene) or a human gene. According to an embodiment of the application, said at least one DNA nucleic acid is a gene, more particularly a human gene. Advantageously, said gene (more particularly, said human gene) is a chromosomal gene, more particularly a gene that is contained in a chromosome, more particularly a gene that is contained in a human chromosome.

According to an aspect of the application, the DNA nucleic acid, to which the DNA-binding polypeptide of the application binds, or specifically binds, is a double-stranded DNA nucleic, wherein at least one of its two strands contains nucleotide(s) T in the sequence of the DNA tandem repeat (i.e., in at least one of said two DNA strands, the unit of the DNA tandem repeat contains at least one nucleotide T). According to this aspect of the application, the DNA sequence unit that is repeated in the sequence of said T-containing DNA tandem repeat can e.g., be selected from the group consisting of $5'CTG^{3'}$, $5'TTG^{3'}$, $5'GTC^{3'}$, $5'CCTG^{3'}$, $5'ATTCT^{3'}$ and $5'AGAAT^{3'}$.

According to an aspect of the application, the DNA nucleic acid, to which the DNA-binding polypeptide of the application binds, or specifically binds, is a double-stranded DNA nucleic, wherein only one of its two strands contains the nucleotide T in the sequence of said at least one DNA tandem repeat (i.e., in one of said two DNA strands, the unit of the DNA tandem repeat contains at least one nucleotide T, whereas in the other of said two DNA strands, the unit of the DNA tandem repeat does not contain any nucleotide T). According to this aspect of the application, the DNA sequence unit that is repeated in the sequence of said T-containing DNA tandem repeat can e.g., be selected from the group consisting of $5'CTG^{3'}$, $5'TTG^{3'}$, $5'GTC^{3'}$ and $5'CCTG^{3'}$. The DNA-binding polypeptide of the application may bind to the strand that contains said nucleotide T, or may bind to the other strand. Please see FIG. 1B, which illustrates a human gene, wherein only one of its two strands contains the nucleotide T in the sequence of the DNA tandem repeat (i.e., the human gene coding for DM1, which comprises the (CAG)n tandem repeat in one strand and the (CTG)n tandem repeat in the complementary strand): as described in example 1 below, a first DNA-binding polypeptide of the application (i.e., the left-hand TALEN of example 1 below) binds to the strand containing the (CAG)n repeat at an overlapping DNA binding site (e.g., SEQ ID NO: 4), whereas a second DNA-binding polypeptide of the application, which is different from said first DNA-binding polypeptide of the application, (i.e., the right-hand TALEN of example 1 below) binds to the (complementary) strand containing the (CAG)n repeat at a non-overlapping DNA binding site (e.g., SEQ ID NO: 10).

According to an aspect of the application, the DNA nucleic acid, to which the DNA-binding polypeptide of the application binds, or specifically binds, is a double-stranded DNA nucleic, wherein each of its two strands contains the nucleotide T in the sequence of the DNA tandem repeat (i.e., in one of said two DNA strands, the unit of the DNA tandem repeat contains at least one nucleotide T, and in the other of said two DNA strands, the unit of the DNA tandem repeat also contains at least one nucleotide T). According to this aspect of the application, the DNA sequence unit that is repeated in the sequence of said (T-containing) DNA tandem repeat can e.g., be selected from the group consisting or $5'ATTCT^{3'}$ and $5'AGAAT^{3'}$.

According to an advantageous aspect of the application, the sequence of said at least one DNA tandem repeat can form a non-linear secondary structure, such as a hairpin, a triple helix or a tetraplex secondary structure.

According to an advantageous aspect of the application, said DNA nucleic acid can be any DNA nucleic acid, more particularly any double-stranded DNA nucleic acid (more particularly any human double-stranded DNA nucleic acid), more particularly any gene (more particularly any human gene), which is involved in a neurological and/or muscular and/or skeletal disorder or disease and/or in a disorder or disease involving at least one (abnormally-expanded) DNA tandem repeat, more particularly in a neurological and/or muscular and/or skeletal disorder or disease involving at least one (abnormally-expanded) DNA tandem repeat.

Examples of such disorders and diseases, as well as of the genes that are respectively involved in said disorders and diseases are given in Tables 6, 7 and 8 below. Table 8 below shows examples of the average number of DNA tandem repeat units that is observed in a healthy subject (normal average range of repeat units).

TABLE 6

DISEASE or DISORDER

| Acronym or abbreviation | Name | Phenotype MIM number (*) |
|---|---|---|
| DM1 | Myotonic dystrophy type 1 | 160900 |
| SCA8 | Spinocerebellar ataxia 8 | 608768 |
| SCA12 | Spinocerebellar ataxia 12 | 604326 |
| HDL2 | Huntington's disease-like 2 | 606438 |
| SBMA | Spinal and bulbar muscular atrophy (or Kennedy disease) | 313200 |
| HD | Huntington's disease | 143100 |
| DRPLA | Dentatorubral-pallidouysian atrophy | 125370 |
| SCA1 | Spinocerebellar ataxia 1 | 164400 |
| SCA2 | Spinocerebellar ataxia 2 | 183090 |
| SCA3 | Spinocerebellar ataxia 3 (Machado-Joseph disease) | 109150 |
| SCA6 | Spinocerebellar ataxia 6 | 183086 |
| SCA7 | Spinocerebellar ataxia 7 | 164500 |
| SCA17 | Spinocerebellar ataxia 17 | 607136 |
| PSACH | Pseudoachondroplasia | 177170 |
| DM2 | Myotonic dystrophy 2 | 602668 |
| SCA10 | Spinocerebellar ataxia 10 | 603516 |
| SPD1 | Synpolydactyly | 186000 |
| OPMD | Oculopharyngeal muscular dystrophy | 164300 |
| CCD | Cleidocranial dysplasia | 119600 |
| HPE5 | Holoprosencephaly 5 | 609637 |
| HFG syndrome | Hand-Foot-Genital syndrome | 140000 |
| BPES | Blepharophimosis, epicanthus inversus, and ptosis | 110100 |
| EIEE1 | Epileptic encephalopathy, early infantile, 1 | 308350 |
| FRAXA | Fragile X syndrome | 300624 |
| FXTAS | X tremor/ataxia syndrome | 300623 |
| FRAXE | Mental retardation, X-linked, associated with fragile site FRAXE | 309548 |

TABLE 7

| DISEASE or DISORDER (acronym or abbreviation) | GENE Name of the protein encoded by the gene | MIM number (*) | Gene ID of the sequence (§) |
|---|---|---|---|
| DM1 | DMPK (dystrophia myotonia protein kinase) | 605377 | 1762 |
| SCA8 | ATXN8; protein-coding strand | 613289 | 724066 |
| SCA8 | ATXN8; non-protein coding strand (ATXN8OS) | 603680 | 6315 |
| SCA12 | PPP2R2B (regulatory subunit B of protein phosphatase 2) | 604325 | 5521 |
| HDL2 | JPH3 (junctophilin-3) | 605268 | 57338 |
| SBMA | AR (androgen receptor) | 313700 | 367 |
| HD | HTT (huntingtin) | 613004 | 3064 |
| DRPLA | ATN1 (atrophin 1) | 607462 | 1822 |
| SCA1 | ATXN1 (ataxin-1) | 601556 | 6310 |
| SCA2 | ATXN2 (ataxin-2) | 601517 | 6311 |
| SCA3 | ATXN3 (ataxin-3) | 607047 | 4287 |
| SCA6 | CACNA1A (calcium channel, voltage-dependent, P/Q type, alpha 1A subunit) | 601011 | 773 |
| SCA7 | ATXN7 (ataxin-7) | 607640 | 6314 |
| SCA17 | TBP (TATA box-binding protein) | 600075 | 6908 |
| PSACH | COMP | 600310 | 1311 |
| DM2 | ZNF9 (zinc-finger protein) | 116955 | 7555 |
| SCA10 | ATXN10 (ataxin-10) | 611150 | 25814 |
| SPD1 | HOXD13 (homeobox D13) | 142989 | 3239 |
| OPMD | PABN1 (poly(A)-binding protein-2) | 602279 | 8106 |
| CCD | RUNX2 (runt-related transcription factor 2) | 600211 | 860 |
| HPE5 | ZIC2 (zinc-finger protein of cerebellum 2) | 603073 | 7546 |
| HFG syndrome | HOXA13 (homeobox A13) | 142959 | 3209 |
| BPES | FOXL2 | 605597 | 668 |
| EIEE1 | ARX (homeobox gene) | 300382 | 170302 |
| FRAXA | FMR1 (fragile X mental retardation 1) | 309550 | 2332 |
| FXTAS | FMR1 (fragile X mental retardation 1) | 309550 | 2332 |
| FRAXE | AFF2 | 300806 | 309548 |

TABLE 8

| DISEASE or DISORDER | REPEAT UNIT 5'-3' | Complementary strand 5'-3' | Coding = C [encoded amino acids] Non-Coding = NC | Normal average range of repeat units |
|---|---|---|---|---|
| DM1 | (CTG)n | (CAG)n | NC | 5-37 |
| SCA8 (non-protein coding strand, ATXN8OS) | (CTG)n | (CAG)n | NC | 15-50 |
| SCA8 (ATXN8-coding strand) | (CAG)n | (CTG)n | C [polyGln] | |
| SCA12 | (CAG)n | (CTG)n | NC | 7-32 |
| HDL2 | (CAG)n | (CTG)n | NC | 6-28 |
| SBMA | (CAG)n | (CTG)n | C [polyGln] | 10-36 |
| HD | (CAG)n | (CTG)n | C [polyGln] | 9-36 |
| DRPLA | (CAG)n | (CTG)n | C [polyGln] | 7-25 |
| SCA1 | (CAG)n | (CTG)n | C [polyGln] | 6-39 |
| SCA2 | (CAG)n | (CTG)n | C [polyGln] | 13-31 |
| SCA3 | (CAG)n | (CTG)n | C [polyGln] | 13-44 |
| SCA6 | (CAG)n | (CTG)n | C [polyGln] | 4-18 |
| SCA7 | (CAG)n | (CTG)n | C [polyGln] | 4-35 |
| SCA17 | (CAG)n | (CTG)n | C [polyGln] | 25-44 |
| SCA17 | (CAA)n | (TTG)n | C [polyGln] | 25-44 |
| PSACH | (GAC)n | (GTC)n | C [polyAsp] | 5 |
| DM2 | (CCTG)n | (CAGG)n | NC | ≤30 |
| SCA10 | (ATTCT)n | (AGAAT)n | NC | 10-29 |
| SPD1 | (GCG)n | (CGC)n | C [polyAla] | 15 |
| OPMD | (GCG)n | (CGC)n | C [polyAla] | 6 |
| CCD | (GCG)n | (CGC)n | C [polyAla] | 17 |
| HPE5 | (GCG)n | (CGC)n | C [polyAla] | 15 |
| HFG syndrome | (GCG)n | (CGC)n | C [polyAla] | 18 |
| BPES | (GCG)n | (CGC)n | C [polyAla] | 14 |
| EIEE1 | (GCG)n | (CGC)n | C [polyAla] | 10-16 |
| FRAXA | (CGG)n | (GCG)n | NC | 6-52 |
| FXTAS | (CGG)n | (GCG)n | NC | 6-52 |
| FRAXE | (CCG)n | (CGG)n | NC | 4-39 |

(*) MIM number of the Online Mendelian Inheritance in Man ® (OMIM ®) database. OMIM ® is authored and edited at the McKusick-Nathans Institute of Genetic Medicine, Johns Hopkins University School of Medicine, U.S.A., under the direction of Dr. Ada Hamosh; please see http://www.omim.org/ as well as McKusick, V. A. 1998 (Mendelian Inheritance in Man; A Catalog of Human Genes and Genetic Disorders, Baltimore, Maryland, U.S.A., Johns Hopkins University Press, ISBN 0-8018-5742-2).

(§) Gene ID as available from NCBI (National Center for Biotechnology Information, U.S. National Library of Medicine, 8600 Rockville Pike, Bethesda Md., 20894, U.S.A.) [http://www.ncbi.nlm.nih.gov/].

According to an aspect of the application, the DNA nucleic acid, to which the DNA-binding polypeptide of the application binds, or specifically binds, is a gene, more particularly the human gene, coding for DMPK, ATXN8, PPP2R2B, JPH3, AR, HTT, ATN1, ATXN1, ATXN2, ATXN3, CACNA1A, ATXN7, TBP, COMP, ZNF9, ATXN10, HOXD13, PABN1, RUNX2, ZIC2, HOXA13, FOXL2, ARX, FMR1 or AFF2 (wherein said gene comprises said at least one DNA tandem repeat).

According to an aspect of the application, said DNA nucleic acid is a gene, more particularly the human gene, coding for DMPK, ATXN8, PPP2R2B, JPH3, AR, HTT, ATN1, ATXN1, ATXN2, ATXN3, CACNA1A, ATXN7, TBP, COMP, ZNF9 or ATXN10 (wherein said gene comprises said at least one DNA tandem repeat).

More particularly, said DNA nucleic acid can be a gene, more particularly the human gene, coding for DMPK (wherein said gene comprises said at least one DNA tandem repeat). According to an aspect of the application, the number of DNA tandem repeat units contained in said human DNA nucleic acid is above the average normal range, e.g., above the range that is observed in a healthy subject, e.g., above the average normal range of repeat units respectively indicated in Table 8 above (i.e., above 37 for the DM1 disease or disorder, above 50 for the SCA8 disease or disorder, above 32 for the SCA12 disease or disorder, etc.).

The DNA-binding polypeptide of the application can be bound to said DNA nucleic acid. More particularly, the DNA-binding polypeptide of the application can be bound to said DNA nucleic acid in vitro or in an in vitro cell.

The DNA-binding polypeptide of the application can be directly or indirectly linked to at least one endonuclease monomer, or to at least one fragment of endonuclease monomer, wherein said fragment of endonuclease monomer still comprises the catalytic domain of said endonuclease monomer.

More particularly, the DNA-binding polypeptide of the application can be directly or indirectly linked to one endonuclease monomer, or one fragment of endonuclease monomer, wherein said fragment of endonuclease monomer still comprises the catalytic domain of said endonuclease monomer.

The linkage of said (at least) one endonuclease monomer or fragment thereof to said DNA-binding polypeptide is such that it does not impede the endonuclease activity or function of said at least one endonuclease monomer or at least fragment thereof.

The resulting structure can be viewed as and functions as a TALEN monomer.

In the application, the phrase "endonuclease" and the phrase "catalytic domain" (or equivalent or similar phrases) are given their respective ordinary meaning in the field of enzymology, more particularly in the field of enzymology for biotechnological applications. An endonuclease can e.g., be defined as an enzyme that cleaves phosphodiester bond(s) within polynucleotide chain(s). The catalytic domain of an endonuclease can e.g., be defined as the region of said endonuclease, which contains the catalytic function of the endonuclease.

In the application, the phrase "catalytic domain" (or an equivalent or similar phrase) can be understood as meaning "cleavage domain", i.e., the portion of the endonuclease, which causes the cleavage of the polynucleotide chain(s).

In the application, the phrase "linked" (or an equivalent or similar phrase) encompasses direct linkage, as well as indirect linkage. It encompasses any chemical linkage, more particularly covalent linkage, more particularly divalent covalent linkage.

Appropriate endonucleases notably comprise endonucleases, which function as multimers, more particularly as dimers.

A dimeric endonuclease is an endonuclease, which is formed by two monomers, the dimerization of which is required to cleave the target DNA double strand. Each monomer of a dimeric endonuclease comprises a catalytic domain.

Examples of such dimeric endonucleases notably include the FokI endonuclease (Christian et al. 2010, Li et al. 2011, WO 94/18313 and its national counterparts more particularly its US counterpart(s), including the US continuation and divisional application(s)), WO 95/09233 and its national counterparts more particularly its US counterpart(s), including the US continuation and divisional application(s)). An example of the sequence of a FokI endonuclease and of its catalytic domain is available under GENBANK accession number A32861. When the endonuclease is a multimeric endonuclease, more particularly a dimeric endonuclease, the DNA-binding polypeptide of the application is advantageously linked to only one of said endonuclease monomers (advantageously in only one exemplar).

Appropriate endonucleases also comprise monomeric endonucleases. A monomeric endonuclease cleaves DNA, when it is used as single monomer as well as when it is used in a pair of monomeric endonucleases. Examples of monomeric endonucleases include I-TevI, which is the homing endonuclease member of the GIY-YIG protein family. Examples of fragments of I-TevI, which still comprise the endonuclease catalytic domain, include the I-TevI fragment, which consists of the N-terminal 183 residues of wild-type I-TevI and a linker of 5 amino acids, e.g., the linker QGPSG [SEQ ID NO: 22] (Beurdeley et al. 2013). When the endonuclease is a monomeric endonuclease, the DNA-binding polypeptide of the application is advantageously linked to said endonuclease monomer in only one exemplar.

Examples of endonucleases also include non-naturally occurring endonuclease, e.g., a non-naturally occurring endonuclease, which derives from a naturally-occurring endonuclease, more particularly from a naturally-occurring dimeric endonuclease, by amino acid mutation(s) (e.g., by amino acid replacement(s) and/or deletion(s) and/or addition(s), more particularly by amino acid replacement(s)). For example, said non-naturally occurring restriction endonuclease can be a (homo- or hetero-) dimer, which differs from the FokI dimer by amino acid mutation(s) in the catalytic domain of one or each of the two FokI monomers. The number of amino acid mutation(s) per mutated FokI monomer can e.g., be of three to six. For example, said amino acid mutation(s) can be three to six mutations selected from positions 483, 486, 487, 490, 499 and 538 of the catalytic domain as described in cf. WO 2012/015938 and its national counterparts, including its US national counterpart(s).

Advantageously, the DNA-binding polypeptide of the application is linked to only one endonuclease monomer (advantageously at only one exemplar).

In the application, the phrase "an endonuclease monomer" (or an equivalent or a similar phrase) encompasses a monomer of a dimeric endonuclease, as well as the monomer of a monomeric endonuclease.

For medical applications, more particularly for applications relating to treatment and/or palliation and/or prevention of diseases or disorders, a dimeric endonuclease might be preferred to a pair of monomeric endonucleases, because a monomeric endonuclease might induce off-target single-strand cleavage.

According to an embodiment of the application, the endonuclease is a dimeric (naturally-occurring or non naturally-occurring) endonuclease, such as FokI.

A fragment from an endonuclease monomer, which still comprises the catalytic domain of the endonuclease monomer, can also be used.

Said fragment can be a fragment of a monomer of a dimeric endonuclease, or a fragment of a monomeric endonuclease (said endonuclease being naturally-occurring or non-naturally-occurring).

An example of a FokI endonuclease monomer is the sequence of SEQ ID NO: 49 (cf. example 1 below).

Examples of a DNA-binding polypeptide of the application, which is directly or indirectly linked to an endonuclease monomer or to a fragment of endonuclease monomer, and which (specifically) binds to a non-overlapping DNA target site (i.e., the DNA target site of SEQ ID NO: 10) include:

the polypeptide coded by the sequence of SEQ ID NO: 39, and the polypeptide coded by plasmid pCLS9996exp (C.N.C.M. deposit number I-4804).

Examples of a DNA-binding polypeptide of the application, which is directly or indirectly linked to an endonuclease monomer or to a fragment of endonuclease monomer, and which (specifically) binds to an overlapping DNA target site (i.e., the DNA target site of SEQ ID NO: 4), include:

the polypeptide coded by the sequence of SEQ ID NO: 50, and the polypeptide coded by plasmid pCLS16715 (C.N.C.M. deposit number I-4805).

A DNA-binding polypeptide of the application may further comprise a detection label or a selection marker, such as kanamycin or a knockout leucine synthesis gene (e.g., LEU2) (cf. example 1 below).

The application also relates to a set comprising a first DNA-binding polypeptide and a second DNA-binding polypeptide, wherein only one, or each one, of said first and second DNA-binding polypeptides is a DNA-binding polypeptide of the application. Said first DNA-binding polypeptide is different from said second DNA-binding polypeptide. Said set can be herein referred to as the "polypeptide set of the application".

A polypeptide set of the application is:

a set comprising a first DNA-binding polypeptide and a second DNA-binding polypeptide, wherein said first DNA-binding polypeptide is a DNA-binding polypeptide of the application and wherein said second DNA-binding polypeptide is a DNA-binding polypeptide of the application; or a set comprising a first DNA-binding polypeptide and a second DNA-binding polypeptide, wherein said first DNA-binding polypeptide is a DNA-binding polypeptide of the application and wherein said second DNA-binding polypeptide is not a DNA-binding polypeptide of the application (said set may herein after be more particularly referred to as "a mixed polypeptide set of the application").

The phrase "set" is intended in accordance with its ordinary meaning in the field. It notably encompasses the meaning of "a plurality of", more particularly the meaning of "a pair of". Said set of plurality (or pair) can e.g., be in the form of one composition or kit, or of at least two compositions or at least two kits.

Said one composition or kit comprises both said first and second DNA-binding polypeptides. Said at least two compositions or kits are in the form of separate compositions or kits, each comprising one of said first and second DNA-binding polypeptides (e.g., a first composition or kit comprising said first DNA-binding polypeptide and a second composition or kit comprising said second DNA-binding polypeptide, wherein said first composition or kit is distinct or separate from said second composition or kit). Said at least two compositions or kits can be for simultaneous, separate, distinct or sequential use, more particularly for simultaneous or sequential use.

In said polypeptide set, the first and second DNA-binding polypeptides can e.g., be present as isolated polypeptides, as individual polypeptides, as dimerized polypeptides, or can be contained within cell(s), e.g., within host and/or genetically engineered cell(s) (e.g., as described below) (the first DNA-binding polypeptide can be contained within the same cell as said second DNA-binding polypeptide, or in two distinct cells respectively).

According to an aspect of the application, the first DNA-binding polypeptide and the second DNA-binding polypeptide, which are comprised in said set, are different from each other.

According to an aspect of the application, said first and second DNA-binding polypeptides (specifically) bind to the same DNA nucleic acid but at different DNA target sites.

More particularly, said first and second DNA-binding polypeptides (specifically) bind to the same double-stranded DNA nucleic acid, wherein said first DNA-binding polypeptide binds to one strand of said double-stranded DNA nucleic acid, and wherein said second DNA-binding polypeptide binds to the other strand of said double-stranded DNA nucleic acid (i.e., to the complementary strand). Hence, said first DNA-polypeptide recognizes or binds to a first DNA target site, said second DNA-polypeptide recognizes or binds to a second DNA target site, wherein said first DNA target site is comprised in a strand of a double-stranded nucleic acid and said second DNA target site is comprised in the other (complementary) strand of the same double-stranded DNA nucleic acid.

Advantageously, said first DNA target site is different from said second DNA target site. Advantageously, said first DNA target site is comprised in a first strand of a double-stranded DNA nucleic acid, without being comprised in the second strand of the same double-stranded DNA nucleic acid, and, conversely, said second DNA target site is comprised in said second strand (of the same double-stranded DNA nucleic acid as said first DNA target site), without being comprised in said first strand.

The application thus relates to a composition or kit comprising a first DNA-binding polypeptide and a second DNA-binding polypeptide, wherein said first DNA-binding polypeptide is different from said second DNA-binding polypeptide, wherein each of said first and second DNA-binding polypeptides binds to a DNA nucleic acid comprising at least one DNA tandem repeat, wherein the DNA nucleic acid to which said first DNA-binding polypeptide binds is one strand of a double-stranded nucleic acid, wherein the DNA nucleic acid to which said second DNA-binding polypeptide binds is the other strand of the same double-stranded nucleic acid, wherein said double-stranded DNA nucleic acid is a gene involved in a neurological and/or muscular and/or skeletal disorder or disease involving said at least one DNA tandem repeat, wherein each of said first and second DNA-binding polypeptides comprises a TAL effector tandem repeat consisting of adjacent units of TAL effector tandem repeat, wherein the ordered series of RVDs formed by the RVDs respectively contained in said adjacent units of TAL effector tandem repeat, in N- to C-orientation, is an ordered series of amino acids, which determines the recognition of the 5'-3' nucleotide sequence of a DNA target site contained in the strand of double-stranded DNA nucleic acid to which said DNA-binding polypeptide binds, wherein the sequence of said DNA target site is:

i. a fragment of said strand of double-stranded DNA nucleic acid consisting of a fragment of said at least one DNA tandem repeat, wherein said fragment comprises more than one copy of said DNA sequence unit of said at least one DNA tandem repeat, or ii. a fragment of said strand of double-stranded DNA nucleic acid, which starts outside the sequence of said at least one DNA tandem repeat and ends within the sequence of said at least one DNA tandem repeat, or conversely, which starts within the sequence of said at least one DNA tandem repeat and ends outside the sequence of said at least one DNA tandem repeat, wherein each of said first and second DNA-binding polypeptides is directly or indirectly linked to one endonuclease monomer or to one fragment of endonuclease monomer, wherein said fragment of endonuclease monomer still comprises the catalytic domain of said endonuclease monomer, and wherein said first and second DNA-binding polypeptides induce a partial or complete deletion of said at least one DNA tandem repeat.

Advantageously, said endonuclease monomer is the monomer of a dimeric endonuclease.

According to an aspect of the application, the DNA target site is a non-overlapping DNA target site (as defined above) for only one of said first and second DNA-binding polypeptides, or for each of said first and second DNA-binding polypeptides. When the DNA target site is a non-overlapping DNA target site (as defined above) for only one of said first and second DNA-binding polypeptides, the DNA target site of the other of said first and second DNA-binding polypeptides is:

an overlapping DNA target site (as above-defined), or is a DNA target site, which is neither a non-overlapping site (as above-defined) nor an overlapping site (as above-defined).

According to an aspect of the application, the DNA target site is an overlapping DNA target site (as defined above) for only one of said first and second DNA-binding polypeptides, or for each of said first and second DNA-binding polypeptides. When the DNA target site is an overlapping DNA target site (as defined above) for only one of said first and second DNA-binding polypeptides, the DNA target site of the other of said first and second DNA-binding polypeptides is:

a non-overlapping DNA target site (as above-defined), or is a DNA target site, which is neither a non-overlapping site (as above-defined) nor an overlapping site (as above-defined).

Advantageously, the DNA target site is an overlapping DNA target site (as defined above) for one of said first and second DNA-binding polypeptides.

Advantageously, the DNA target site is a non-overlapping DNA target site (as defined above) for one of said first and second DNA-binding polypeptides.

Advantageously, the DNA target site is an overlapping DNA target site (as defined above) for one of said first and second DNA-binding polypeptides and is a non-overlapping DNA target site (as defined above) for the other of said first and second DNA-binding polypeptides.

This configuration drastically reduces the chance that the first and second DNA-binding polypeptides induce a length alteration or mutation at an off-target location, e.g., in a non-pathological gene, which would comprise the same DNA repeat unit as the targeted pathological gene.

For example, said first DNA-binding polypeptide binds to a DNA target site of SEQ ID NO: 10 and said second DNA-binding polypeptide binds to a DNA target site of SEQ ID NO: 4, or said first DNA-binding polypeptide binds to a DNA target site of SEQ ID NO: 11 and said second DNA-binding polypeptide binds to a DNA target site of SEQ ID NO: 5 (cf. FIG. 1B). For example, the ordered series of RVDs formed by the adjacent units forming the TAL effector tandem repeat of said first DNA-binding polypeptide is NN; HD; NG; NN; HD; NG; NN; HD; NG; NN; HD; NG; NN; HD; NG, which determines the (specific) recognition (and the (specific) binding to) the non-overlapping DNA target site of SEQ ID NO: 10), and the ordered series of RVDs formed by the adjacent units forming the TAL effector tandem repeat of said second DNA-binding polypeptide is NN; NG; NN; NI; NG; HD; HD; HD; HD; HD; HD; NI; NN; HD; NI, which determines the (specific) recognition (and the (specific) binding to) the overlapping DNA target site of SEQ ID NO: 4.

More particularly, the TAL effector tandem repeat of said first DNA-binding polypeptide is different from the one of said second DNA-binding polypeptide. The difference can be a difference in amino acid sequence and/or in amino acid length.

More particularly:

the frame sequence(s) of the TAL effector tandem repeat units of said first DNA-binding polypeptide is(are) different from the one(s) of said second DNA-binding polypeptide; and/or said first DNA-binding polypeptide and said second DNA-binding polypeptide have different DNA target sites, i.e., the ordered series of RVDs formed by the units of the TAL effector tandem repeat that is contained in said first DNA-binding polypeptide is different from the ordered series of RVDs formed by the units of the TAL effector tandem repeat that is contained in said second DNA-binding polypeptide.

For example:

the adjacent units of the TAL effector tandem repeat that is contained in said first DNA-binding polypeptide may comprise one or several copy(ies) of at least one sequence selected from the group consisting of SEQ ID NOs: 25, 26, 46, 55 and said variants thereof, the adjacent units of the TAL effector tandem repeat that is contained in said second DNA-binding polypeptide may comprise one or several copy(ies) of at least one sequence selected from the group consisting of SEQ ID NOs: 25, 26, 46, 55 and said variants thereof, and the ordered series of RVDs formed by the RVDs respectively contained in the adjacent units of the TAL effector tandem repeat of said first DNA-binding polypeptide, in N- to C-orientation, is different from the ordered series of RVDs formed by the RVDs respectively contained in the adjacent units of the TAL effector tandem repeat of said second DNA-binding polypeptide, in N- to C-orientation.

For example, the ordered series of RVDs formed by the RVDs respectively contained in the adjacent units of the TAL effector tandem repeat of said first DNA-binding polypeptide, in N- to C-orientation, determines the recognition of (and the (specific) binding to) an overlapping DNA target site (as defined above, e.g., the DNA target site of SEQ ID NO: 4 or 5, more particularly the DNA target site of SEQ ID NO: 4), and the ordered series of RVDs formed by the RVDs respectively contained in the adjacent units of the TAL effector tandem repeat of said second DNA-binding polypeptide, in N- to C-orientation, determines the recognition of (and the (specific) binding to) a non-overlapping DNA target site (as defined above, e.g., the DNA target site of SEQ ID NO: 10 or 11, more particularly the DNA target site of SEQ ID NO: 10; cf. FIG. 1B).

Each of said first and second DNA-binding polypeptides can be linked to an endonuclease monomer or to a fragment of such a monomer as described above.

Advantageously, each of said first and second DNA-binding polypeptides is linked to the monomer of a dimeric endonuclease, such as Fok I, or to a fragment of such a monomer as described above (cf. above).

In a polypeptide set of the application, said first DNA-binding polypeptide can be dimerized to said second DNA-binding polypeptide.

The application thus relates to a polymer, more particularly a dimer, which comprises said first and second DNA-binding polypeptides. Said polymer may further comprise at least one (double-stranded) DNA nucleic acid, more particularly at least one (double-stranded) DNA nucleic acid comprising at least one DNA tandem repeat (as defined above). Said at least one DNA nucleic acid can be linked to said first and second DNA-binding polypeptides by non-covalent linkage, e.g., by non-covalent binding of the RVDs of said first and second DNA-binding polypeptides to nucleotides of said at least one DNA nucleic acid, e.g., by non-covalent binding of the RVDs of said first DNA-binding polypeptide to nucleotides of one strand of said at least one double-stranded DNA nucleic acid and by non-covalent binding of the RVDs of said second DNA-binding polypeptide to nucleotides of the other (complementary) strand of the same double-stranded DNA nucleic acid.

Alternatively, in a polypeptide set of the application, said first DNA-binding polypeptide can be not dimerized to said second DNA-binding polypeptide.

More particularly, in a set of the application, said first DNA-binding polypeptide can be contained separately from said second DNA-binding polypeptide, e.g., to avoid dimerization of said first DNA-binding polypeptide to said second DNA-binding polypeptide.

The nucleotide length that extends from the DNA target site of said first DNA-binding polypeptide to the DNA target site of said second DNA-polypeptide is being referred to as the "spacer length". This terminology is in accordance with the terminology that is used in the field of TALENs.

Said spacer length is the number of nucleotides extending between the two proximal ends of the respective DNA target sites of said first and second DNA-binding polypeptides.

On a double-stranded DNA nucleic acid, wherein a first DNA-binding polypeptide recognizes or binds to a first DNA target site on one strand of said double-stranded DNA nucleic acid and wherein a second DNA-binding polypeptide recognizes or binds to a second DNA target site on the other strand of said double-stranded DNA nucleic acid, said spacer length can be viewed as the nucleotide length that extends from the 3' end of one of the respective DNA target sites of said first and second DNA-binding polypeptides to the 3' end of the other of said DNA target sites (the last 3' end nucleotides of said first and second DNA target sites are not taken into account in the computation of said nucleotide number).

For example, in FIG. 1B, the sequence of the spacer is GCAGCAGCAGCAGCAGCAGC [SEQ ID NO: 8] (GCTGCTGCTGCTGCTGCTGC [SEQ ID NO: 9] on the complementary strand (5'-3')). Hence, in FIG. 1B, the spacer length is 20 nucleotides.

When each of the first and second DNA-binding polypeptides are respectively linked to the monomer of the same dimeric endonuclease, said spacer length is selected to be sufficiently short and sufficiently long for the two monomers of said dimeric endonuclease to dimerize when said first and second DNA-binding polypeptides are bound to their respective DNA target sites on each strand of the same double-stranded DNA nucleic acid (cf. FIGS. 1A and 1B). In other words, the respective DNA target sites of said first and second DNA-binding polypeptides are selected to be spaced apart by a spacer length that is appropriate for dimerization of the two endonuclease monomers respectively borne by said first and second DNA-binding polypeptides.

The respective DNA target sites of said first and second DNA-polypeptides can be spaced apart by a nucleotide length that may vary from 6 to 40 nt (or bp), optimal cleavage being usually observed with a spacer length of 10 to 30 nt (or bp), e.g., of 15-24 nt (or bp), 15-21 nt (or bp) or 16-21 nt (or bp), e.g., 16, 17, 18, 19, 20 or 21 nt (or bp).

Advantageously:
said DNA target site is an overlapping DNA target site (as defined above) for one of said first and second DNA-binding polypeptides, and is a non-overlapping DNA target site (as defined above) for the other of said first and second DNA-binding polypeptides, and
each of said first and second DNA-binding polypeptides is linked to the monomer of a dimeric endonuclease (cf. above), such as Fok I, or to a fragment of such a monomer as described above.

Advantageously:
said DNA target site is an overlapping DNA target site (as defined above) for one of said first and second DNA-binding polypeptides, and is a non-overlapping DNA target site (as defined above) for the other of said first and second DNA-binding polypeptides,
each of said first and second DNA-binding polypeptides is linked to the monomer of a dimeric endonuclease (cf. above), such as Fok I, or to a fragment of such a monomer as described above, and
the DNA target site of said first DNA-binding polypeptide is spaced apart from the one of said second DNA-binding polypeptide by a spacer length that enables dimerization of the two endonuclease monomers respectively borne by said first and second DNA-binding polypeptides (when said first and second DNA-binding polypeptides are bound to their respective DNA target sites), e.g., by a spacer length as indicated above e.g., a spacer length of 15-24 nt (or bp), 15-21 nt (or bp) or 16-21 nt (or bp), e.g., 16, 17, 18, 19, 20 or 21 nt (or bp).

In a set, which comprises a first DNA-binding polypeptide, which is a DNA-binding polypeptide of the application and which further comprises a second DNA-binding polypeptide, which is not a DNA-binding polypeptide of the application, i.e., in a mixed polypeptide set of the application, said second DNA-binding polypeptide, which is not of the application, can e.g., be as above-defined except that its DNA target site is neither a non-overlapping DNA target site as defined above nor an overlapping DNA target site as defined above.

Said second DNA-binding polypeptide, which is not of the application, can e.g., be identical to a DNA-polypeptide of the application in all features (e.g., it comprises a TAL effector tandem repeat as above-defined), except for the DNA target site, which is not one that is recognized by a DNA-binding polypeptide of the application.

Hence, said second DNA-binding polypeptide, which is not of the application, can e.g., be identical to a DNA-polypeptide of the application in all features (e.g., it comprises a TAL effector tandem repeat as above-defined), except that the ordered series of RVDs formed by the RVDs respectively contained in the adjacent units of its TAL effector tandem repeat, in N- to C-orientation, is an ordered series of amino acids, which according to the RVD/nucleotide correspondence shown in Table 5 above, determines the recognition of the 5'-3' nucleotide sequence of a DNA target site that is contained in a DNA nucleic acid, wherein said DNA nucleic acid is as above-defined, but wherein said DNA target site is neither a non-overlapping DNA target site as defined above nor an overlapping DNA target site as defined above. More particularly, the DNA target site of said second DNA-binding polypeptide, which is not of the application, can be a fragment of said DNA nucleic, which does not comprise any fragment of said at least one DNA tandem repeat, more particularly a fragment of said DNA nucleic, which does not comprise any DNA sequence unit of said at least one DNA tandem repeat.

Said first DNA-binding polypeptide, which is comprised in the set with said second DNA-binding polypeptide, is a DNA-binding polypeptide of the application, and therefore has a DNA target site, which is either a non-overlapping DNA target site as above-defined or an overlapping DNA binding site as above defined.

The spacer length is as above-defined. More particularly, the spacer length between said first DNA-binding polypeptide of the application and said second DNA-binding polypeptide (which is not of the application) is a nucleotide length appropriate for dimerization of the two endonuclease monomers respectively borne by said first and second DNA-binding polypeptides of the application. The respective DNA target sites of said first and second DNA-polypeptides can be spaced apart by a nucleotide length that may vary from 6 to 40 nt (or bp), optimal cleavage being usually observed with a spacer length of 10 to 30 nt (or bp), e.g., of 15-24 nt (or bp), 15-21 nt (or bp) or 16-21 nt (or bp), e.g., 16, 17, 18, 19, 20 or 21 nt (or bp). According to an aspect of the application, said first and second DNA-binding polypeptides induce a double-strand break in said double-stranded DNA nucleic acid. More particularly, they induce a double-strand break specifically in said double-stranded DNA nucleic acid.

The application also relates to a nucleic acid, more particularly a DNA or RNA, more particularly a DNA. Said nucleic acid can be a man-made or artificial or engineered nucleic acid.

A nucleic acid of the application codes for the DNA-binding polypeptide of the application, more particularly for the DNA-binding polypeptide of the application (directly or indirectly) linked to (at least) one endonuclease monomer (cf. above) or to (at least) one fragment of endonuclease monomer as above-defined.

The application relates more particularly to a coding nucleic acid, the coding sequence of which consists of a sequence coding for the DNA-binding polypeptide of the application, more particularly for the DNA-binding polypeptide of the application (directly or indirectly) linked to (at least) one endonuclease monomer (cf. above) or to (at least) one fragment of endonuclease monomer as above-defined (said coding being according to the universal genetic code, taking due account of its degeneracy).

The application relates more particularly to a coding nucleic acid, the coding sequence of which comprises a sequence, which codes for the TAL effector tandem repeat of a DNA-binding polypeptide of the application (said coding being according to the universal genetic code, taking due account of its degeneracy). Said coding sequence may e.g., comprise one or several copy(ies) of at least one of the sequences coding for SEQ ID NO: 25, 26, 46, 55 and said variant sequences thereof.

Examples of such coding nucleic acid sequences comprise:
the nucleic acid sequence of SEQ ID NO: 45, which consists of 10 copies of a sequence coding for SEQ ID NO: 46 and of 5 copies of a sequence coding for SEQ ID NO: 25, and which codes for a TAL effector tandem repeat, wherein the ordered series of RVDs (i.e., NN; HD; NG; NN; HD; NG; NN; HD; NG; NN; HD; NG; NN; HD; NG) determine the (specific) recognition of (and the (specific) binding to) the non-overlapping DNA target site of SEQ ID NO: 10), the portion of the nucleic acid sequence of the insert carried by plasmid pCLS9996exp (C.N.C.M. deposit number I-4804), which codes for a TAL effector tandem repeat (said TAL effector tandem repeat (specifically) binds to the non-overlapping DNA target site of SEQ ID NO: 10), the nucleic acid sequence of SEQ ID NO: 54, which consists of 5 copies of a sequence coding for SEQ ID NO: 46, 2 copies of a sequence coding for SEQ ID NO: 55 and of 8 copies of a sequence coding for SEQ ID NO: 25, and which codes for a TAL effector tandem repeat, wherein the ordered series of RVDs (i.e., NN; NG; NN; NI; NG; HD; HD; HD; HD; HD; HD; NI; NN; HD; NI) determine the (specific) recognition of (and the (specific) binding to) the overlapping DNA target site of SEQ ID NO: 4), the portion of the nucleic acid sequence of the insert carried by plasmid pCLS16715 (C.N.C.M. deposit number I-4805), which codes for a TAL effector tandem repeat (said TAL effector tandem repeat (specifically) binds to the overlapping DNA target site of SEQ ID NO: 4).

The application more particularly relates to a nucleic acid (DNA or RNA), which codes for the TAL effector tandem repeat coded by plasmid pCLS9996exp (C.N.C.M. deposit number I-4804) or by plasmid pCLS16715 (C.N.C.M. I-4805).

Examples of sequences coding for an endonuclease monomer or for a fragment of endonuclease monomer as above-defined comprise:
the sequence of SEQ ID NO: 3 (which codes for the FokI monomer of SEQ ID NO: 49) and the fragments thereof, which still code for the FokI catalytic domain, and the sequences coding for the I-TevI endonuclease and the fragments thereof, which still code for the I-TevI catalytic domain.

The nucleic acid of the application may comprise at least one coding sequence, wherein said at least one coding sequence codes for (at least) one DNA-binding polypeptide of the application (directly or indirectly) linked to (at least) one endonuclease monomer (cf. above) or to (at least) one fragment of endonuclease monomer as above-defined (according to the universal genetic code and taking due account of its degeneracy). Examples of such coding nucleic acid sequences comprise:
the nucleic acid sequence of SEQ ID NO: 39 (which codes for a TALEN, which (specifically) binds to the non-overlapping DNA target site of SEQ ID NO: 10), the nucleic acid sequence of the insert carried by plasmid pCLS9996exp (C.N.C.M. deposit number I-4804), which codes for a TALEN that (specifically) binds to the non-overlapping DNA target site of SEQ ID NO: 10), the nucleic acid sequence of SEQ ID NO: 50 (which codes for a TALEN, which (specifically) binds to the overlapping DNA target site of SEQ ID NO: 4), the nucleic acid sequence of the insert carried by plasmid pCLS16715 (C.N.C.M. deposit number I-4805), which codes for a TALEN that (specifically) binds to the overlapping DNA target site of SEQ ID NO: 4).

The nucleic acid of the application can further comprise a translational start codon, such as ATG, located (immediately) in 5' of said coding sequence and/or further comprise a 3'UTR for transcription termination and polyadenylation of RNA transcript located (immediately) in 3' of said coding sequence. For example, said 3' UTR comprises a translational stop codon (such as TGA, TAG or TAA) and a polyA sequence.

The nucleic acid of the application may further comprise sequence(s), which does(do) not code for amino acid(s) but which regulates(regulate) transcription and/or translation. For example, the nucleic acid of the application can further comprise (at least) one sequence for initiating DNA transcription located in 5' of said coding sequence and/or further comprise (at least) one sequence for terminating DNA transcription located in 3' of said coding sequence. For example, the nucleic acid of the application may further comprise (at least) one enhancer (such as the GAL10 enhancer of SEQ ID NO: 37) and a promoter (such as the CYC1 promoter of SEQ ID NO: 38) in 5' of said coding sequence, and may further comprise a terminator (such as an ADH1 terminator of SEQ ID NO: 40 or 51).

The nucleic acid of the application, can (thereby) form an expression cassette for expression in a host cell, more particularly in a eukaryotic host cell, more particularly in a mammalian cell, a non-human mammalian cell (e.g., a rodent cell, such as a mouse cell), a human host cell, a yeast host cell, a bacterial host cell or a plant host cell, more particularly in a human host cell or a yeast host cell, more particularly in a human host cell.

Hence, the nucleic acid of the application may consist of:
(at least) one sequence coding for a polypeptide consisting of the DNA-binding polypeptide of the application (according to the universal genetic code and taking due account of its degeneracy), or coding for a polypeptide consisting of the DNA-binding polypeptide of the application (directly or indirectly) linked to (at least) one endonuclease monomer (cf. above) or to (at least) one fragment of endonuclease monomer as above-defined (according to the universal genetic code and taking due account of its degeneracy), and
optionally, sequence(s), which does(do) not code for amino acids but which regulates(regulate) transcription and/or translation, such as (at least) one sequence for initiating DNA transcription located (immediately) in 5' of said nucleic acid sequence and/or (at least) one sequence for terminating DNA transcription located (immediately) in 3' of said nucleic acid sequence, e.g., as above described.

For example, the sequence of the nucleic acid of the application can comprise or consist of the sequence of SEQ ID NO: 2 or the sequence of SEQ ID NO: 1.

The sequence of SEQ ID NO: 2 codes for a DNA-binding polypeptide of the application, which is linked to a FokI endonuclease monomer and, which (specifically) binds to a DNA target site that is the (non-split) left TALE DNA-binding domain of FIG. 1B (cf. example 1 below). The sequence of the left-hand TALE DNA-binding domain of FIG. 1B is the sequence of SEQ ID NO: 4, i.e., an overlapping DNA target site as defined above.

The sequence of SEQ ID NO: 1 codes for a DNA-binding polypeptide of the application, which is linked to a FokI endonuclease monomer and, which (specifically) binds to a DNA target site that is the right TALE DNA-binding domain of FIG. 1B (cf. example 1 below). The sequence of the DNA target site of the right TALE DNA-binding domain of FIG. 1B is the sequence of SEQ ID NO: 10, i.e., a non-overlapping DNA target site as defined above.

For example, the sequence of the nucleic acid of the application can comprise or consist of the sequence of the insert carried by plasmid pCLS9996 (C.N.C.M. I-4804) or the sequence of the insert carried by plasmid pCLS16715 (C.N.C.M. I-4805).

The application also relates to a nucleic acid vector, more particularly a recombinant vector, more particularly a recombinant expression nucleic acid vector, which comprises at least one nucleic acid (DNA or RNA) of the application.

A nucleic acid vector of the application may comprise a cloning site into which a nucleic acid is inserted, wherein the sequence of said inserted nucleic acid is the sequence of the nucleic acid of the application.

The nucleic acid vector of the application advantageously is a non-integrative (i.e., a vector, which does not induce the integration of the nucleic acid into the genome of the host into which said vector has been introduced) and/or non-replicative.

According to an embodiment of the application, said nucleic acid vector is a recombinant expression vector. More particularly, said nucleic acid vector is an expression vector comprising a cloning site into which a nucleic acid to be expressed is inserted under the control of a 5' expression promoter (said promoter being inducible or non-inducible), and optionally under the control of at least one 5' expression enhancer, wherein the sequence of said nucleic acid to be expressed is the sequence of the nucleic acid of the application. Advantageously, said expression vector is a non-integrative vector, more particularly a vector for transient expression, for example a plasmid.

An illustrative plasmid is the plasmid pCLS16715 (C.N.C.M. I-4805), which carries the sequence of SEQ ID NO: 2 (as nucleic acid to be expressed): SEQ ID NO: 2 codes for the TALEN monomer that binds to the left-hand DNA target site of SEQ ID NO: 4; cf. FIG. 1B. Another illustrative plasmid is the plasmid pCLS9996exp (C.N.C.M. I-4804), which carries the sequence of SEQ ID NO: 1 (as nucleic acid to be expressed): SEQ ID NO: 1 codes for the TALEN monomer that binds to the right-hand DNA target site of SEQ ID NO: 10; cf. FIG. 1B.

Each of plasmid pCLS16715 and plasmid pCLS9996exp has been deposited at the Collection Nationale de Cultures de Microorganismes (C.N.C.M.) under the terms of the Budapest Treaty (COLLECTION NATIONALE DE CULTURES DE MICROORGANISMES; Institut Pasteur; 28, rue du Docteur Roux; F-75724 PARIS CEDEX 15; FRANCE).

The C.N.C.M. deposit number of plasmid pCLS16715 is I-4805 and the date of the deposit under the terms of the Budapest Treaty is 10 Oct. 2013. Deposit I-4805 is plasmid pCLS16715 transformed in *E. coli* (more particularly, an *E. coli* strain, which is deficient in the genes involved in the rearrangement and deletion of DNA, such as *E. coli* SURE®2, which is available from STRATEGENE, an AGILENT TECHNOLOGIES division, California, U.S.A.; e.g., an *E. coli* strain, which is endA1 glnV44 thi-1 gyrA96 relA1 lac recB recJ sbcC umuC::Tn5 uvrC e14-Δ(mcrCB-hsdSMR-mrr)171 F'[proAB⁺ lacI$^q$ lacZΔM15 Tn10 Amy Cm$^R$]). An example of suitable growth medium is Lysogeny Broth (LB) growth medium+ampicillin (e.g., ampicillin at 100 μg/mL). An example of suitable incubation condition is 37° C. (more particularly, 37° C. under stirring conditions).

The C.N.C.M. deposit number of plasmid pCLS9996exp is I-4804 and the date of the deposit under the terms of the Budapest Treaty is 10 Oct. 2013. Deposit I-4804 is plasmid pCLS9996 transformed in *E. coli* (more particularly, an *E. coli* strain, which is efficient in DNA transformation and in maintenance of large plasmids, such as *E. coli* DH10B (cf. Durfec et al. 2008, J. Bacteriol. 190(7): 2597-2606)). An example of suitable growth medium is Lysogeny Broth (LB) growth medium+kanamycin sulfate (e.g., kanamycin at 50 μg/mL). An example of suitable incubation condition is 37° C. (more particularly, 37° C. under stirring conditions).

Appropriate non-integrative vectors, more particularly appropriate vectors for transient expression, also comprise retroviral or lentiviral vectors, more particularly HIV vectors, more particularly HIV1 vectors, wherein the integrase of said vectors is or has been made defective, e.g., by class 1 integrase mutation(s) (whereby said vectors are or have been made non-integrative). Examples of such non-integrative vectors comprise:

- a HIV1 vector, the integrase of which has been made defective by replacement of the $^{262}$RRK motif by AAH as described in Philippe et al. 2006 (cf. FIG. 1 of Philippe et al. 2006),
- a retroviral or lentiviral vector, more particularly a HIV vector, more particularly a HIV1 vector, as described in WO 99/55892, which has been made non-integrative e.g., by the method described in Philippe et al. 2006 or by the method described in WO 2006/010834,
- a non-integrative vector as described in WO 2009/019612, more particularly at paragraph [0154] of WO 2009/019612.

The application more particularly relates to a recombinant vector, more particularly a recombinant expression vector, more particularly a recombinant retroviral expression vector, more particularly a lentiviral expression vector, which comprises:

at least one nucleic acid (DNA or RNA) of the application, more particularly at least one RNA of the application (and regulatory elements for the expression of said at least one nucleic acid or RNA), and a defective integrase, more particularly an integrase, which has been made defective by mutation(s), more particularly an integrase, which has been made defective by mutation(s), wherein said mutation(s) comprise(s) or consist(s) of one or more point mutations affecting a basic region of its C-terminal region.

Said defective integrase does not allow (or prevents) the integration of said at least one nucleic acid or of the cDNA thereof into the genome of a host cell, more particularly into the genome of a mammalian cell (more particularly into the genome of a mammalian neuronal cell and/or of a mammalian muscular cell and/or of a cell of the mammalian skeleton), more particularly into the genome of a human cell (more particularly into the genome of a human neuronal cell and/or of a human muscular cell and/or of a cell of the human skeleton).

Said defective integrase may e.g., be the integrase of Human Immunodeficiency Virus type 1 (HIV1), Human Immunodeficiency Virus type 2 (HIV2), Simian Immunodeficiency Virus (SIV), Feline Immunodeficiency Virus (FIV), Equine Infectious Anemia Virus (EIAV), Bovine Immunodeficiency Virus (BIV), visna virus or Caprine Arthritis Encephalitis Virus (CAEV), more particularly the integrase of HIV1, which has been made defective by mutation(s), more particularly an integrase of HIV1, which has been made defective by mutation(s), wherein said mutation(s) comprise(s) or consist(s) of one or more point mutations affecting a basic region of its C-terminal region (cf. WO 2006/010834). More particularly, said integrase may e.g., be the integrase of HIV1, which has been made defective by replacement of the $^{262}$RRK motif by AAH (cf. Philippe et al. 2006).

Said recombinant vector, more particularly a recombinant expression vector, more particularly a recombinant retroviral expression vector, more particularly a lentiviral expression vector advantageously is non-integrative, more particularly non-integrative and non-replicative.

The application more particularly relates to a recombinant retroviral expression vector, more particularly a lentiviral expression vector, more particularly a HIV expression vector, more particularly a HIV1 expression vector, which comprises at least one nucleic acid or RNA of the application (and regulatory elements for the expression of said at least one nucleic acid), wherein the integrase of said retrovirus or lentivirus has been made defective, more particularly which has been made defective by mutation(s), more particularly which has been made defective by mutation(s), wherein said mutation(s) comprise(s) or consist(s) of one or more point mutations affecting a basic region of its C-terminal region (cf. WO 2006/010834). Said retrovirus or lentivirus may e.g., be HIV1, HIV2, SIV, FIV, EIAV, BIV, visna or CAEV, more particularly H1V1.

The application more particularly relates to a recombinant HIV1 expression vector, which comprises at least one nucleic acid or RNA of the application (and regulatory elements for the expression of said at least one nucleic acid), wherein the integrase of said HIV1 has been made defective, more particularly which has been made defective by mutation(s), more particularly which has been made defective by mutation(s), wherein said mutation(s) comprise(s) or consist(s) of the replacement of the $^{262}$RRK motif by AAH (cf. Philippe et al. 2006).

Said recombinant vector, more particularly said recombinant expression vector, more particularly said recombinant retroviral expression vector, more particularly said lentiviral expression vector, more particularly said HIV1 vector, may further comprise a recombinant genome, which is devoid of, or has been deleted from, all the lentiviral encoding sequences, and which comprises, between the lentiviral LTR 5' and 3' sequences, a lentiviral encapsidation psi sequence, a RNA nuclear export element, a transgene comprising said at least one nucleic acid, and optionally, a promoter and/or a sequence favoring the nuclear import of RNA (cf. WO 99/55892).

Appropriate vectors comprise vectors, which are especially adapted for the expression of the nucleic acid of the application by, or in, a particular type of cells, tissue(s) or organ(s), for example, vectors, which are especially adapted for the expression of the inserted nucleic acid by neuronal cells, more particularly:

- an expression lentivirus-derived vector, more particularly,
  a non-replicative expression lentivirus-derived vector (e.g., as described in WO 2013/068430, cf. pages 35-44 of WO 2013/068430 and the examples of WO 2013/068430) or
- a lentiviral vector pseudotyped particle, more particularly a lentiviral vector, which has been pseudotyped with the G protein of a rabies virus (e.g., as described in WO 2013/068430, cf. pages 41-44 of WO 2013/068430 and the examples of WO 2013/068430).

The application more particularly relates to a recombinant vector, more particularly a recombinant expression vector, more particularly a recombinant (expression) plasmid, which comprises:

i. at least one nucleic acid of the application, more particularly at least one RNA of the application, ii. expression regulatory elements of said at least one nucleic acid or RNA,
iii. a cis-acting central initiation region (cPPT) and a cis-acting termination region (CTS), both of lentiviral origin, and
iv. regulatory signals of retroviral origin (more particularly, of lentiviral origin) for transcription (more particularly, for reverse transcription), expression and packaging.

Examples of the structure of such vectors (elements ii., iii. and iv.) are described in WO 2013/068430, more particularly from page 35 line 25 to page 41 line 4.

Said recombinant vector, more particularly said recombinant expression vector, more particularly said recombinant (expression) plasmid advantageously is non-replicative. Non-replication may be achieved by any means that the person of ordinary skill in the art may find appropriate, e.g., by deletion and/or mutation(s) of viral sequence(s) (e.g., of the gag and/or pol and/or env gene(s)) and/or of cis-acting genetic elements needed for particle formation (cf. WO 2013/068430, more particularly from page 40 line 26 to page 41 line 4).

The application also relates to a recombinant viral particle, more particularly to a lentiviral vector pseudotyped particle, comprising at least one nucleic acid vector of the application.

The application also relates to a recombinant viral particle, more particularly to a lentiviral vector pseudotyped particle, comprising GAG structural proteins and a viral core made of (a) POL proteins and (b) a lentiviral genome comprising said at least one nucleic acid or RNA of the application, expression regulatory elements of said at least one nucleic acid or RNA, a cis-acting central initiation region (cPPT) and a cis-acting termination region (CTS), both of lentiviral origin, and regulatory signals of retroviral origin for transcription (more particularly for reverse transcription), expression and packaging, wherein said particle is pseudotyped with the G protein of a Vesicular Stomatitis Indiana Virus (VSIV or VSV) or with the G protein of a rabies virus (cf. above and WO 2013/068430, more particularly from page 41 line 6 to page 44 line 28). Said rabies virus can e.g., be the ERA strain (ATCC vr332) or the CVS strain (ATCC vr959). The sequence of the G protein of the ERA strain is available under accession number AF406693. The sequence of the G protein of the CVS rabies virus strain is available under accession number AF406694. Said recombinant viral particle, more particularly said lentiviral vector pseudotyped particle, may advantageously have been made defective, i.e., the integrase of lentiviral origin (which is coded by the pol gene) is devoid of the capacity of integration of the lentiviral genome into the genome of a host cell, more particularly into the genome of a mammalian cell (more particularly into the genome of a mammalian neuronal cell and/or of a mammalian muscular cell and/or of a cell of the mammalian skeleton), more particularly into the genome of a human cell (more particularly into the genome of a human neuronal cell and/or of a human muscular cell and/or of a cell of the human skeleton). Said integrase may e.g., comprise mutation(s), which alter(s) or impede(s) its integrase activity. Examples of such defective integrases and of such mutation(s) are described in WO 2013/068430 from page 43 line 6 to page 44 line 28.

The application also relates to a set comprising a nucleic acid of the application and a nucleic acid vector of the application.

The application also relates to a set comprising a first nucleic acid and a second nucleic acid, wherein only one, or each one, of said first and second nucleic acids is a nucleic acid of the application. Said first nucleic acid is different from said second nucleic acid.

When only one of said first and second nucleic acids is a nucleic acid of the application, the other of said first and second nucleic acid is a nucleic acid, which is not of the application. For example, the set comprises a first nucleic acid, which is a nucleic acid of the application, and a second nucleic acid, which is not of the application, wherein said first nucleic acid of the application codes for a first DNA-binding polypeptide and said second nucleic acid codes for a second DNA-binding polypeptide, and wherein said first and second DNA-binding polypeptides are the first and second DNA-binding polypeptides of a mixed polypeptide set of the application as defined above (first DNA-binding polypeptide, which is of the application, and second DNA-binding polypeptide, which is not of the application; cf. above).

The application more particularly relates to a set wherein each of said first and second nucleic acids is a nucleic acid of the application.

The application also relates to a set comprising a first nucleic acid vector and a second nucleic acid vector, wherein only one, or each one, of said first and second nucleic acid vectors is a nucleic acid vector of the application. Said first nucleic acid vector is different from said second nucleic acid vector.

When only one of said first and second nucleic acid vectors is a nucleic acid vector of the application, the other of said first and second nucleic acid vectors is a nucleic acid vector, which is not of the application. For example, the set comprises a first nucleic acid vector, which comprises a nucleic acid of the application, and a second nucleic acid vector, which comprises a nucleic acid, which is not of the application, wherein said first nucleic acid of the application codes for a first DNA-binding polypeptide and said second nucleic acid codes for a second DNA-binding polypeptide, and wherein said first and second DNA-binding polypeptides are the first and second DNA-binding polypeptides of a mixed polypeptide set of the application as defined above (first DNA-binding polypeptide, which is of the application, and second DNA-binding polypeptide, which is not of the application; cf. above).

The application more particularly relates to a set, wherein each of said first and second nucleic acid vectors is a nucleic acid vector of the application.

Each of these sets can be herein referred to as the "nucleic acid/vector set of the application". The phrase "set" is intended in accordance with its ordinary meaning in the field. It notably encompasses the meaning of "a plurality of", more particularly the meaning of "a pair of". Said set of plurality can e.g., be in the form of one composition or kit, or of at least two compositions or of at least two kits.

Said one composition or kit comprises both said first and second DNA-binding nucleic acids or nucleic acid vectors.

Said at least two compositions or kits are in the form of separate compositions or kits, each comprising one of said first and second nucleic acids or nucleic acid vectors (e.g., a first composition or kit comprising said first nucleic acid or nucleic acid vector and a second composition or kit comprising said second nucleic acid or nucleic acid vector, wherein said first composition or kit is distinct or separate from said second composition or kit). Said at least two compositions or kits can be for simultaneous, separate, distinct or sequential use, more particularly for simultaneous or sequential use.

In said nucleic acid/vector set, the first and second nucleic acids or vectors can e.g., be present as isolated nucleic acids or vectors, as individual nucleic acids or vectors, or can be contained within cell(s), e.g., host and/or genetically engineered cell(s) as described below (the first nucleic acid or vector can be contained within the same cell as said second nucleic acid or vector, or in two distinct cells respectively).

The application relates to a composition or kit comprising:

a first recombinant nucleic acid vector and a second recombinant nucleic acid vector, wherein said first recombinant nucleic acid vector is different from said second recombinant nucleic acid vector and wherein said first recombinant nucleic acid vector and said second recombinant nucleic acid vector respectively code for the first DNA-binding polypeptide and for the second DNA-binding polypeptide as defined above; and/or comprising a first lentiviral vector pseudotyped particle and a second lentiviral vector pseudotyped particle, wherein said first lentiviral vector pseudotyped particle is different from said second lentiviral vector pseudotyped particle and wherein said first lentiviral vector pseudotyped particle and said second lentiviral vector pseudotyped particle respectively code for the first DNA-binding polypeptide and for the second DNA-binding polypeptide as defined above.

More particularly, each of said first and second recombinant nucleic acid vectors is a recombinant nucleic acid vector of the application, and/or each of said first and second lentiviral vector pseudotyped particles is a lentiviral vector pseudotyped particle of the application.

In said nucleic acid/vector set, said first nucleic acid and/or said second nucleic acid can be contained in/on a nanoparticle or liposome as described below, and/or said first nucleic acid vector and/or said second nucleic acid vector can be contained in/on a nanoparticle or liposome as described below.

Said nucleic acid/vector set can be contained in a composition suitable for nucleic acid transfection of a cell, more particularly of a eukaryotic cell, more particularly of a mammalian cell, a non-human mammalian cell (e.g., a rodent cell, such as a mouse cell), a human cell, a yeast cell, a bacterial cell or a plant cell, more particularly of a human cell or a yeast cell, more particularly of a human cell.

The term "transfection" herein encompasses its broadest general meaning in the field of genetic engineering. It notably encompasses any process of deliberately introducing a nucleic acid into a cell (said process can be virus-mediated or not virus-mediated, said cell can be eukaryotic or not eukaryotic).

Said nucleic acid/vector set may further comprises at least one cell, more particularly at least one eukaryotic cell, more particularly at least one mammalian cell, at least one non-human mammalian cell (e.g., a rodent cell, such as a mouse cell), at least one human cell, at least one yeast cell, at least one bacterial cell or at least one plant cell, more particularly at least one human cell or at least one yeast cell, more particularly at least one human cell.

The application also relates to a nanoparticle or to a liposome, which comprises at least one of the polypeptides, sets, nucleic acids, vectors and host cells of the application, more particularly which comprises at least one of the polypeptides, sets and host cells of the application. Said at least one polypeptide, set, nucleic acid, vector or host cell of the application can be contained in and/or on nanoparticles. Said at least one polypeptide, set, nucleic acid, vector or host cell of the application can be contained in and/or on a liposome, e.g., it can be encapsulated inside a liposome or associated to a liposome delivery system. Said liposome can e.g., be a cationic liposome, a pegylated liposome. Said liposome can be loaded with nanoparticles. The nanoparticle and/or liposome formulation of the polypeptide, set, nucleic acid, vector or host cell of the application is notably useful for improved crossing of the blood-brain barrier and/or for protection against serum degradation.

The application also relates to a cell, more particularly a eukaryotic cell more particularly a mammalian cell, a non-human mammalian cell, a human cell, a yeast cell, a bacterial cell or a plant cell, more particularly a human cell or a yeast cell, more particularly a human cell, which comprises at least one DNA-binding polypeptide of the application and/or at least one polypeptide set of the application and/or at least one nucleic acid of any one of the application and/or at least one nucleic acid vector of the application and/or at least one nucleic acid/vector set of the application and/or at least one liposome or nanoparticle of the application.

Said cell can e.g., be a host cell and/or a recombinant cell and/or a genetically engineered cell. The application also relates to the in vitro use of said cell for the production or synthesis of at least one DNA-binding polypeptide of the application and/or at least one polypeptide set of the application and/or at least one nucleic acid of the application and/or at least one nucleic acid vector of the application and/or at least one nucleic acid/vector set of the application and/or at least one liposome or nanoparticle of the application.

The application also relates to an in vitro method for the production of a product, which binds, or specifically binds, to a (double-stranded) DNA nucleic acid comprising at least one DNA tandem repeat, more particularly which cleaves, or specifically cleaves, a (double-stranded) DNA nucleic acid comprising at least one DNA tandem repeat, more particularly which fully or partially deletes said at least one DNA tandem repeat, more particularly which fully or partially deletes said at least one DNA tandem repeat in a specific manner.

Said method typically comprises in vitro growing said cell of the application on a culture medium, allowing it to produce said at least one DNA-binding polypeptide of the application and/or at least one nucleic acid of the application and/or at least one nucleic acid vector of the application, and collecting said at least one DNA-binding polypeptide of the application and/or at least one nucleic acid of the application and/or at least one nucleic acid vector of the application.

The application also relates to a method for producing (at least one) DNA-binding polypeptide, which binds, or specifically binds, to a DNA nucleic acid comprising at least one DNA tandem repeat, wherein said method comprises producing or synthesizing a DNA-binding polypeptide of the application.

The application also relates to a method for producing a pair of DNA-binding polypeptides, which comprises producing or synthesizing a first DNA-binding polypeptide and a second DNA-binding polypeptide, wherein said first DNA-binding polypeptide and said second DNA-binding polypeptide are as defined above for a polypeptide set of the application.

The expression "synthesizing a polypeptide" encompasses synthesizing a polypeptide by chemical synthesis (e.g., by solid phase synthesis, or by liquid phase synthesis), as well as synthesizing a polypeptide by recombinant expression. More particularly, said expression encompasses the synthesis of a polypeptide by recombinant expression, more particularly by recombinant expression of a nucleic acid of the application and/or of a nucleic acid vector of the application and/or from a host cell of the application and/or from a composition comprising a first nucleic acid and a second nucleic acid of the application (as defined above). Said method may further comprise the collection of the synthesized polypeptide, e.g., by purification and/or isolation, for example by antibody capture and/or by HPLC.

The application also relates to a non-human animal (e.g., a rodent, such as a mouse, or pig, or a rabbit), which has been engineered to contain or produce at least one DNA-binding polypeptide of the application and/or at least one polypeptide set of the application and/or at least one nucleic acid of the application and/or at least one nucleic acid vector of the application and/or at least one nucleic acid/vector set of the application and/or at least one cell of the application.

The application also relates to the use of said non-human animal for the production or synthesis of at least one DNA-binding polypeptide of the application and/or at least one nucleic acid of the application and/or at least one nucleic acid vector of the application.

The application also relates to a method for the production of a product, which binds, or specifically binds, to a (double-stranded) DNA nucleic acid comprising at least one DNA tandem repeat, more particularly which cleaves, or specifically cleaves, a (double-stranded) DNA nucleic acid comprising at least one DNA tandem repeat, more particularly which fully or partially deletes said at least one DNA tandem repeat, more particularly which fully or partially deletes said at least one DNA tandem repeat in a specific manner.

Said method typically comprises breeding or keeping said non-human animal, allowing it to produce at least one DNA-binding polypeptide of the application and/or at least one nucleic acid of the application and/or at least one nucleic acid vector of the application, and collecting from said animal at least one DNA-binding polypeptide of the application and/or at least one nucleic acid of the application and/or at least one nucleic acid vector of the application.

The application also relates to a composition, more particularly to a pharmaceutical composition, medicament, drug or kit, which comprises at least one product of the application, more particularly at least one DNA-binding polypeptide of the application and/or at least one polypeptide set of the application and/or at least one nucleic acid of the application and/or at least one nucleic acid vector of the application and/or at least one nucleic acid/vector set of the application and/or at least one liposome or nanoparticle of the application and/or at least one cell of the application.

Said pharmaceutical composition, medicament, drug or kit may further comprise at least one pharmaceutically acceptable vehicle or carrier, more particularly a physiologically acceptable vehicle or carrier, more particularly a vehicle or carrier, which is adapted to the physiology of a mammal, e.g., a human or non-human mammal. Said vehicle or carrier can be mixed with said at least one product of the application.

Said vehicle or carrier can e.g., be or comprise one or several elements selected from at least one diluent, at least one excipient, at least one additive, at least one pH adjuster, at least one pH buffering agent, at least one emulsifier agent, at least one dispersing agent, at least one preservative, at least one surfactant, at least one gelling agent, at least one buffering agent, at least one stabilizing agent and at least one solubilising agent.

Appropriate pharmaceutically acceptable vehicles and formulations include all known pharmaceutically acceptable vehicles and formulations, such as those described in "Remington: The Science and Practice of Pharmacy", $20^{th}$ edition, Mack Publishing Co.; and "Pharmaceutical Dosage Forms and Drug Delivery Systems", Ansel, Popovich and Allen Jr., Lippincott Williams and Wilkins.

When said composition, pharmaceutical composition, medicament, drug or kit is intended for administration to a subject (e.g., a non-human mammal or a human) in need thereof, the nature of the vehicle will in general depend on the particular mode of administration being employed. For instance, parenteral formulations usually comprise injectable fluids that include pharmaceutically and physiologically acceptable fluids, including water, physiological saline, balanced salt solutions, buffers, aqueous dextrose, glycerol, ethanol, sesame oil, combinations thereof, or the like as a vehicle. The medium may also contain conventional pharmaceutical adjunct materials such as, for example, pharmaceutically acceptable salts to adjust the osmotic pressure, buffers, preservatives and the like.

In said composition, pharmaceutical composition, drug, medicament or kit of the application, said at least one product of the application can e.g., be formulated as, or contained in, a liquid solution, a suspension, an emulsion or a capsule. It can be formulated e.g., for immediate release, or for differed release or sustained release formulation.

Advantageously, said composition, pharmaceutical composition, drug, medicament or kit is stored or contained in a sterile container and/or environment.

The application describes products, which are DNA-binding polypeptides, nucleic acids, sets, vectors, liposomes, nanoparticles, cells, non-human animals, compositions, pharmaceutical compositions, medicaments, drugs, kits.

Each of these products is useful in the medical field, more particularly in the field of the treatment and/or palliation and/or prevention of a disease or disorder.

Said disease or disorder can e.g., be any disorder or disease involving at least one DNA tandem repeat (as above described), more particularly at least one (direct) DNA tandem repeat in a DNA nucleic acid, more particularly at least one (direct) DNA tandem repeat in a double-stranded DNA nucleic acid.

Said disease or disorder can e.g., be any disorder or disease involving at least one expanded or abnormally-expanded DNA tandem repeat, more particularly at least one expanded or abnormally-expanded DNA tandem repeat in a DNA nucleic acid, more particularly at least one expanded or abnormally-expanded DNA tandem repeat in a double-stranded DNA nucleic acid. The phrase "expanded" or "abnormally-expanded" means that the number of repeat units forming the DNA tandem repeat is above the normal average number (for the DNA nucleic acid in consideration).

Said disease or disorder can e.g., be a neurological and/or muscular and/or skeletal disorder or disease.

Said disease or disorder can e.g., be a neurological and/or muscular and/or skeletal disorder or disease involving at least one DNA tandem repeat as above-described.

Said at least one DNA tandem repeat may e.g., have a non-linear secondary structure such as a hairpin, a triple helix or a tetraplex.

Said disease or disorder can e.g., be a neurological and/or muscular and/or skeletal disorder or disease involving at least one DNA tandem repeat in a double-stranded DNA nucleic acid, more particularly at least one DNA tandem repeat in a double-stranded DNA nucleic acid, wherein said at least one DNA tandem repeat has a non-linear secondary structure such as a hairpin, a triple helix or a tetraplex.

Said at least one DNA tandem repeat can be contained in a gene, more particularly a eukaryotic gene, more particularly a non-mammalian eukaryotic gene, e.g., a yeast gene, more particularly a mammalian gene, e.g., a non-human mammalian gene or a human gene. Advantageously, said at least one DNA tandem repeat is contained in a chromosome, more particularly is a gene, a non-mammalian eukaryotic gene, a mammalian gene, a non-human mammalian gene or a human gene, wherein said gene is contained in a chromosome, more particularly a human chromosome.

Said at least one DNA tandem repeat can be contained in any location of said gene, e.g., in a promoter and/or in the 5'UTR and/or in at least one exon and/or in at least one intron and/or in the 3'UTR of said gene.

Said disease or disorder can e.g., be a trinucleotide repeat disease or disorder, a tetranucleotide repeat disease or disorder, or a pentanucleotide repeat disease or disorder.

Said disease or disorder can e.g., be any disease or disorder selected from the group consisting of DM1, SCA8, SCA12, HDL2, SBMA, HD, DRPLA, SCA7, SCA2, SCA3, SCA6, SCA7, SCA17, PSACH, DM2, SCA10, SPD1, OPMD, CCD, HPE5, HFG syndrome, BPES, EIEE1, FRAXA, FXTAS and FRAXE (cf. Table 6 above).

According to an aspect of the application, when said at least one DNA nucleic acid is a double-stranded nucleic acid, at least one of its two strands (either only one of them or both of them) contains nucleotide(s) T in DNA tandem repeat unit.

Said disease or disorder can e.g., be any disease or disorder selected from the group consisting of DM1, SCA8, SCA12, HDL2, SBMA, HD, DRPLA, SCA7, SCA2, SCA3, SCA6, SCA7, SCA17, PSACH, DM2 and SCA10 (cf. Table 6 above).

More particularly, said disease or disorder is DM1.

Said disease and disorders are described in Table 6 above. Table 7 identifies the at least one DNA nucleic acid, which is involved in each of said diseases or disorders, respectively. Table 8 identifies the nature of the DNA tandem repeat unit that is contained in said at least one DNA nucleic acid. Table 8 also provides the normal average range of DNA tandem repeat units that are contained in said at least one DNA nucleic acid. A number of DNA tandem repeat units above said normal average range is generally considered to be an abnormal number of DNA tandem repeat units, i.e., it is then generally considered that the at least one DNA tandem repeat is an expanded or abnormally-expanded DNA tandem repeat.

The application notably relates to the use of at least one DNA-binding polypeptide of the application, more particularly the use of a first and second DNA-binding polypeptides of the application (as above defined), or the use of at least one nucleic acid or vector of the application (as above defined), more particularly the use of a first and second nucleic acids or vectors of the application (as above defined), wherein said use is in the manufacture of a medicament for treating and/or palliating and/or preventing a disease or disorder involving at least one DNA tandem repeat, more particularly a disease or disorder as above defined.

The application also relates to said at least one DNA-binding polypeptide of the application, more particularly to said first and second DNA-binding polypeptides of the application, or to said at least one nucleic acid or vector of the application, or to said first and second nucleic acids of the application, for its/their use as a medicament.

The application also relates to said at least one DNA-binding polypeptide of the application, more particularly to said first and second DNA-binding polypeptides of the application, or to said at least one nucleic acid or vector of the application, or to said first and second nucleic acids of the application, for its/their use in the treatment and/or palliation and/or prevention of a disease or disorder involving at least one DNA tandem repeat, more particularly a disease or disorder as above defined.

The application also relates to a method for producing a drug or medicament that is useful in the treatment and/or palliation and/or prevention of a disease or disorder involving at least one DNA tandem repeat, more particularly a disease or disorder as above defined. Said method comprises:

producing said at least one DNA-binding polypeptide of the application, more particularly said first and second DNA-binding polypeptides of the application, and/or producing said at least one nucleic acid or vector of the application, more particularly said first and second nucleic acids of the application, and/or producing a composition or kit of the application, formulating said polypeptide(s) and/or nucleic acid(s) or vector(s) and/or composition or kit as a drug or medicament (more particularly, mixing said polypeptide(s) and/or nucleic acid(s) or vector(s) with at least one vehicle or carrier e.g., at least one vehicle or carrier as above defined).

A product of the application can induce a double-strand break in a double-stranded DNA nucleic acid. More particularly, a product of the application can induce a double-strand break specifically in a double-stranded DNA nucleic acid.

A product of the application can act by cleaving said at least one DNA tandem repeat, more particularly by reducing the number of units contained in said at least one DNA tandem repeat, more particularly by fully or partially deleting said at least one DNA tandem repeat.

According to an advantageous aspect of the application, a product of the application allows a deletion or reduction of said at least one DNA tandem repeat down to a non-abnormal number of repeat units, i.e., down to below the abnormal range (cf. e.g., Table 8 for the average normal range of DNA tandem repeat units that is generally observed in illustrative disease or disorders).

The example below illustrates that the efficiency of a product of the application in achieving said deletion or reduction is very high (near 100% in heterozygous and homozygous yeast cells).

The example below illustrates that a product of the application can act without inducing an increase in the mutation rate and without inducing any large genomic rearrangement, such as aneuploidy, segmental duplication or translocation.

Advantageously, a means of the application is less toxic than the prior art means, more particularly than the Zinc Finger prior art means.

Advantageously, a means of the application does not induce any length alteration or mutation at off-target locations, e.g., in non-pathological genes, which comprise the same repeat unit as the pathological gene. It is notably the case when the DNA target site of said first DNA-polypeptide is a non-overlapping DNA target site (as defined above) and when the DNA target site of said second DNA-polypeptide is an overlapping DNA target site (as defined above). Please see FIG. 1B for an illustration of such a configuration.

It is believed that it is the first demonstration that the shortening of a DNA tandem repeat to lengths below pathological thresholds in humans can be induced with 100% efficacy and a high specificity.

Reduction in size of an abnormally-expanded tandem repeat unit provides a genetic treatment and/or palliation and/or prevention of the disease or disorder. Indeed it has been demonstrated that, when a large trinucleotide repeat contraction of an expanded myotonic dystrophy allele occurred during transmission from father to daughter, complete clinical examination of the daughter showed no sign of myotonic dystrophy symptoms (O'Hoy et al. 1993).

Hence, a product of the application actually provides a means for gene therapy and/or palliation and/or prevention of said diseases or disorders.

The application also relates to a method of treatment of a subject in need thereof, which comprises administering at least one product of the application to said subject.

Said subject can e.g., be a mammal (e.g., a non-human mammal or a human), more particularly a human.

Said at least one product can more particularly be at least one DNA-binding polypeptide of the application, at least one polypeptide set (composition or kit) of the application, at least one nucleic acid, at least one set of nucleic acids, at least one liposome, at least one nanoparticle, at least one vector or at least one cell of the application.

Said at least one product can more particularly be at least one pharmaceutical composition, medicament or drug of the application.

The application also relates to the (in vitro) use of at least one product of the application in the selection of a product suitable for cleavage and/or reduction in size, and/or full or partial deletion of at least one (expanded or abnormally-expanded) DNA tandem repeat, more particularly at least one (expanded or abnormally-expanded) DNA tandem repeat in a DNA nucleic acid, more particularly at least one (expanded or abnormally-expanded) DNA tandem repeat in a double-stranded DNA nucleic acid.

The application also relates to a method for identifying a product useful in the treatment and/or palliation and/or prevention of a disease or disorder as above defined, which comprises:
  in vitro growing cells, which comprise at least DNA nucleic acid, wherein said at least one DNA nucleic acid comprises said at least one DNA tandem repeat to be cleaved and/or reduced in size and/or fully or partially deleted, wherein said cells are the cells of a cell line (e.g., a cell line, which is considered by the person of average skill in the art as a model of one or several of said diseases or disorders, e.g., one or several of the diseases or disorders of Table 6 above), or wherein said cells are cells, which have been collected from a mammal, more particularly from a non-human mammal or from a human, more particularly from a human in need of said treatment and/or palliation and/or prevention (e.g., a human affected by at least one disease or disorder listed in Table 6 above),
  contacting at least one cell of said cells with at least one product of the application,
  contacting at least one other of said cells with at least one other product of the application, and
  selecting the at least one product, which achieves said cleavage and/or reduction in size and/or full or partial deletion with the highest efficiency and/or with the lowest undesired side effects.

Selecting the at least one product, which achieves said cleavage and/or reduction in size and/or full or partial deletion with the lowest undesired side effects notably encompasses selecting the at least one product, which achieves said cleavage and/or reduction in size and/or full or partial deletion, and which induces the lowest level of one or several side effect(s) selected from the group consisting of induced toxicity, rate of induced mutation, induced rate of genomic rearrangement, induced rate of aneuploidy, induced rate of segmental duplication, induced rate of translocation, rate of off-target cleavage, e.g., in non-pathological genes, which comprise the same repeat unit as the pathological gene.

The application also relates to a method for producing a product useful for fully or partially deleting a DNA tandem repeat that is contained in a double stranded DNA nucleic acid, more particularly for fully or partially deleting a DNA tandem repeat that is contained in a double stranded DNA nucleic acid and forms a non-linear secondary structure in said double stranded DNA nucleic acid (more particularly a secondary structure, which is a hairpin, a triple helix or a tetraplex structure). Said double-stranded DNA nucleic acid is as above defined and can e.g., be contained in a chromosome, more particularly a gene that is contained in a chromosome, more particularly in a human chromosome, more particularly a human gene that is contained in a chromosome. Said full or partial deletion is a deletion or excision of all or several of the repeated units of said DNA tandem repeat, more particularly a specific deletion or excision of all or several of the repeated units of said DNA tandem repeat. Said method comprises producing a pair of DNA-binding polypeptides of the application (i.e., a first DNA-binding polypeptide and a second DNA-binding polypeptide as defined above for a polypeptide set, or mixed set, of the application), e.g., according to the method of the application. Said pair of DNA-binding polypeptides is a product useful for said full or partial DNA tandem repeat deletion.

At least one of said first and second DNA-binding polypeptides is a DNA-binding polypeptide of the application, more particularly a DNA-binding polypeptide of the application, the DNA target of which is a non-overlapping or an overlapping DNA target site as defined above, more particularly a DNA-binding polypeptide of the application, the DNA target of which is a non-overlapping DNA target site as defined above. Advantageously, said first DNA-binding polypeptide is a DNA-binding polypeptide of the application, the DNA target of which is a non-overlapping DNA target site as defined above, and said second DNA-binding polypeptide is a DNA-binding polypeptide of the application, the DNA target of which is an overlapping DNA target site as defined above.

The application also relates to a method for inducing (or generating), more particularly in vitro inducing (or generating), a double-strand DNA break (into a double-stranded DNA nucleic acid).

Said method comprises placing a double-stranded DNA into contact with a first DNA-binding polypeptide and with a second DNA-binding polypeptide (said first DNA-binding polypeptide and said second DNA-binding polypeptide are as defined above for a polypeptide set, or mixed set, of the application), or with nucleic acid(s) coding for said first and second DNA-binding polypeptides, or with a composition or kit, which comprises said first DNA-binding polypeptide and said second DNA-binding polypeptide and/or which comprises nucleic acid(s) coding for said first and second DNA-binding polypeptides (cf. above).

At least one of said first and second DNA-binding polypeptides is a DNA-binding polypeptide of the application, more particularly a DNA-binding polypeptide of the application, the DNA target of which is a non-overlapping or an overlapping DNA target site as defined above, more particularly a DNA-binding polypeptide of the application, the DNA target of which is a non-overlapping DNA target site as defined above. Advantageously, said first DNA-binding polypeptide is a DNA-binding polypeptide of the application, the DNA target of which is a non-overlapping DNA target site as defined above, and said second DNA-binding polypeptide is a DNA-binding polypeptide of the application, the DNA target of which is an overlapping DNA target site as defined above.

The application also relates to a method for fully or partially deleting, more particularly for in vitro fully or partially deleting, a DNA tandem repeat that is contained in a double stranded DNA nucleic acid (or a DNA tandem repeat in a double stranded DNA nucleic acid, which is contained in a chromosomal DNA, more particularly in a human chromosomal DNA).

Said method comprises placing a double-stranded DNA into contact with a first DNA-binding polypeptide and with second DNA-binding polypeptide (said first DNA-binding polypeptide and said second DNA-binding polypeptide are as defined above for a polypeptide set, or mixed set, of the application), or with nucleic acid(s) coding for said first and second DNA-binding polypeptides, or with a composition or kit, which comprises said first DNA-binding polypeptide and said second DNA-binding polypeptide and/or which comprises nucleic acid(s) coding for said first and second DNA-binding polypeptides (cf. above).

At least one of said first and second DNA-binding polypeptides is a DNA-binding polypeptide of the application, more particularly a DNA-binding polypeptide of the application, the DNA target of which is a non-overlapping or an overlapping DNA target site as defined above, more particularly a DNA-binding polypeptide of the application, the DNA target of which is a non-overlapping DNA target site as defined above. Advantageously, said first DNA-binding polypeptide is a DNA-binding polypeptide of the application, the DNA target of which is a non-overlapping DNA target site as defined above, and said second DNA-binding polypeptide is a DNA-binding polypeptide of the application, the DNA target of which is an overlapping DNA target site as defined above.

Said first and second DNA-binding polypeptides produce or generate a double-strand DNA break in said double-stranded DNA nucleic acid. Please see FIGS. 1A, 1B and 3B for illustrations of double strand DNA breaks. Said double-stranded DNA nucleic acid is as above defined and can e.g., be contained in a chromosome, more particularly a gene that is contained in a chromosome, more particularly a human gene that is contained in a chromosome. Said double-stranded DNA nucleic acid can be an isolated or purified DNA, or can be contained into a cell. When said double-stranded DNA nucleic acid is contained into a cell, said method may further comprise allowing said first and second DNA-binding polypeptides to contact or reach said double-stranded DNA.

The application also relates to an (in vitro) method for fully or partially deleting a DNA tandem repeat that is contained in a double stranded DNA nucleic acid, more particularly in a chromosomal DNA, more particularly in a human chromosomal DNA. Said method comprises:
- (in vitro) contacting a cell containing said double-stranded DNA nucleic acid, more particularly said chromosomal DNA, with at least one DNA-binding polypeptide of the application and/or
- (in vitro) contacting and/or (in vitro) transfecting said cell with at least one nucleic acid of the application. More particularly, said method comprises:
- contacting said cell with a first DNA-binding polypeptide of the application and with a second DNA-binding polypeptide of the application (said first and second DNA-binding polypeptides being as above defined) and/or
- contacting and/or transfecting said cell with a nucleic acid or with nucleic acids coding for said first and second DNA-binding polypeptides, more particularly with a first nucleic acid of the application and with a second nucleic acid (as above defined).

The phrase "transfecting" is as defined above: it is intended with its broadest general meaning in the field of genetic engineering. It notably encompasses any process of deliberately introducing a nucleic acid into a cell (said process can be virus-mediated or not virus-mediated, said cell can be eukaryotic or not eukaryotic).

Said cell can be an isolated or purified cell, or can be contained in an organ or tissue, e.g., an organ or tissue, which has been collected from a subject, a patient, a mammal, a non-human mammal, a human. Said cell, organ or tissue can be a mammal cell, organ or tissue, for example a human cell, organ or tissue, or a non-human mammal cell, organ or tissue, such as rodent cell, organ or tissue, a rat cell, organ or tissue, a mouse cell, organ or tissue, a rabbit cell, organ or tissue, a pig cell, organ or tissue. Whether it is human or non-human, said cell can e.g., be a fibroblast cell, a neuronal cell, a skeletal muscle cell, a heart cell, a skin cell, a kidney cell. Whether it is human or non-human, said organ or tissue can e.g., be a skeletal muscle or a tissue or sample thereof, a heart or a tissue or sample thereof, skin or a tissue or sample thereof, kidney or a tissue or sample thereof.

In the application, unless specified otherwise or unless a context dictates otherwise, all the terms have their ordinary meaning in the relevant field(s).

The term "comprising", which is synonymous with "including" or "containing", is open-ended, and does not exclude additional, un-recited element(s), ingredient(s) or method step(s), whereas the term "consisting of" is a closed term, which excludes any additional element, step, or ingredient which is not explicitly recited.

The term "essentially consisting of" is a partially open term, which does not exclude additional, un-recited element(s), step(s), or ingredient(s), as long as these additional element(s), step(s) or ingredient(s) do not materially affect the basic and novel properties of the application. Accordingly, the term "comprising" (or "comprise(s)") hence includes the term "consisting of" ("consist(s) of"), as well as the term "essentially consisting of" ("essentially consist(s) of").

In an attempt to help the reader of the present application, the description has been separated in various paragraphs and/or sections and/or embodiments and/or aspects. These separations should not be considered as disconnecting the substance of a paragraph and/or section and/or embodiment and/or aspect from the substance of another(other) paragraph(s) and/or section(s) and/or embodiment(s) and/or aspect(s). To the contrary, the present application encompasses all the combinations of the various sections, paragraphs, embodiments and aspects that can be contemplated by the person of average skill in the art.

Each of the relevant disclosures of all references cited herein is specifically incorporated by reference. The following examples are offered by way of illustration, and not by way of limitation.

EXAMPLES

Example 1

Trinucleotide repeat expansions are responsible for at least two dozens severe neurological or developmental disorders in humans. A double-strand break between two short CAG/CTG trinucleotide repeats was formerly shown to induce a high frequency of repeat contractions in yeast cells (Richard et al. 1999). We conceived that specific endonucleases called TALENs (described in Cermark et al. 2011) could provide us with a new and modular tool to induce a double-strand break within a repeat array.

Here we show, using a dedicated genetic selection screen, that TALEN induction of a double-strand break into a CAG/CTG trinucleotide repeat in heterozygous diploid cells results in gene conversion of the repeat tract with near 100% efficacy, de facto deleting the repeat tract. Induction of the same TALEN in homozygous diploid cells leads to contractions of both repeat tracts to a final length of 3-13 triplets, with 100% efficacy.

High throughput sequencing of yeast colonies, before and after TALEN induction, shows that the TALEN does not increase mutation rate to a level detectable in our experiments.

No other CAG/CTG triplet repeat of the yeast genome, besides the one that was targeted, showed any length alteration or mutation.

No large genomic rearrangement such as aneuploidy, segmental duplication or translocation was detected.

It is believed that it is the first demonstration that induction of a dedicated TALEN in a eukaryotic diploid nucleus leads to shortening of a specific tandem repeat tract to lengths below pathological thresholds in humans, with 100% efficacy and a high specificity, effectively paving the way to gene therapy of diseases or disorders linked to tandem repeat expansions.

In the present example, a TALEN designed to recognize and cut a CAG/CTG trinucleotide repeat was assayed in a dedicated yeast experimental system. The assay relies on a modified suppressor tRNA gene (SUP4) in which the natural intron was replaced by either a short spacer sequence (18 bp), hereafter called SUP4-opa1) or a CAG/CTG trinucleotide repeat (125-180 bp, depending on repeat length, hereafter called sup4-(CAG)). The SUP4-opa1 allele is functional and suppresses an ade2-opa1 non-sense mutation that accumulates a red pigment into yeast cells, whereas the sup4-(CAG) is not functional (Richard et al. 1999, Richard et al. 2000). Diploid yeast cells carrying homozygous ade2-opa1 mutations are red if only one copy of SUP4-opa1 is present, but they revert to white if two copies are present (FIG. 1A). Haploid cells of opposite mating types containing either SUP4-opa1 or sup4-(CAG), were transformed with one of the two TALEN arms. As a control, a TALEN arm modified to bind a recognition site split in two halves separated by 49 bp, was also transformed in one of the two haploid strains. The left arm of this split-TALEN should not be able to bind its cognate site and therefore no double-strand break should be induced (FIG. 1B). TALEN arms are carried by multicopy plasmids (2 microns) and their expression is under the control of the inducible GAL1-10 promoter (Giniger et al. 1985). Cells were simultaneously plated on glucose and galactose media and colonies were scored after 3-5 days of growth. Yeast survival to the TALEN induction was 81.4%±7.2%, slightly less than survival to the split-TALEN induction (96.4%, FIG. 2A). White colonies were scored and represent a majority of cells on both media, even though they are more frequent on galactose (82.5% of white colonies) as compared to glucose (66.7%). This suggests that even in repressing conditions (glucose), the GAL1-10 promoter shows some level of leakiness which is, associated to multicopy plasmids, apparently sufficient to induce TALEN expression. In support of this observation, we noticed that when crossing two haploids strains containing a stable trinucleotide repeat and one of the two TALEN arms, none of the diploids obtained contained a repeat longer than 30 triplets, strongly suggesting than even in repressing conditions, leaky expression of both TALEN arms occur to a level high enough to induce repeat contractions when both plasmids are in the same diploid cell (cf. FIG. 4).

Figure 2A:
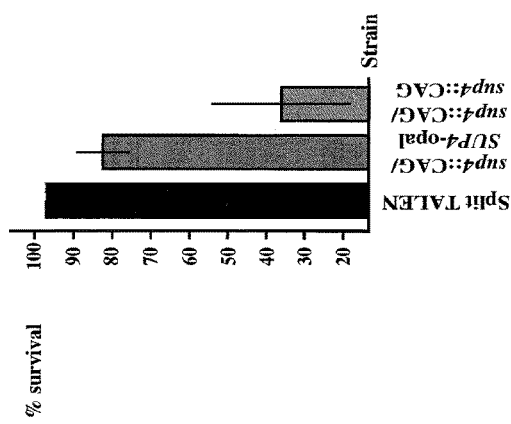
FIGS. 2A to 2D: Molecular analysis of survivors after TALEN induction.
Figure 2B:
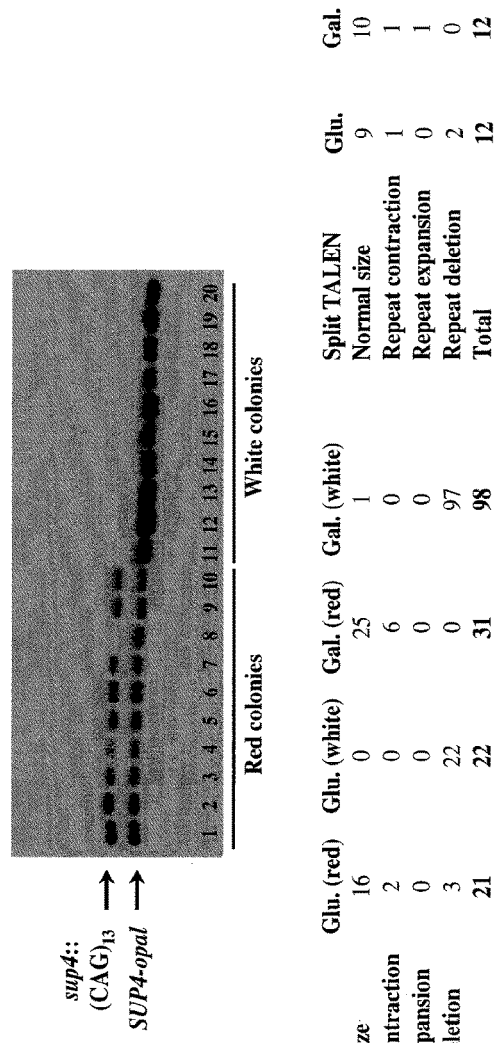
Figure 2C:
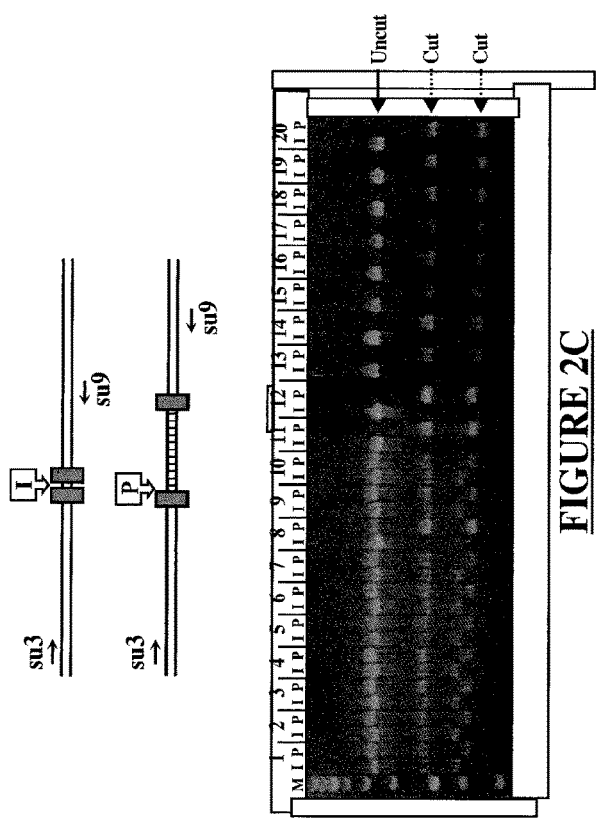

DNA originating from red and white colonies was subsequently analyzed by Southern blotting. Forty-nine out of 52 red colonies contain the two alleles, only three colonies showed the complete deletion of the sup4-(CAG) allele (FIG. 2B). Conversely, 119 out of 120 white colonies only contain the SUP4-opa1 allele, whose signal intensity was twice the intensity detected in red colonies, suggesting that it corresponds to a near-complete deletion of the sup4-(CAG) allele. We took advantage of a restriction site polymorphism between SUP4-opa1 and sup4-(CAG) alleles, to discriminate between a perfect homozygotization and a large contraction of the sup4-(CAG) allele. DNA extracted from red or white diploid survivors was amplified and digested with enzymes recognizing one of the two alleles. In all ten white survivors analyzed, restrictions showed the presence of only the SUP4-opa1 allele (FIG. 2C). Sequencing the same PCR products amplified from white diploid survivors confirmed that only one sequence was present, and not a mix of two different sequences, as would be expected for an heterozygous SUP4/sup4 locus. These experiments proved that gene conversion of the sup4-(CAG) allele by the SUP4-opa1 allele was more than 99% efficient following TALEN expression. Comparatively, there was no difference between glucose and galactose and no gene conversion was detected when inducing the split-TALEN (FIG. 2B).

In a second set of experiments, we built a diploid strain containing two sup4-(CAG) alleles of different lengths. In such a strain, it is not possible to screen for white colonies, since both alleles are deficient in suppressing ade2-opa1 mutation. In this strain, survival to galactose induction dropped to 37.1%±18%, a FIG. 2.2 fold lower than survival of the SUP4-opa1/sup4-(CAG) heterozygote (FIG. 2A). This shows that cutting both chromosomes instead of one decreases viability by about a two-fold factor. Molecular analysis showed that ca. 5% of colonies on glucose (2 out of 37) showed a small expansion, whereas 59% (22 out of 37) of colonies exhibited a contracted or deleted allele (FIG. 2D), suggesting again that some TALEN induction occurs in repressing conditions.

Figure 3A:
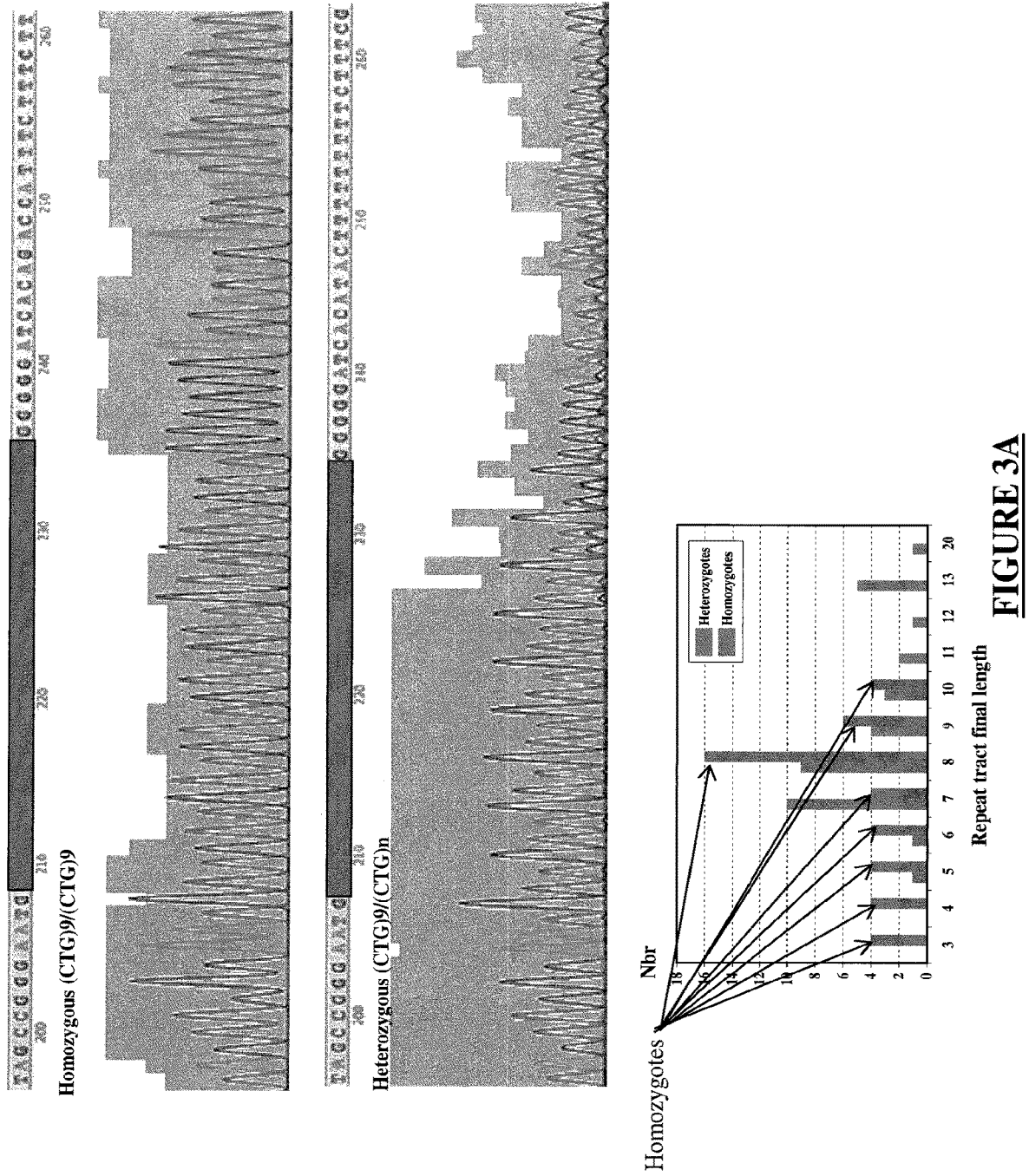
FIGS. 3A to 3D: Karyotypes and sequencing of TALEN-induced yeast colonies.

In galactose, 100% of the 153 colonies analyzed showed one single band corresponding in size to the near-complete deletion of the repeat tract. However, Southern blot resolution was not sufficient to determine if both alleles harbored repeats of the exact same length. DNA extracted from diploid survivors was therefore amplified and sequenced. In 23 out of 60 sequenced survivors (38%), only one sequence was present, as shown by good quality, evenly spaced peaks (FIG. 3A). In 37 out of 60 survivors (62%), a mix of two DNA sequences was read after the repeat tract, indicating that the two alleles carry repeat tracts of different lengths. Using this approach, only the shortest of the two repeat tract lengths could be determined, and was found to range from three to 13 triplets (with one exception, one sequence of 20 triplets was found). Given the size of both TALE recognition sites, we determined that the minimal spacing between the two TALE DNA-binding domains necessary to obtain active dimerization of the Fok I nuclease and subsequent DSB formation was 18 bp (FIG. 1B).

Figures 3B, 3C:
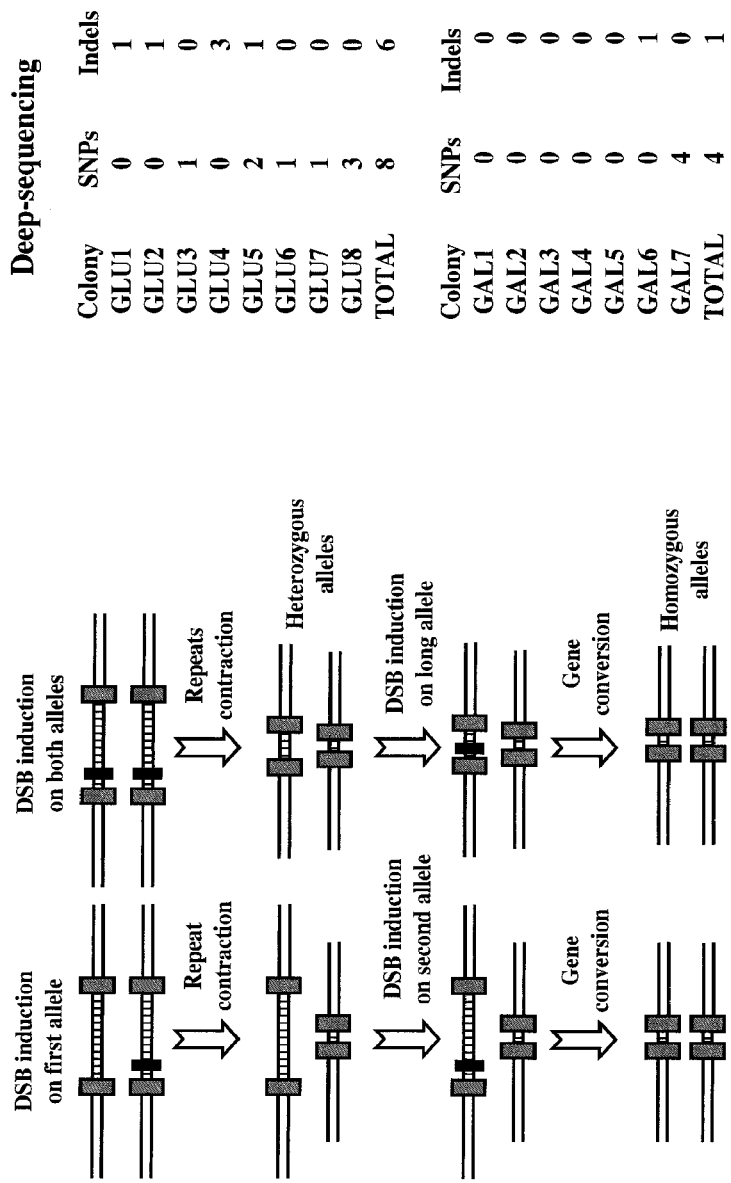

Homozygous survivors may result from iterative coordinated or uncoordinated breaks on both chromosomes, one (or two) allele(s) being cut and repaired by intra-molecular mechanism, while the other allele is repaired by gene conversion using the shortest one as a template (FIG. 3B). Heterozygous survivors may result as before, from iterative coordinated breaks, that will not be repaired by gene conversion and will therefore lead to repeat tracts of different lengths. This may be due to the presence of CAG repeats at DSB ends, which may impede one or more steps of homologous recombination, including correct processing of the break, subsequent formation of Rad51 nucleofilament, or strand invasion of the homologous template (which also contains CAG repeats). In support of this hypothesis, distribution of repeat tract lengths among heterozygous and homozygous survivors shows that homozygous tract lengths are shorter on the average (mean=7 triplets) than heterozygous tract lengths (mean=9 triplets), this difference being very significant (Wilcoxon test, p-value=0.0021, FIG. 3A). This suggests that gene conversion between repeat tracts may be hindered when tract lengths are too long, probably inhibiting an early step in the recombination process. In these cases, intramolecular repair is favored, giving rise to longer repeat tracts of unequal lengths. However, we cannot totally exclude that heterozygous survivors result from slippage occurring during DNA synthesis associated to gene conversion. When competition is possible between intra- and intermolecular repair mechanisms, intramolecular events might be favored, even though homologous recombination is highly efficient in yeast.

In order to determine TALEN specificity, particularly if an increase in off-site mutations was associated with its expression, we completely re-sequenced eight colonies growing on glucose plates and seven colonies growing on galactose plates. Paired-end ILLUMINA reads were generated and mapped to the S288C reference genome for each colony (cf. Table 2). After removal of duplicates, coverage of unique sequences was homogeneous in all 15 clones sequenced, showing no aneuploidy and no segmental duplication. Among eight glucose colonies, eight unique heterozygous SNPs were detected, whereas among seven galactose colonies four unique heterozygous SNPs were detected (FIG. 3C). These numbers are not significantly different from each other and are in good agreement with predictions. Lynch et al. 2008 determined that the average base substitution rate per nucleotide site was $3.3 \times 10^{-10}$ per cell division, in *S. cerevisiae*. Given that glucose and galactose colonies underwent approximately only 30 cell divisions before DNA was extracted and sequenced, it was expected that most of the colonies did not contain any base substitution. Nine colonies out of 15 did not contain any SNP, whereas the remaining contained between one (three colonies) and four SNPs (one colony). Actually, the number of colonies without any SNP was higher for clones growing in galactose than for clones growing in glucose. Altogether, five transitions for seven transversions were found (ratio: 0.71), a proportion slightly higher than expected for transitions (expected ratio: 0.61), but figures are small. Insertions and deletions (Indels) of one base pair in non-monotonous DNA are expected to be ten times less frequent than base substitutions. Indeed, we only found one deletion of a GC dinucleotide in an intergenic region. However, six indels were found in monotonous poly-A/T stretches, but more importantly no mutation was detected in any of the naturally occurring (at least five triplet long) 88 CAG/CTG trinucleotide repeats of the S288C genome. All indels and five out of twelve SNPs fall within intergenic regions. Out of seven remaining SNPs in coding regions, two are synonymous (third codon base) whereas five are non-synonymous and encode point mutations in five different genes (cf. Tables 3 and 4 below).

TABLE 3 summary of mutations detected in the 15 sequenced colonies; base substitutions:

| Chromosome | Position[1] | Mutation | Location | Codon | Amino acid |
|---|---|---|---|---|---|
| I | 175371 | T->C | Intergene | — | — |
| III | 300201 | C->A | Intergene | — | — |
| IV | 628439 | C->A | RLI1 | GTG->TTG | Val->Leu |
| IV | 1298899 | G->T | SYF1 | GTT->TTT | Val->Phe |
| X | 333003 | A->T | ZAP1 | ACT->ACA | Synonymous |
| X | 626414 | T->C | ECM27 | TTT->CTT | Phe->Leu |
| XI | 142750 | C->T | PIR1 | CCG->CCA | Synonymous |
| XI | 315846 | T->G | Intergene | — | — |
| XI | 609033 | A->G | PXL1 | CAG->CGG | Gln->Arg |
| XII | 823062 | A->C | Intergene | — | — |
| XIII | 330662 | C->G | Intergene | — | — |
| XV | 1075334 | A->G | YOR389w | AAC->AGC | Asn->Ser |

TABLE 4 summary of mutations detected in the 15 sequenced colonies; insertions/deletions:

| Chromosome | Position[1] | Mutation | Sequence | Location |
|---|---|---|---|---|
| I | 6737 | +A | $(A)_{19}$ SEQ ID NO: 17 | Intergene |
| I | 101282 | +A | $(A)_{24}$ SEQ ID NO: 18 | Intergene |
| II | 809788 | -T | $(T)_{19}$ SEQ ID NO: 19 | Intergene |
| VI | 106271 | +TT | $(T)_{13}$ SEQ ID NO: 20 | Intergene |
| VII | 95081 | -GC | Non monotonous | Intergene |
| VII | 413969 | -GA | $(A)_2G(A)_{12}$ SEQ ID NO: 21 | Intergene |
| XIII | 918118 | +T | $(T)_{19}$ SEQ ID NO: 19 | Intergene |

[1]mutation position according to GENBANK NC_001133 to NC_001148, PLN 06-DEC-2008 yeast genome assembly.

Figure 3D:
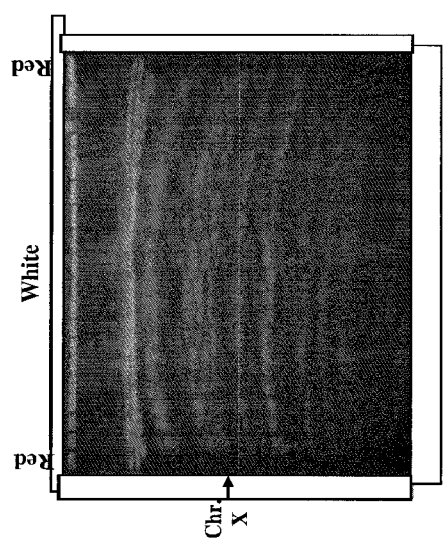

We concluded that expression of a TALEN targeted to a specific CAG/CTG trinucleotide repeat has no effect on other triplet repeats and has no effect on the overall mutation rate of the yeast genome. Since deep-sequencing cannot reveal reciprocal translocations that could be induced by the TALEN, as a last control experiment, a PFGE was run on the heterozygous SUP4-opa1/sup4-opa1::CAG strain. DNA from two colonies grown on glucose and 20 colonies grown on galactose was prepared embedded in agarose plugs and loaded on a PFGE. All karyotypes were normal, showing no evidence for aneuploidies, large segmental duplications or translocations (FIG. 3D).

TALEN expression leads to trinucleotide repeat contractions with a 100% efficacy, giving rise to survivors containing homozygous or heterozygous shorter alleles.

Detailed Material, Methods & Results:

Plasmid pCLS9996 (marked with KANMX) and plasmid pCLS16715 (marked with LEU2), carrying the two TALEN arms were respectively transformed into GFY40 strain (MATa ura3Δ851 leu2Δ1 his3Δ200 lys2Δ202 ade2-opa1 SUP4-opa1; cf. Richard et al. 1999) or GFY6162-3D (MATα ura3Δ851 leu2Δ1 his3Δ200 trp1Δ65 ade2-opa1 sup4-(CAG); cf. Richard et al. 2003). Please see FIG. 1A.

Plasmid pCLS9996 has been deposited at the C.N.C.M. under the terms of the Budapest Treaty [C.N.C.M. deposit number: I-4804; deposit date under the terms of the Budapest Treaty: 10 Oct. 2013].

Plasmid pCLS16715 has also been deposited at the C.N.C.M. under the terms of the Budapest Treaty [C.N.C.M. deposit number: I-4805; deposit date under the terms of the Budapest Treaty: 10 Oct. 2013].

Plasmid pCLS9996 codes for the right-hand TALEN monomer that binds to the DNA target site of SEQ ID NO: 10 (cf. FIG. 1B).

Plasmid pCLS16715 codes for the left-hand TALEN monomer that binds to the DNA target site of SEQ ID NO: 4 (cf. FIG. 1B).

Haploids were crossed and diploids containing both TALEN arms were selected on SC-Leu supplemented with G418 sulfate (200 µg/ml).

As a control, the split-TALEN left arm carried by pCLS9984 (marked with LEU2) was transformed in GFY6162-3D, crossed to GFY40 carrying the TALEN right arm, and diploids were selected as before.

Figure 4:
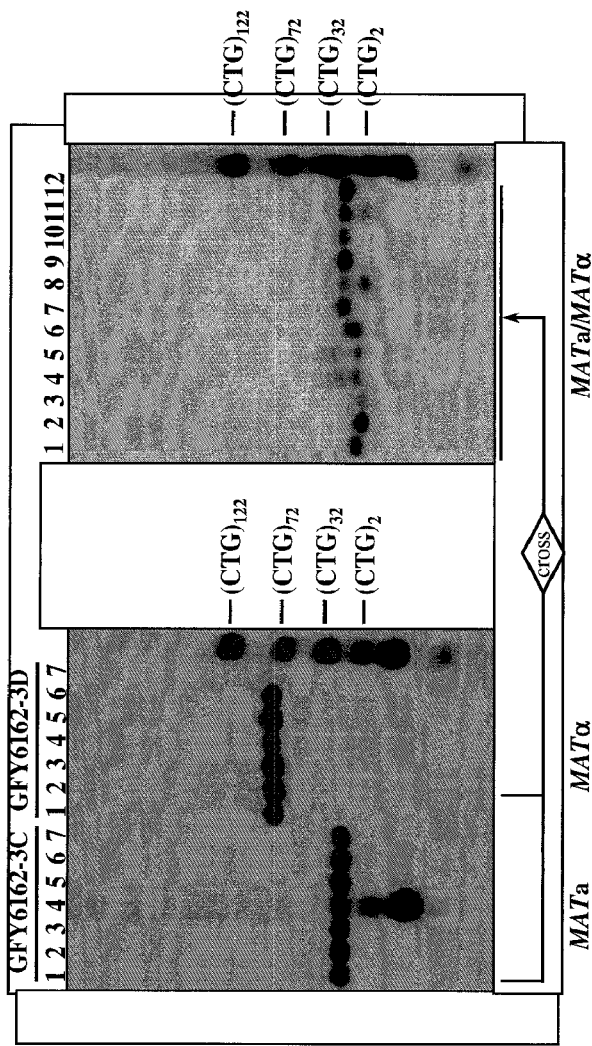
FIG. 4: Southern blots (left: strains GFY6161-3C (MATa leu2Δ1 his3Δ200 lys2Δ202 ade2-opa1 sup4::(CAG)$_{30}$) and GFY6162-3D; right: transformants GFY6162-3C/1 and GFY6162-3D/2).

Repeat lengths were checked by Southern blot in several independent diploids before galactose induction (cf. FIG. 4 and the associated comments below).

The TALEN is normally repressed on glucose medium, one copy of the active SUP4 tRNA being insufficient to suppress the ade2-opa1 mutation, yeast cells are red (cf. Richard et al., 1999, Richard et al., 2000, Richard et al., 2003). In the presence of galactose, the TALEN is expressed, binds CAG/CTG trinucleotide repeats and induces a double-strand break (DSB) into the repeat tract. If a second copy of an active SUP4 tRNA is generated during double-strand break repair, the ade2-opa1 mutation will be suppressed and yeast cells will now be white (cf. FIG. 1A).

Sequences recognized by both TALE DNA-binding domains and by the split-TALE.

The length of the spacer, which is appropriate to induce a DSB was deduced from repeat tract lengths analyzed in surviving cells after TALEN induction (length of 18 bp); cf. FIG. 1B).

Sequence Data for Plasmid PCLs9996 (C.N.C.M. I-4804):

The sequence of the insert carried by plasmid pCLS9996 is:

[SEQ ID NO: 1]
GCGCACATTTCCCCGAAAAGTGCCACCTGACGTCCGATCAAAAATCATCG
CTTCGCTGATTAATTACCCCAGAAATAAGGCTAAAAAACTAATCGCATTA
TCATCCTATGGTTGTTAATTTGATTCGTTCATTTGAAGGTTTGTGGGCC
AGGTTACTGCCAATTTTTCCTCTTCATAACCATAAAAGCTAGTATTGTAG
AATCTTTATTGTTCGGAGCAGTGCGGCGCGAGGCACATCTGCGTTTCAGG
AACGCGACCGGTGAAGACGAGGACGCACGGAGGAGAGTCTTCCTTCGGAG
GGCTGTCACCCGCTCGGCGGCTTCTAATCCGTACTTCAATATAGCAATGA
GCAGTTAAGCGTATTACTGAAAGTTCCAAAGAGAAGGTTTTTTTAGGCTA
ATCGACCTCGAGCAGATCCGCCAGGCGTGTATATAGCGTGGATGCCAGG
CAACTTTAGTGCTGACACATACAGGCATATATATATGTGTGCGACGACAC
ATGATCATATGGCATGCATGTGCTCTGTATGTATATAAAACTCTTGTTTT
CTTCTTTTCTCTAAATATTCTTTCCTTATACATTAGGTCCTTTGTAGCAT
AAATTACTATACTTCTATAGACACGCAAACACAAATACACAGCGGCCTTG
CCACCATGGGCGATCCTAAAAAGAAACGTAAGGTCATCGATAAGGAGACC
GCCGCTGCCAAGTTCGAGAGACAGCACATGGACAGCATCGATATCGCCGA
TCTACGCACGCTCGGCTACAGCCAGCAGCAACAGGAGAAGATCAAACCGA
AGGTTCGTTCGACAGTGGCGCAGCACCACGAGGCACTGGTCGGCCACGGG
TTTACACACGCGCACATCGTTGCGTTAAGCCAACACCCGGCAGCGTTAGG
GACCGTCGCTGTCAAGTATCAGGACATGATCGCAGCGTTGCCAGAGGCGA
CACACGAAGCGATCGTTGGCGTCGGCAAACAGTGGTCCGGCGCACGCGCT

CTGGAGGCCTTGCTCACGGTGGCGGGAGAGTTGAGAGGTCCACCGTTACA
GTTGGACACAGGCCAACTTCTCAAGATTGCAAAACGTGGCGGCGTGACCG
CAGTGGAGGCAGTGCATGCATGGCGCAATGCACTGACGGGTGCCCCGCTC
AACTTGACCCCCCAGCAGGTGGTGGCCATCGCCAGCAATAATGGTGGCAA
GCAGGCGCTGGAGACGGTCCAGCGGCTGTTGCCGGTGCTGTGCCAGGCCC
ACGGCTTGACCCCGGAGCAGGTGGTGGCCATCGCCAGCCACGATGGCGGC
AAGCAGGCGCTGGAGACGGTCCAGCGGCTGTTGCCGGTGCTGTGCCAGGC
CCACGGCTTGACCCCCCAGCAGGTGGTGGCCATCGCCAGCAATGGCGGTG
GCAAGCAGGCGCTGGAGACGGTCCAGCGGCTGTTGCCGGTGCTGTGCCAG
GCCCACGGCTTGACCCCCCAGCAGGTGGTGGCCATCGCCAGCAATAATGG
TGGCAAGCAGGCGCTGGAGACGGTCCAGCGGCTGTTGCCGGTGCTGTGCC
AGGCCCACGGCTTGACCCCGGAGCAGGTGGTGGCCATCGCCAGCCACGAT
GGCGGCAAGCAGGCGCTGGAGACGGTCCAGCGGCTGTTGCCGGTGCTGTG
CCAGGCCCACGGCTTGACCCCCCAGCAGGTGGTGGCCATCGCCAGCAATG
GCGGTGGCAAGCAGGCGCTGGAGACGGTCCAGCGGCTGTTGCCGGTGCTG
TGCCAGGCCCACGGCTTGACCCCCCAGCAGGTGGTGGCCATCGCCAGCAA
TAATGGTGGCAAGCAGGCGCTGGAGACGGTCCAGCGGCTGTTGCCGGTGC
TGTGCCAGGCCCACGGCTTGACCCCGGAGCAGGTGGTGGCCATCGCCAGC
CACGATGGCGGCAAGCAGGCGCTGGAGACGGTCCAGCGGCTGTTGCCGGT
GCTGTGCCAGGCCCACGGCTTGACCCCCAGCAGGTGGTGGCCATCGCCA
GCAATGGCGGTGGCAAGCAGGCGCTGGAGACGGTCCAGCGGCTGTTGCCG
GTGCTGTGCCAGGCCCACGGCTTGACCCCCAGCAGGTGGTGGCCATCGC
CAGCAATAATGGTGGCAAGCAGGCGCTGGAGACGGTCCAGCGGCTGTTGC
CGGTGCTGTGCCAGGCCCACGGCTTGACCCCGGAGCAGGTGGTGGCCATC
GCCAGCCACGATGGCGGCAAGCAGGCGCTGGAGACGGTCCAGCGGCTGTT
GCCGGTGCTGTGCCAGGCCCACGGCTTGACCCCCCAGCAGGTGGTGGCCA
TCGCCAGCAATGGCGGTGGCAAGCAGGCGCTGGAGACGGTCCAGCGGCTG
TTGCCGGTGCTGTGCCAGGCCCACGGCTTGACCCCCCAGCAGGTGGTGGC
CATCGCCAGCAATAATGGTGGCAAGCAGGCGCTGGAGACGGTCCAGCGGC
TGTTGCCGGTGCTGTGCCAGGCCCACGGCTTGACCCCGGAGCAGGTGGTG
GCCATCGCCAGCCACGATGGCGGCAAGCAGGCGCTGGAGACGGTCCAGCG
GCTGTTGCCGGTGCTGTGCCAGGCCCACGGCTTGACCCCCCAGCAGGTGG
TGGCCATCGCCAGCAATGGCGGTGGCAAGCAGGCGCTGGAGACGGTCCAG
CGGCTGTTGCCGGTGCTGTGCCAGGCCCACGGCTTGACCCCTCAGCAGGT
GGTGGCCATCGCCAGCAATGGCGGCGGCAGGCCGGCGCTGGAGAGCATTG
TTGCCCAGTTATCTCGCCCTGATCCGGCGTTGGCCGCGTTGACCAACGAC
CACCTCGTCGCCTTGGCCTGCCTCGGCGGGCGTCCTGCGCTGGATGCAGT
GAAAAAGGGATTGGGGGATCCTATCAGCCGTTCCCAGCTGGTGAAGTCCG
AGCTGGAGGAGAAGAAATCCGAGTTGAGGCACAAGCTGAAGTACGTGCCC
CACGAGTACATCGAGCTGATCGAGATCGCCCGGAACAGCACCCAGGACCG

```
TATCCTGGAGATGAAGGTGATGGAGTTCTTCATGAAGGTGTACGGCTACA
GGGGCAAGCACCTGGGCGGCTCCAGGAAGCCCGACGGCGCCATCTACACC
GTGGGCTCCCCCATCGACTACGGCGTGATCGTGGACACCAAGGCCTACTC
CGGCGGCTACAACCTGCCCATCGGCCAGGCCGACGAAATGCAGAGGTACG
TGGAGGAGAACCAGACCAGGAACAAGCACATCAACCCCAACGAGTGGTGG
AAGGTGTACCCCTCCAGCGTGACCGAGTTCAAGTTCCTGTTCGTGTCCGG
CCACTTCAAGGGCAACTACAAGGCCCAGCTGACCAGGCTGAACCACATCA
CCAACTGCAACGGCGCCGTGCTGTCCGTGGAGGAGCTCCTGATCGGCGGC
GAGATGATCAAGGCCGGCACCCTGACCCTGGAGGAGGTGAGGAGGAAGTT
CAACAACGGCGAGATCAACTTCGCGGCCGACTGATAACTCGAGCGATCCT
CTAGACGAGCTCCTCGAGCCTGCAGCAGCTGAAGCTTTGGACTTCTTCGC
CAGAGGTTTGGTCAAGTCTCCAATCAAGGTTGTCGGCTTGTCTACCTTGC
CAGAAATTTACGAAAAGATGGAAAAGGGTCAAATCGTTGGTAGATACGTT
GTTGACACTTCTAAATAAGCGAATTTCTTATGATTTATGATTTTTATTAT
TAAATAAGTTATAAAAAAAATAAGTGTATACAAATTTTAAAGTGACTCTT
AGGTTTTAAAACGAAAATTCTTATTCTTGAGTAACTCTTTCCTGTAGGTC
AGGTTGCTTTCTCAGGTATAGCATGAGGTCGCTCTTATTGACCACACCTC
TACCGGCATGCAAGCTTGGCGTAATCATGGTCATAGCTGTTTCCTGTGTG
AAATTGTTATCCGCTCACAATTCCACACAACATACGAGCCGGAAGCATAA
AGTGTAAAGCCTGGGGTGCCTAATGAGTGAGCTAACTCACATTAATTGCG
TTGCGCTCACTGCCCGCTTTCCAGTCGGGAAACCTGTCGTGCCAGCAGAT
CTGTTTAGCTTGCCTCGTCCCCGCCGGGTCACCCGGCCAGCGACATGGAG
GCCCAGAATACCCTCCTTGACAGTCTTGACGTGCGCAGCTCAGGGGCATG
ATGTGACTGTCGCCCGTACATTTAGCCCATACATCCCCATGTATAATCAT
TTGCATCCATACATTTTGATGGCCGCACGGCGCGAAGCAAAAATTACGGC
TCCTCGCTGCAGACCTGCGAGCAGGGAAACGCTCCCCTCACAGACGCGTT
GAATTGTCCCCACGCCGCGCCCCTGTAGAGAAATATAAAAGGTTAGGATT
TGCCACTGAGGTTCTTCTTTCATATACTTCCTTTTAAAATCTTGCTAGGA
TACAGTTCTCACATCACATCCGAACATAAACAACCATGCATGGGTAAGGA
AAAGACTCACGTTTCGAGGCCGCGATTAAATTCCAACATGGATGCTGATT
TATATGGGTATAAATGGGCTCGCGATAATGTCGGGCAATCAGGTGCGACA
ATCTATCGATTGTATGGGAAGCCCGATGCGCCAGAGTTGTTTCTGAAACA
TGGCAAAGGTAGCGTTGCCAATGATGTTACAGATGAGATGGTCAGACTAA
ACTGGCTGACGGAATTTATGCCTCTTCCGACCATCAAGCATTTTATCCGT
ACTCCTGATGATGCATGGTTACTCACCACTGCGATCCCCGGCAAAACAGC
ATTCCAGGTATTAGAAGAATATCCTGATTCAGGTGAAAATATTGTTGATG
CGCTGGCAGTGTTCCTGCGCCGGTTGCATTCGATTCCTGTTTGTAATTGT
CCTTTTAACAGCGATCGCGTATTTCGCCTCGCTCAGGCGCAATCACGAAT
GAATAACGGTTTGGTTGATGCGAGTGATTTTGATGACGAGCGTAATGGCT
GGCCTGTTGAACAAGTCTGGAAAGAAATGCATAAGCTTTTGCCATTCTCA
CCGGATTCAGTCGTCACTCATGGTGATTTCTCACTTGATAACCTTATTTT
TGACGAGGGGAAATTAATAGGTTGTATTGATGTTGGACGAGTCGGAATCG
CAGACCGATACCAGGATCTTGCCATCCTATGGAACTGCCTCGGTGAGTTT
TCTCCTTCATTACAGAAACGGCTTTTTCAAAAATATGGTATTGATAATCC
TGATATGAATAAATTGCAGTTTCATTTGATGCTCGATGAGTTTTTCTAAT
CAGTACTGACAATAAAAAGATTCTTGTTTTCAAGAACTTGTCATTTGTAT
AGTTTTTTATATTGTAGTTGTTCTATTTTAATCAAATGTTAGCGTGATT
TATATTTTTTTTCGCCTCGACATCATCTGCCCAGATGCGAAGTTAAGTGC
GCAGAAAGTAATATCATGCGTCAATCGTATGTGAATGCTGGTCGCTATAC
TGCTGTCGATTCGATACTAACGCCGCCATCCAGTGTCGAAAACGAGCTCG
AATTCATCGATATCAGATCCACTAGTGGCCTATGCGACCGCGGATCT
GCCGGTCTCCCTATAGTGAGTCGTATTAATTTCGATAAGCCAGGTTAACC
TGCATTAATGAATCGGCCAACGCGCGGGGAGAGGCGGTTTGCGTATTGGG
CGCTCTTCCGCTTCCTCGCTCACTGACTCGCTGCGCTCGGTCGTTCGGCT
GCGGCGAGCGGTATCAGCATCGATGAATTCCACGGACTATAGACTATACT
AGTATACTCCGTCTACTGTACGATACACTTCCGCTCAGGTCCTTGTCCTT
TAACGAGGCCTTACCACTCTTTTGTTACTCTATTGATCCAGCTCAGCAAA
GGCAGTGTGATCTAAGATTCTATCTTCGCGATGTAGTAAAACTAGCTAGA
CCGAGAAAGAGACTAGAAATGCAAAAGGCACTTCTACAATGGCTGCCATC
ATTATTATCCGATGTGACGCTGCAGCTTCTCAATGATATTCGAATACGCT
TTGAGGAGATACAGCCTAATATCCGACAAACTGTTTTACAGATTTACGAT
CGTACTTGTTACCCATCATTGAATTTTGAACATCCGAACCTGGGAGTTTT
CCCTGAAACAGATAGTATATTTGAACCTGTATAATAATATAGTCTAGC
GCTTTACGGAAGACAATGTATGTATTTCGGTTCCTGGAGAAACTATTGCA
TCTATTGCATAGGTAATCTTGCACGTCGCATCCCCGGTTCATTTTCTGCG
TTTCCATCTTGCACTTCAATAGCATATCTTTGTTAACGAAGCATCTGTGC
TTCATTTTGTAGAACAAAAATGCAACGCGAGAGCGCTAATTTTTCAAACA
AAGAATCTGAGCTGCATTTTTACAGAACAGAAATGCAACGCGAAAGCGCT
ATTTTACCAACGAAGAATCTGTGCTTCATTTTTGTAAAACAAAAATGCAA
CGCGAGAGCGCTAATTTTTCAAACAAAGAATCTGAGCTGCATTTTTACAG
AACAGAAATGCAACGCGAGAGCGCTATTTTACCAACAAAGAATCTATACT
TCTTTTTTGTTCTACAAAAATGCATCCCGAGAGCGCTATTTTTCTAACAA
AGCATCTTAGATTACTTTTTTTCTCCTTTGTGCGCTCTATAATGCAGTCT
CTTGATAACTTTTGCACTGTAGGTCCGTTAAGGTTAGAAGAAGGCTACT
TTGGTGTCTATTTTCTCTTCCATAAAAAAAGCCTGACTCCACTTCCCGCG
TTTACTGATTACTAGCGAAGCTGCGGGTGCATTTTTTCAAGATAAAGGCA
TCCCCGATTATATTCTATACCGATGTGGATTGCGCATACTTTGTGAACAG
AAAGTGATAGCGTTGATGATTCTTCATTGGTCAGAAAATTATGAACGGTT
TCTTCTATTTTGTCTCTATATACTACGTATAGGAAATGTTTACATTTTCG
TATTGTTTTCGATTCACTCTATGAATAGTTCTTACTACAATTTTTTTGTC
TAAAGAGTAATACTAGAGATAAACATAAAAAATGTAGAGGTCGAGTTTAG
```

-continued
ATGCAAGTTCAAGGAGCGAAAGGTGGATGGGTAGGTTATATAGGGATATA

GCACAGAGATATATAGCAAAGAGATACTTTTGAGCAATGTTTGTGGAAGC

GGTATTCGCAATATTTTAGTAGCTCGTTACAGTCCGGTGCGTTTTTGGTT

TTTTGAAAGTGCGTCTTCAGAGCGCTTTTGGTTTTCAAAAGCGCTCTGAA

GTTCCTATACTTTCTAGAGAATAGGAACTTCGGAATAGGAACTTCAAAGC

GTTTCCGAAAACGAGCGCTTCCGAAAATGCAACGCGAGCTGCGCACATAC

AGCTCACTGTTCACGTCGCACCTATATCTGCGTGTTGCCTGTATATATAT

ATACATGAGAAGAACGGCATAGTGCGTGTTTATGCTTAAATGCGTACTTA

TATGCGTCTATTTATGTAGGATGAAAGGTAGTCTAGTACCTCCTGTGATA

TTATCCCATTCCATGCGGGGTATCGTATGCTTCCTTCAGCACTACCCTTT

AGCTGTTCTATATGCTGCCACTCCTCAATTGGATTAGTCTCATCCTTCAA

TGCTATCATTTCCTTTGATATTGGATCATATGCATAGTACCGAGAAACTA

GTGCGAAGTAGTGATCAGGTATTGCTGTTATCTGATGAGTATACGTTGTC

CTGGCCACGGCAGAAGCACGCTTATCGCTCCAATTTCCCACAACATTAGT

CAACTCCGTTAGGCCCTTCATTGAAAGAAATGAGGTCATCAAATGTCTTC

CAATGTGAGATTTTGGGCCATTTTTTATAGCAAAGATTGAATAAGGCGCA

TTTTTCTTCAAAGCTTTATTGTACGATCTGACTAAGTTATCTTTTAATAA

TTGGTATTCCTGTTTATTGCTTGAAGAATTGCCGGTCCTATTTACTCGTT

TTAGGACTGGTTCAGAATTCATCGATGCTCACTCAAAGGTCGGTAATACG

GTTATCCACAGAATCAGGGGATAACGCAGGAAAGAACATGTGAGCAAAAG

GCCAGCAAAAGGCCAGGAACCGTAAAAAGGCCGCGTTGCTGGCGTTTTTC

CATAGGCTCCGCCCCCCTGACGAGCATCACAAAAATCGACGCTCAAGTCA

GAGGTGGCGAAACCCGACAGGACTATAAAGATACCAGGCGTTTCCCCCTG

GAAGCTCCCTCGTGCGCTCTCCTGTTCCGACCCTGCCGCTTACCGGATAC

CTGTCCGCCTTTCTCCCTTCGGGAAGCGTGGCGCTTTCTCATAGCTCACG

CTGTAGGTATCTCAGTTCGGTGTAGGTCGTTCGCTCCAAGCTGGGCTGTG

TGCACGAACCCCCCGTTCAGCCCGACCGCTGCGCCTTATCCGGTAACTAT

CGTCTTGAGTCCAACCCGGTAAGACACGACTTATCGCCACTGGCAGCAGC

CACTGGTAACAGGATTAGCAGAGCGAGGTATGTAGGCGGTGCTACAGAGT

TCTTGAAGTGGTGGCCTAACTACGGCTACACTAGAAGGACAGTATTTGGT

ATCTGCGCTCTGCTGAAGCCAGTTACCTTCGGAAAAAGAGTTGGTAGCTC

TTGATCCGGCAAACAAACCACCGCTGGTAGCGGTGGTTTTTTTGTTTGCA

AGCAGCAGATTACGCGCAGAAAAAAAGGATCTCAAGAAGATCCTTTGATC

TTTTCTACGGGGTCTGACGCTCAGTGGAACGAAAACTCACGTTAAGGGAT

TTTGGTCATGAGCGGATACATATTTGAATGTATTTAGAAAAATAAACAAA

TAGGGGTTCC

The nucleic acid of SEQ ID NO: 1 (carried by plasmid pCLS9996) codes for the TALEN arm that binds to the DNA target site of SEQ ID NO: 10 (cf. FIG. 1B). Hence, the nucleic acid of SEQ ID NO: 1 comprises a sequence, which codes for adjacent units of TAL effector tandem repeat that determine recognition of the DNA target site of SEQ ID NO: 10, and which codes for an endonuclease. The endonuclease is the monomer of a dimeric endonuclease, i.e., a FokI monomer. The sequence, which codes for adjacent units of TAL effector tandem repeat and for an endonuclease, is preceded by a promoter and an enhancer, and is followed by a terminator. The nucleic acid of SEQ ID NO: 1 further comprises a sequence, which codes for a selection marker, i.e., the kanamycin selection marker. The sequence, which codes for the selection marker, is preceded by a promoter and is followed by a terminator.

The nucleic acid of SEQ ID NO: 1 further comprises a replication origin, i.e., the 2-micron replication origin.

More particularly, the nucleic acid of SEQ ID NO: 1 (carried by plasmid pCLS9996) comprises:
  a GAL10 enhancer at positions 36-401 [SEQ ID NO: 37];
  a CYC1 promoter at positions 402-641 [SEQ ID NO: 38];
  a sequence coding for a TALEN arm (TALEN arm that binds to the DNA target site of SEQ ID NO: 10) at positions 656-3484 [SEQ ID NO: 39];
  an ADH1 terminator at positions 3836-4155 [SEQ ID NO: 40];
  a TEF promoter at positions 4357-4736 [SEQ ID NO: 41];
  a sequence coding for the KANMX selection marker at positions 4740-5546 [SEQ ID NO: 42];
  a TEF terminator at positions 5547-5759 [SEQ ID NO: 43]; and
  the 2-micron replication origin at positions 6585-7929 [SEQ ID NO: 44].

Hence, the sequences of SEQ ID NOs: 37-44 are:

(GAL10 enhancer)
SEQ ID NO: 37
GATCAAAAATCATCGCTTCGCTGATTAATTACCCCAGAAATAAGGCTAAA

AAACTAATCGCATTATCATCCTATGGTTGTTAATTTGATTCGTTCATTTG

AAGGTTTGTGGGGCCAGGTTACTGCCAATTTTTCCTCTTCATAACCATAA

AAGCTAGTATTGTAGAATCTTTATTGTTCGGAGCAGTGCGGCGCGAGGCA

CATCTGCGTTTCAGGAACGCGACCGGTGAAGACGAGGACGCACGGAGGAG

AGTCTTCCTTCGGAGGGCTGTCACCCGCTCGGCGGCTTCTAATCCGTACT

TCAATATAGCAATGAGCAGTTAAGCGTATTACTGAAAGTTCCAAAGAGAA

GGTTTTTTTAGGCTAA (CYC1 promoter)
SEQ ID NO: 38
TCGACCTCGAGCAGATCCGCCAGGCGTGTATATAGCGTGGATGGCCAGGC

AACTTTAGTGCTGACACATACAGGCATATATATATGTGTGCGACGACACA

TGATCATATGGCATGCATGTGCTCTGTATGTATATAAAACTCTTGTTTTC

TTCTTTTCTCTAAATATTCTTTCCTTATACATTAGGTCCTTTGTAGCATA

AATTACTATACTTCTATAGACACGCAAACACAAATACACA (coding for the TALEN arm that recognizes the DNA target site of SEQ ID NO: 10)
SEQ ID NO: 39
ATGGGCGATCCTAAAAAGAAACGTAAGGTCATCGATAAGGAGACCGCCGC

TGCCAAGTTCGAGAGACAGCACATGGACAGCATCGATATCGCCGATCTAC

GCACGCTCGGCTACAGCCAGCAGCAACAGGAGAAGATCAAACCGAAGGTT

CGTTCGACAGTGGCGCAGCACCACGAGGCACTGGTCGGCCACGGGTTTAC

ACACGCGCACATCGTTGCGTTAAGCCAACACCCGGCAGCGTTAGGGACCG

TCGCTGTCAAGTATCAGGACATGATCGCAGCGTTGCCAGAGGCGACACAC

GAAGCGATCGTTGGCGTCGGCAAACAGTGGTCCGGCGCACGCGCTCTGGA

GGCCTTGCTCACGGTGGCGGGAGAGTTGAGAGGTCCACCGTTACAGTTGG

ACACAGGCCAACTTCTCAAGATTGCAAAACGTGGCGGCGTGACCGCAGTG

GAGGCAGTGCATGCATGGCGCAATGCACTGACGGGTGCCCCGCTCAACTT

GACCCCCCAGCAGGTGGTGGCCATCGCCAGCAATAATGGTGGCAAGCAGG

CGCTGGAGACGGTCCAGCGGCTGTTGCCGGTGCTGTGCCAGGCCCACGGC

TTGACCCCGGAGCAGGTGGTGGCCATCGCCAGCCACGATGGCGGCAAGCA

GGCGCTGGAGACGGTCCAGCGGCTGTTGCCGGTGCTGTGCCAGGCCCACG

GCTTGACCCCCCAGCAGGTGGTGGCCATCGCCAGCAATGGCGGTGGCAAG

CAGGCGCTGGAGACGGTCCAGCGGCTGTTGCCGGTGCTGTGCCAGGCCCA

CGGCTTGACCCCCAGCAGGTGGTGGCCATCGCCAGCAATAATGGTGGCA

AGCAGGCGCTGGAGACGGTCCAGCGGCTGTTGCCGGTGCTGTGCCAGGCC

CACGGCTTGACCCCGGAGCAGGTGGTGGCCATCGCCAGCCACGATGGCGG

CAAGCAGGCGCTGGAGACGGTCCAGCGGCTGTTGCCGGTGCTGTGCCAGG

CCCACGGCTTGACCCCCAGCAGGTGGTGGCCATCGCCAGCAATGGCGGT

GGCAAGCAGGCGCTGGAGACGGTCCAGCGGCTGTTGCCGGTGCTGTGCCA

GGCCCACGGCTTGACCCCCAGCAGGTGGTGGCCATCGCCAGCAATAATG

GTGGCAAGCAGGCGCTGGAGACGGTCCAGCGGCTGTTGCCGGTGCTGTGC

CAGGCCCACGGCTTGACCCCGGAGCAGGTGGTGGCCATCGCCAGCCACGA

TGGCGGCAAGCAGGCGCTGGAGACGGTCCAGCGGCTGTTGCCGGTGCTGT

GCCAGGCCCACGGCTTGACCCCCCAGCAGGTGGTGGCCATCGCCAGCAAT

GGCGGTGGCAAGCAGGCGCTGGAGACGGTCCAGCGGCTGTTGCCGGTGCT

GTGCCAGGCCCACGGCTTGACCCCCAGCAGGTGGTGGCCATCGCCAGCA

ATAATGGTGGCAAGCAGGCGCTGGAGACGGTCCAGCGGCTGTTGCCGGTG

CTGTGCCAGGCCCACGGCTTGACCCCGGAGCAGGTGGTGGCCATCGCCAG

CCACGATGGCGGCAAGCAGGCGCTGGAGACGGTCCAGCGGCTGTTGCCGG

TGCTGTGCCAGGCCCACGGCTTGACCCCCCAGCAGGTGGTGGCCATCGCC

AGCAATGGCGGTGGCAAGCAGGCGCTGGAGACGGTCCAGCGGCTGTTGCC

GGTGCTGTGCCAGGCCCACGGCTTGACCCCCAGCAGGTGGTGGCCATCG

CCAGCAATAATGGTGGCAAGCAGGCGCTGGAGACGGTCCAGCGGCTGTTG

CCGGTGCTGTGCCAGGCCCACGGCTTGACCCCGGAGCAGGTGGTGGCCAT

CGCCAGCCACGATGGCGGCAAGCAGGCGCTGGAGACGGTCCAGCGGCTGT

TGCCGGTGCTGTGCCAGGCCCACGGCTTGACCCCCCAGCAGGTGGTGGCC

ATCGCCAGCAATGGCGGTGGCAAGCAGGCGCTGGAGACGGTCCAGCGGCT

GTTGCCGGTGCTGTGCCAGGCCCACGGCTTGACCCCTCAGCAGGTGGTGG

CCATCGCCAGCAATGGCGGCGGCAGGCCGGCGCTGGAGAGCATTGTTGCC

CAGTTATCTCGCCCTGATCCGGCGTTGGCCGCGTTGACCAACGACCACCT

CGTCGCCTTGGCCTGCCTCGGCGGCGTCCTGCGCTGGATGCAGTGAAAA

AGGGATTGGGGGATCCTATCAGCCGTTCCCAGCTGGTGAAGTCCGAGCTG

GAGGAGAAGAAATCCGAGTTGAGGCACAAGCTGAAGTACGTGCCCCACGA

GTACATCGAGCTGATCGAGATCGCCCGGAACAGCACCCAGGACCGTATCC

TGGAGATGAAGGTGATGGAGTTCTTCATGAAGGTGTACGGCTACAGGGGC

AAGCACCTGGGCGGCTCCAGGAAGCCCGACGGCGCCATCTACACCGTGGG

CTCCCCCATCGACTACGGCGTGATCGTGGACACCAAGGCCTACTCCGGCG

GCTACAACCTGCCCATCGGCCAGGCCGACGAAATGCAGAGGTACGTGGAG

GAGAACCAGACCAGGAACAAGCACATCAACCCCAACGAGTGGTGGAAGGT

GTACCCCTCCAGCGTGACCGAGTTCAAGTTCCTGTTCGTGTCCGGCCACT

TCAAGGGCAACTACAAGGCCCAGCTGACCAGGCTGAACCACATCACCAAC

TGCAACGGCGCCGTGCTGTCCGTGGAGGAGCTCCTGATCGGCGGCGAGAT

GATCAAGGCCGGCACCCTGACCCTGGAGGAGGTGAGGAGGAAGTTCAACA

ACGGCGAGATCAACTTCGCGGCCGACTGA (ADH1 terminator)
SEQ ID NO: 40
TATTGACCACACCTCTACCGGCATGCAAGCTTGGCGTAATCATGGTCATA

GCTGTTTCCTGTGTGAAATTGTTATCCGCTCACAATTCCACACAACATAC

GAGCCGGAAGCATAAAGTGTAAAGCCTGGGGTGCCTAATGAGTGAGCTAA

CTCACATTAATTGCGTTGCGCTCACTGCCCGCTTTCCAGTCGGGAAACCT

GTCGTGCCAGCAGATCTGTTTAGCTTGCCTCGTCCCCGCCGGGTCACCCG

GCCAGCGACATGGAGGCCCAGAATACCCTCCTTGACAGTCTTGACGTGCG

CAGCTCAGGGGCATGATGTG (TEF promoter)
SEQ ID NO: 41
TGAGGTTCTTCTTTTCATATACTTCCTTTTAAAATCTTGCTAGGATACAGT

TCTCACATCACATCCGAACATAAACAACCATGCATGGGTAAGGAAAAGAC

TCACGTTTCGAGGCCGCGATTAAATTCCAACATGGATGCTGATTTATATG

GGTATAAATGGGCTCGCGATAATGTCGGGCAATCAGGTGCGACAATCTAT

CGATTGTATGGGAAGCCCGATGCGCCAGAGTTGTTTCTGAAACATGGCAA

AGGTAGCGTTGCCAATGATGTTACAGATGAGATGGTCAGACTAAACTGGC

TGACGGAATTTATGCCTCTTCCGACCATCAAGCATTTTATCCGTACTCCT

GATGATGCATGGTTACTCACCACTGCGATCCCC (coding for the KANMX selection marker)
SEQ ID NO: 42
GGCAAAACAGCATTCCAGGTATTAGAAGAATATCCTGATTCAGGTGAAAA

TATTGTTGATGCGCTGGCAGTGTTCCTGCGCCGGTTGCATTCGATTCCTG

TTTGTAATTGTCCTTTTAACAGCGATCGCGTATTTCGCCTCGCTCAGGCG

CAATCACGAATGAATAACGGTTTGGTTGATGCGAGTGATTTTGATGACGA

GCGTAATGGCTGGCCTGTTGAACAAGTCTGGAAAGAAATGCATAAGCTTT

TGCCATTCTCACCGGATTCAGTCGTCACTCATGGTGATTTCTCACTTGAT

AACCTTATTTTTGACGAGGGGAAATTAATAGGTTGTATTGATGTTGGACG

AGTCGGAATCGCAGACCGATACCAGGATCTTGCCATCCTATGGAACTGCC

TCGGTGAGTTTTCTCCTTCATTACAGAAACGGCTTTTTCAAAAATATGGT

ATTGATAATCCTGATATGAATAAATTGCAGTTTCATTTGATGCTCGATGA

GTTTTTCTAATCAGTACTGACAATAAAAAGATTCTTGTTTTCAAGAACTT

GTCATTTGTATAGTTTTTTTATATTGTAGTTGTTCTATTTTAATCAAATG

TTAGCGTGATTTATATTTTTTTTCGCCTCGACATCATCTGCCCAGATGCG

-continued

AAGTTAAGTGCGCAGAAAGTAATATCATGCGTCAATCGTATGTGAATGCT

GGTCGCTATACTGCTGTCGATTCGATACTAACGCCGCCATCCAGTGTCGA

AAACGAGCTCGAATTCATCGATGATATCAGATCCACTAGTGGCCTATGCG

ACCGCGG (TEF terminator)
SEQ ID NO: 43
ATCTGCCGGTCTCCCTATAGTGAGTCGTATTAATTTCGATAAGCCAGGTT

AACCTGCATTAATGAATCGGCCAACGCGCGGGGAGAGGCGGTTTGCGTAT

TGGGCGCTCTTCCGCTTCCTCGCTCACTGACTCGCTGCGCTCGGTCGTTC

GGCTGCGGCGAGCGGTATCAGCATCGATGAATTCCACGGACTATAGACTA

TACTAGTATACTC (2-Micron replication origin)
SEQ ID NO: 44
GCTATTTTTCTAACAAAGCATCTTAGATTACTTTTTTTCTCCTTTGTGCG

CTCTATAATGCAGTCTCTTGATAACTTTTTGCACTGTAGGTCCGTTAAGG

TTAGAAGAAGGCTACTTTGGTGTCTATTTTCTCTTCCATAAAAAAAGCCT

GACTCCACTTCCCGCGTTTACTGATTACTAGCGAAGCTGCGGGTGCATTT

TTTCAAGATAAAGGCATCCCCGATTATATTCTATACCGATGTGGATTGCG

CATACTTTGTGAACAGAAAGTGATAGCGTTGATGATTCTTCATTGGTCAG

AAAATTATGAACGGTTTCTTCTATTTTGTCTCTATATACTACGTATAGGA

AATGTTTACATTTTCGTATTGTTTTCGATTCACTCTATGAATAGTTCTTA

CTACAATTTTTTGTCTAAAGAGTAATACTAGAGATAAACATAAAAAATG

TAGAGGTCGAGTTTAGATGCAAGTTCAAGGAGCGAAAGGTGGATGGGTAG

GTTATATAGGGATATAGCACAGAGATATATAGCAAAGAGATACTTTTGAG

CAATGTTTGTGGAAGCGGTATTCGCAATATTTTAGTAGCTCGTTACAGTC

CGGTGCGTTTTTGGTTTTTTGAAAGTGCGTCTTCAGAGCGCTTTTGGTTT

TCAAAAGCGCTCTGAAGTTCCTATACTTTCTAGAGAATAGGAACTTCGGA

ATAGGAACTTCAAAGCGTTTCCGAAAACGAGCGCTTCCGAAAATGCAACG

CGAGCTGCGCACATACAGCTCACTGTTCACGTCGCACCTATATCTGCGTG

TTGCCTGTATATATATACATGAAGAACGGCATAGTGCGTGTTTATG

CTTAAATGCGTACTTATATGCGTCTATTTATGTAGGATGAAAGGTAGTCT

AGTACCTCCTGTGATATTATCCCATTCCATGCGGGGTATCGTATGCTTCC

TTCAGCACTACCCTTTAGCTGTTCTATATGCTGCCACTCCTCAATTGGAT

TAGTCTCATCCTTCAATGCTATCATTTCCTTTGATATTGGATCATATGCA

TAGTACCGAGAAACTAGTGCGAAGTAGTGATCAGGTATTGCTGTTATCTG

ATGAGTATACGTTGTCCTGGCCACGGCAGAAGCACGCTTATCGCTCCAAT

TTCCCACAACATTAGTCAACTCCGTTAGGCCCTTCATTGAAAGAAATGAG

GTCATCAAATGTCTTCCAATGTGAGATTTTGGGCCATTTTTTATAGCAAA

GATTGAATAAGGCGCATTTTTCTTCAAAGCTTTATTGTACGATCTGACTA

AGTTATCTTTTAATAATTGGTATTCCTGTTTATTGCTTGAAGAAT

In plasmid pCLS9996, the sequence coding for the TALEN arm (SEQ ID NO: 39) comprises:
 a sequence coding for 15 adjacent units of TAL effector tandem repeat, and
 a sequence coding for an endonuclease.

The 15 adjacent units of TAL effector tandem repeat are a N- to C-ordered series of 15 adjacent units each consisting of 34 amino acids. The last C-terminal unit of 34 amino acids is followed by one (truncated) unit of 20 amino acids.

The ordered series of 15 adjacent units determines the recognition of a specific DNA target site (of 15 nucleotides, i.e., of SEQ ID NO: 10), whereas the (truncated) unit of 20 amino acids is not involved in the specific recognition of said DNA target site.

The sequence coding for said 15 adjacent units of 34 amino acids is at positions 499-2028 within the TALEN coding sequence of SEQ ID NO: 39, i.e., is:

[SEQ ID NO: 45]
TTGACCCCCAGCAGGTGGTGGCCATCGCCAGCAATAATGGTGGCAAGCA

GGCGCTGGAGACGGTCCAGCGGCTGTTGCCGGTGCTGTGCCAGGCCCACG

GCTTGACCCCGGAGCAGGTGGTGGCCATCGCCAGCCACGATGGCGGCAAG

CAGGCGCTGGAGACGGTCCAGCGGCTGTTGCCGGTGCTGTGCCAGGCCCA

CGGCTTGACCCCCAGCAGGTGGTGGCCATCGCCAGCAATGGCGGTGGCA

AGCAGGCGCTGGAGACGGTCCAGCGGCTGTTGCCGGTGCTGTGCCAGGCC

CACGGCTTGACCCCCAGCAGGTGGTGGCCATCGCCAGCAATAATGGTGG

CAAGCAGGCGCTGGAGACGGTCCAGCGGCTGTTGCCGGTGCTGTGCCAGG

CCCACGGCTTGACCCCGGAGCAGGTGGTGGCCATCGCCAGCCACGATGGC

GGCAAGCAGGCGCTGGAGACGGTCCAGCGGCTGTTGCCGGTGCTGTGCCA

GGCCCACGGCTTGACCCCCAGCAGGTGGTGGCCATCGCCAGCAATGGCG

GTGGCAAGCAGGCGCTGGAGACGGTCCAGCGGCTGTTGCCGGTGCTGTGC

CAGGCCCACGGCTTGACCCCCAGCAGGTGGTGGCCATCGCCAGCAATAA

TGGTGGCAAGCAGGCGCTGGAGACGGTCCAGCGGCTGTTGCCGGTGCTGT

GCCAGGCCCACGGCTTGACCCCGGAGCAGGTGGTGGCCATCGCCAGCCAC

GATGGCGGCAAGCAGGCGCTGGAGACGGTCCAGCGGCTGTTGCCGGTGCT

GTGCCAGGCCCACGGCTTGACCCCCAGCAGGTGGTGGCCATCGCCAGCA

ATGGCGGTGGCAAGCAGGCGCTGGAGACGGTCCAGCGGCTGTTGCCGGTG

CTGTGCCAGGCCCACGGCTTGACCCCCAGCAGGTGGTGGCCATCGCCAG

CAATAATGGTGGCAAGCAGGCGCTGGAGACGGTCCAGCGGCTGTTGCCGG

TGCTGTGCCAGGCCCACGGCTTGACCCCGGAGCAGGTGGTGGCCATCGCC

AGCCACGATGGCGGCAAGCAGGCGCTGGAGACGGTCCAGCGGCTGTTGCC

GGTGCTGTGCCAGGCCCACGGCTTGACCCCCAGCAGGTGGTGGCCATCG

CCAGCAATGGCGGTGGCAAGCAGGCGCTGGAGACGGTCCAGCGGCTGTTG

CCGGTGCTGTGCCAGGCCCACGGCTTGACCCCCAGCAGGTGGTGGCCAT

CGCCAGCAATAATGGTGGCAAGCAGGCGCTGGAGACGGTCCAGCGGCTGT

TGCCGGTGCTGTGCCAGGCCCACGGCTTGACCCCGGAGCAGGTGGTGGCC

ATCGCCAGCCACGATGGCGGCAAGCAGGCGCTGGAGACGGTCCAGCGGCT

GTTGCCGGTGCTGTGCCAGGCCCACGGCTTGACCCCCAGCAGGTGGTGG

CCATCGCCAGCAATGGCGGTGGCAAGCAGGCGCTGGAGACGGTCCAGCGG

CTGTTGCCGGTGCTGTGCCAGGCCCACGGC.

The sequence of one of said 15 adjacent units of 34 amino acids (coding sequence comprised in SEQ ID NO: 45) is:

[SEQ ID NO: 46]
LTPQQVVAIASXXGGKQALETVQRLLPVLCQAHG,
or

[SEQ ID NO: 25]
LTPEQVVAIASXXGGKQALETVQRLLPVLCQAHG, wherein XX is the RVD of the unit.

The N- to C-ordered series of RVDs formed by the RVDs respectively contained in the 15 adjacent units of TAL effector tandem repeat is:

NN; HD; NG; NN; HD; NG; NN; HD; NG; NN; HD; NG; NN; HD; NG.

The N- to C-ordered series of RVDs determines the recognition of the DNA target site of SEQ ID NO: 10, i.e., GCTGCTGCTGCTGCT (cf. Table 5 above; cf. FIG. 1B).

The sequence coding for said truncated unit of 20 amino acids is (positions 2029-2088 within the TALEN coding sequence of SEQ ID NO: 39):

[SEQ ID NO: 47]
TTGACCCCTCAGCAGGTGGTGGCCATCGCCAGCAATGGCGGCGGCAGGCC

GGCGCTGGAG.

The sequence of said unit of 20 amino acids is:

[SEQ ID NO: 48]
LTPQQVVAIASNGGGRPALE.

The sequence coding for the FokI monomer is at positions 2885-3481 within the TALEN coding sequence of SEQ ID NO: 39, i.e., is:

[SEQ ID NO: 3]
cagctggtgaagtccgagctggaggagaagaaatccgagttgaggcacaa gctgaagtacgtgccccacgagtacatcgagctgatcgagatcgcccgga acagcacccaggaccgtatcctggagatgaaggtgatggagttcttcatg aaggtgtacggctacaggggcaagcacctgggcggctccaggaagcccga cggcgccatctacaccgtgggctcccccatcgactacggcgtgatcgtgg acaccaaggcctactccggcggctacaacctgcccatcggccaggccgac gaaatgcagaggtacgtggaggagaaccagaccaggaacaagcacatcaa ccccaacgagtggtggaaggtgtaccccctccagcgtgaccgagttcaagt tcctgttcgtgtccggccacttcaagggcaactacaaggcccagctgacc aggctgaaccacatcaccaactgcaacggcgccgtgctgtccgtggagga gctcctgatcggcggcgagatgatcaaggccggcaccctgaccctggagg aggtgaggaggaagttcaacaacggcgagatcaactttcgcggccgac.

The FokI monomer sequence (coded by the sequence of SEQ ID NO: 3) is:

[SEQ ID NO: 49]
QLVKSELEEKKSELRHKLKYVPHEYIELIEIARNSTQDRILEMKVMEFFM

KVYGYRGKHLGGSRKPDGAIYTVGSPIDYGVIVDTKAYSGGYNLPIGQAD

EMQRYVEENQTRNKHINPNEWWKVYPSSVTEFKFLFVSGHFKGNYKAQLT

RLNHITNCNGAVLSVEELLIGGEMIKAGTLTLEEVRRKFNNGEINFAAD.

SEQUENCE DATA FOR PLASMID
pCLS16715 (C.N.C.M. I-4805):
The sequence of the insert carried by
plasmid pCLS16715 is:

[SEQ ID NO: 2]
GGGTTCCGCGCACATTTCCCCGAAAAGTGCCACCTGACGTCCGATCAAAA

ATCATCGCTTCGCTGATTAATTACCCCAGAAATAAGGCTAAAAAACTAAT

CGCATTATCATCCTATGGTTGTTAATTTGATTCGTTCATTTGAAGGTTTG

TGGGGCCAGGTTACTGCCAATTTTTCCTCTTCATAACCATAAAAGCTAGT

ATTGTAGAATCTTTATTGTTCGGAGCAGTGCGGCGCGAGGCACATCTGCG

TTTCAGGAACGCGACCGGTGAAGACGAGGACGCACGGAGGAGAGTCTTCC

TTCGGAGGGCTGTCACCCGCTCGGCGGCTTCTAATCCGTACTTCAATATA

GCAATGAGCAGTTAAGCGTATTACTGAAAGTTCCAAAGAGAAGGTTTTTT

TAGGCTAATCGACCTCGAGCAGATCCGCCAGGCGTGTATATAGCGTGGAT

GGCCAGGCAACTTTAGTGCTGACACATACAGGCATATATATATGTGTGCG

ACGACACATGATCATATGGCATGCATGTGCTCTGTATGTATATAAAACTC

TTGTTTTCTTCTTTTCTCTAAATATTCTTTCCTTATACATTAGGTCCTTT

GTAGCATAAATTACTATACTTCTATAGACACGCAAACACAAATACACAGC

GGCCTTGCCACCATGGGCGATCCTAAAAAGAAACGTAAGGTCATCGATTA

CCCATACGATGTTCCAGATTACGCTATCGATATCGCCGATCTACGCACGC

TCGGCTACAGCCAGCAGCAACAGGAGAAGATCAAACCGAAGGTTCGTTCG

ACAGTGGCGCAGCACCACGAGGCACTGGTCGGCCACGGGTTTACACACGC

GCACATCGTTGCGTTAAGCCAACACCCGGCAGCGTTAGGGACCGTCGCTG

TCAAGTATCAGGACATGATCGCAGCGTTGCCAGAGGCGACACACGAAGCG

ATCGTTGGCGTCGGCAAACAGTGGTCCGGCGCACGCGCTCTGGAGGCCTT

GCTCACGGTGGCGGGAGAGTTGAGAGGTCCACCGTTACAGTTGGACACAG

GCCAACTTCTCAAGATTGCAAAACGTGGCGGCGTGACCGCAGTGGAGGCA

GTGCATGCATGGCGCAATGCACTGACGGGTGCCCCGCTCAACTTGACCCC

CCAGCAGGTGGTGGCCATCGCCAGCAATAATGGTGGCAAGCAGGCGCTGG

AGACGGTCCAGCGGCTGTTGCCGGTGCTGTGCCAGGCCCACGGCTTGACC

CCCCAGCAGGTGGTGGCCATCGCCAGCAATGGCGGTGGCAAGCAGGCGCT

GGAGACGGTCCAGCGGCTGTTGCCGGTGCTGTGCCAGGCCCACGGCTTGA

CCCCCCAGCAGGTGGTGGCCATCGCCAGCAATAATGGTGGCAAGCAGGCG

CTGGAGACGGTCCAGCGGCTGTTGCCGGTGCTGTGCCAGGCCCACGGCTT

GACCCCGGAGCAGGTGGTGGCCATCGCCAGCAATATTGGTGGCAAGCAGG

CGCTGGAGACGGTGCAGGCGCTGTTGCCGGTGCTGTGCCAGGCCCACGGC

TTGACCCCCCAGCAGGTGGTGGCCATCGCCAGCAATGGCGGTGGCAAGCA

-continued

GGCGCTGGAGACGGTCCAGCGGCTGTTGCCGGTGCTGTGCCAGGCCCACG
GCTTGACCCCGGAGCAGGTGGTGGCCATCGCCAGCCACGATGGCGGCAAG
CAGGCGCTGGAGACGGTCCAGCGGCTGTTGCCGGTGCTGTGCCAGGCCCA
CGGCTTGACCCCGGAGCAGGTGGTGGCCATCGCCAGCCACGATGGCGGCA
AGCAGGCGCTGGAGACGGTCCAGCGGCTGTTGCCGGTGCTGTGCCAGGCC
CACGGCTTGACCCCGGAGCAGGTGGTGGCCATCGCCAGCCACGATGGCGG
CAAGCAGGCGCTGGAGACGGTCCAGCGGCTGTTGCCGGTGCTGTGCCAGG
CCCACGGCTTGACCCCGGAGCAGGTGGTGGCCATCGCCAGCCACGATGGC
GGCAAGCAGGCGCTGGAGACGGTCCAGCGGCTGTTGCCGGTGCTGTGCCA
GGCCCACGGCTTGACCCCGGAGCAGGTGGTGGCCATCGCCAGCCACGATG
GCGGCAAGCAGGCGCTGGAGACGGTCCAGCGGCTGTTGCCGGTGCTGTGC
CAGGCCCACGGCTTGACCCCGGAGCAGGTGGTGGCCATCGCCAGCCACGA
TGGCGGCAAGCAGGCGCTGGAGACGGTCCAGCGGCTGTTGCCGGTGCTGT
GCCAGGCCCACGGCTTGACCCCGGAGCAGGTGGTGGCCATCGCCAGCAAT
ATTGGTGGCAAGCAGGCGCTGGAGACGGTGCAGGCGCTGTTGCCGGTGCT
GTGCCAGGCCCACGGCTTGACCCCCAGCAGGTGGTGGCCATCGCCAGCA
ATAATGGTGGCAAGCAGGCGCTGGAGACGGTCCAGCGGCTGTTGCCGGTG
CTGTGCCAGGCCCACGGCTTGACCCCGGAGCAGGTGGTGGCCATCGCCAG
CCACGATGGCGGCAAGCAGGCGCTGGAGACGGTCCAGCGGCTGTTGCCGG
TGCTGTGCCAGGCCCACGGCTTGACCCCGGAGCAGGTGGTGGCCATCGCC
AGCAATATTGGTGGCAAGCAGGCGCTGGAGACGGTGCAGGCGCTGTTGCC
GGTGCTGTGCCAGGCCCACGGCTTGACCCCTCAGCAGGTGGTGGCCATCG
CCAGCAATGGCGGCGGCAGGCCGGCGCTGGAGAGCATTGTTGCCCAGTTA
TCTCGCCCTGATCCGGCGTTGGCCGCGTTGACCAACGACCACCTCGTCGC
CTTGGCCTGCCTCGGCGGGCGTCCTGCGCTGGATGCAGTGAAAAAGGGAT
TGGGGGATCCTATCAGCCGTTCCCAGCTGGTGAAGTCCGAGCTGGAGGAG
AAGAAATCCGAGTTGAGGCACAAGCTGAAGTACGTGCCCCACGAGTACAT
CGAGCTGATCGAGATCGCCCGGAACAGCACCCAGGACCGTATCCTGGAGA
TGAAGGTGATGGAGTTCTTCATGAAGGTGTACGGCTACAGGGGCAAGCAC
CTGGGCGGCTCCAGGAAGCCCGACGGCGCCATCTACACCGTGGGCTCCCC
CATCGACTACGCGTGATCGTGGACACCAAGGCCTACTCCGGCGGCTACA
ACCTGCCCATCGGCCAGGCCGACGAAATGCAGAGGTACGTGGAGGAGAAC
CAGACCAGGAACAAGCACATCAACCCCAACGAGTGGTGGAAGGTGTACCC
CTCCAGCGTGACCGAGTTCAAGTTCCTGTTCGTGTCCGGCCACTTCAAGG
GCAACTACAAGGCCCAGCTGACCAGGCTGAACCACATCACCAACTGCAAC
GGCGCCGTGCTGTCCGTGGAGGAGCTCCTGATCGGCGGCGAGATGATCAA
GGCCGGCACCCTGACCCTGGAGGAGGTGAGGAGGAAGTTCAACAACGGCG
AGATCAACTTCGCGGCCGACTGATAACTCGAGCGATCCTCTAGACGAGCT
CCTCGAGCCTGCAGCAGCTGAAGCTTTGGACTTCTTCGCCAGAGGTTTGG
TCAAGTCTCCAATCAAGGTTGTCGGCTTGTCTACCTTGCCAGAAATTTAC
GAAAAGATGGAAAAGGGTCAAATCGTTGGTAGATACGTTGTTGACACTTC

-continued

TAAATAAGCGAATTTCTTATGATTTATGATTTTTATTATTAAATAAGTTA
TAAAAAAAATAAGTGTATACAAATTTTAAAGTGACTCTTAGGTTTTAAAA
CGAAAATTCTTATTCTTGAGTAACTCTTTCCTGTAGGTCAGGTTGCTTTC
TCAGGTATAGCATGAGGTCGCTCTTATTGACCACACCTCTACCGGCATGC
AAGCTTGGCGTAATCATGGTCATAGCTGTTTCCTGTGTGAAATTGTTATC
CGCTCACAATTCCACACAACATACGAGCCGGAAGCATAAAGTGTAAAGCC
TGGGGTGCCTAATGAGTGAGCTAACTCACATTAATTGCGTTGCGCTCACT
GCCCGCTTTCCAGTCGGGAAACCTGTCGTGCCAGCAGATCTATTACATTA
TGGGTGGTATGTTGGAATAAAAATCAACTATCATCTACTAACTAGTATTT
ACGTTACTAGTATATTATCATATACGGTGTTAGAAGATGACGCAAATGAT
GAGAAATAGTCATCTAAATTAGTGGAAGCTGAAACGCAAGGATTGATAAT
GTAATAGGATCAATGAATATTAACATATAAAATGATGATAATAATATTTA
TAGAATTGTGTAGAATTGCAGATTCCCTTTTATGGATTCCTAAATCCTCG
AGGAGAACTTCTAGTATATCTACATACCTAATATTATTGCCTTATTAAAA
ATGGAATCCCAACAATTACATCAAAATCCACATTCTCTTCAAAATCAATT
GTCCTGTACTTCCTTGTTCATGTGTGTTCAAAAACGTTATATTTATAGGA
TAATTATACTCTATTTCTCAACAAGTAATTGGTTGTTTGGCCGAGCGGTC
TAAGGCGCCTGATTCAAGAAATATCTTGACCGCAGTTAACTGTGGGAATA
CTCAGGTATCGTAAGATGCAAGAGTTCGAATCTCTTAGCAACCATTATTT
TTTTCCTCAACATAACGAGAACACACAGGGGCGCTATCGCACAGAATCAA
ATTCGATGACTGGAAATTTTTTGTTAATTTCAGAGGTCGCCTGACGCATA
TACCTTTTTCAACTGAAAAATTGGGAGAAAAAGGAAAGGTGAGAGCCGCG
GAACCGGCTTTTCATATAGAATAGAGAAGCGTTCATGACTAAATGCTTGC
ATCACAATACTTGAAGTTGACAATATTATTTAAGGACCTATTGTTTTTTC
CAATAGGTGGTTAGCAATCGTCTTACTTTCTAACTTTTCTTACCTTTTAC
ATTTCAGCAATATATATATATATATTTCAAGGATATACCATTCTAATGTC
TGCCCCTAAGAAGATCGTCGTTTTGCCAGGTGACCACGTTGGTCAAGAAA
TCACAGCCGAAGCCATTAAGGTTCTTAAAGCTATTTCTGATGTTCGTTCC
AATGTCAAGTTCGATTTCGAAAATCATTTAATTGGTGGTGCTGCTATCGA
TGCTACAGGTGTCCCACTTCCAGATGAGGCGCTGGAAGCCTCCAAGAAGG
TTGATGCCGTTTTGTTAGGTGCTGTGGGTGGTCCTAAATGGGGTACCGGT
AGTGTTAGACCTGAACAAGGTTTACTAAAAATCCGTAAAGAACTTCAATT
GTACGCCAACTTAAGACCATGTAACTTTGCATCCGACTCTCTTTTAGACT
TATCTCCAATCAAGCCACAATTTGCTAAAGGTACTGACTTCGTTGTTGTC
AGAGAATTAGTGGGAGGTATTTACTTTGGTAAGAGAAAGGAAGACGATGG
TGATGGTGTCGCTTGGGATAGTGAACAATACACCGTTCCAGAAGTGCAAA
GAATCACAAGAATGGCCGCTTTCATGGCCCTACAACATGAGCCACCATTG
CCTATTTGGTCCTTGGATAAAGCTAATGTTTTGGCCTCTTCAAGATTATG
GAGAAAAACTGTGGAGGAAACCATCAAGAACGAATTCCCTACATTGAAGG
TTCAACATCAATTGATTGATTCTGCCGCCATGATCCTAGTTAAGAACCCA

```
ACCCACCTAAATGGTATTATAATCACCAGCAACATGTTTGGTGATATCAT
CTCCGATGAAGCCTCCGTTATCCCAGGTTCCTTGGGTTTGTTGCCATCTG
CGTCCTTGGCCTCTTTGCCAGACAAGAACACCGCATTTGGTTTGTACGAA
CCATGCCACGGTTCTGCTCCAGATTTGCCAAAGAATAAGGTCAACCCTAT
CGCCACTATCTTGTCTGCTGCAATGATGTTGAAATTGTCATTGAACTTGC
CTGAAGAAGGTAAGGCCATTGAAGATGCAGTTAAAAAGGTTTTGGATGCA
GGTATCAGAACTGGTGATTTAGGTGGTTCCAACAGTACCACGGAAGTCGG
TGATGCTGTCGCCGAAGAAGTTAAGAAAATCCTTGCTTAAAAAGATTCTC
TTTTTTTATGATATTTGTACATAAACTTTATAAATGAAATTCATAATAGA
AACGACACGAAATTACAAAATGGAATATGTTCATAGGGTAGACGAAACTA
TATACGCAATCTACATACATTTATCAAGAAGGAGAAAAGGAGGATGTAA
AGGAATACAGGTAAGCAAATTGATACTAATGGCTCAACGTGATAAGGAAA
AAGAATTGCACTTTAACATTAATATTGACAAGGAGGAGGGCACCACACAA
AAAGTTAGGTGTAACAGAAAATCATGAAACTATGATTCCTAATTTATATA
TTGGAGGATTTTCTCTAAAAAAAAAAAAATACAACAAATAAAAAACACTC
AATGACCTGACCATTTGATGGAGTTTAAGTCAATACCTTCTTGAACCATT
TCCCATAATGGTGAAAGTTCCCTCAAGAATTTTACTCTGTCAGAAACGGC
CTTAACGACGTAGTCGACCTCCTCTTCAGTACTAAATCTACCAATACCAA
ATCTGATGGAAGAATGGGCTAATGCATCATCCTTACCCAGCGCATGTAAA
ACATAAGAAGGTTCTAGGGAAGCAGATGTACAGGCTGAACCCGAGGATAA
TGCGATATCCCTTAGTGCCATCAATAAAGATTCTCCTTCCACGTAGGCGA
AAGAAACGTTAACACACCCTGGATAACGATGATCTGGAGATCCGTTCAAC
GTGGTATGTTCAGCGGATAATAGACCTTTGACTAATTTATCGGATAGTCT
TTTGATGTGAGCTTGGTCGTTGTCAAATTCTTTCTTCATCAATCTCGCAG
CTTCACCAAATCCCGCTACCAATGGGGGGCCAAAGTACCAGATCTGCTG
CATTAATGAATCGGCCAACGCGCGGGAGAGGCGGTTTGCGTATTGGGCG
CTCTTCCGCTTCCTCGCTCACTGACTCGCTGCGCTCGGTCGTTCGGCTGC
GGCGAGCGGTATCAGCATCGATGAATTCCACGGACTATAGACTATACTAG
TATACTCCGTCTACTGTACGATACACTTCCGCTCAGGTCCTTGTCCTTTA
ACGAGGCCTTACCACTCTTTTGTTACTCTATTGATCCAGCTCAGCAAAGG
CAGTGTGATCTAAGATTCTATCTTCGCGATGTAGTAAAACTAGCTAGACC
GAGAAAGAGACTAGAAATGCAAAAGGCACTTCTACAATGGCTGCCATCAT
TATTATCCGATGTGACGCTGCAGCTTCTCAATGATATTCGAATACGCTTT
GAGGAGATACAGCCTAATATCCGACAAACTGTTTTACAGATTTACGATCG
TACTTGTTACCCATCATTGAATTTTGAACATCCGAACCTGGGAGTTTTCC
CTGAAACAGATAGTATATTTGAACCTGTATAATAATATATAGTCTAGCGC
TTTACGAAGACAATGTATGTATTTCGGTTCCTGGAGAAACTATTGCATC
TATTGCATAGGTAATCTTGCACGTCGCATCCCCGGTTCATTTTCTGCGTT
TCCATCTTGCACTTCAATAGCATATCTTTGTTAACGAAGCATCTGTGCTT
CATTTTGTAGAACAAAAATGCAACGCGAGAGCGCTAATTTTTCAAACAAA
GAATCTGAGCTGCATTTTTACAGAACAGAAATGCAACGCGAAAGCGCTAT
TTTACCAACGAAGAATCTGTGCTTCATTTTTGTAAAACAAAAATGCAACG
CGAGAGCGCTAATTTTTCAAACAAAGAATCTGAGCTGCATTTTTACAGAA
CAGAAATGCAACGCGAGAGCGCTATTTTACCAACAAAGAATCTATACTTC
TTTTTTGTTCTACAAAAATGCATCCCGAGAGCGCTATTTTTCTAACAAAG
CATCTTAGATTACTTTTTTTCTCCTTTGTGCGCTCTATAATGCAGTCTCT
TGATAACTTTTTGCACTGTAGGTCCGTTAAGGTTAGAAGAAGGCTACTTT
GGTGTCTATTTTCTCTTCCATAAAAAAGCCTGACTCCACTTCCCGCGTT
TACTGATTACTAGCGAAGCTGCGGGTGCATTTTTTCAAGATAAAGGCATC
CCCGATTATATTCTATACCGATGTGGATTGCGCATACTTTGTGAACAGAA
AGTGATAGCGTTGATGATTCTTCATTGGTCAGAAAATTATGAACGGTTTC
TTCTATTTTGTCTCTATATACTACGTATAGGAAATGTTTACATTTTCGTA
TTGTTTTCGATTCACTCTATGAATAGTTCTTACTACAATTTTTTTGTCTA
AAGAGTAATACTAGAGATAAACATAAAAAATGTAGAGGTCGAGTTTAGAT
GCAAGTTCAAGGAGCGAAAGGTGGATGGGTAGGTTATATAGGGATATAGC
ACAGAGATATATAGCAAAGAGATACTTTTGAGCAATGTTTGTGGAAGCGG
TATTCGCAATATTTTAGTAGCTCGTTACAGTCCGGTGCGTTTTTGGTTTT
TTGAAAGTGCGTCTTCAGAGCGCTTTTGGTTTTCAAAAGCGCTCTGAAGT
TCCTATACTTTCTAGAGAATAGGAACTTCGGAATAGGAACTTCAAAGCGT
TTCCGAAAACGAGCGCTTCCGAAAATGCAACGCGAGCTGCGCACATACAG
CTCACTGTTCACGTCGCACCTATATCTGCGTGTTGCCTGTATATATATAT
ACATGAGAAGAACGGCATAGTGCGTGTTTATGCTTAAATGCGTACTTATA
TGCGTCTATTTATGTAGGATGAAAGGTAGTCTAGTACCTCCTGTGATATT
ATCCCATTCCATGCGGGGTATCGTATGCTTCCTTCAGCACTACCCTTTAG
CTGTTCTATATGCTGCCACTCCTCAATTGGATTAGTCTCATCCTTCAATG
CTATCATTTCCTTTGATATTGGATCATATGCATAGTACCGAGAAACTAGT
GCGAAGTAGTGATCAGGTATTGCTGTTATCTGATGAGTATACGTTGTCCT
GGCCACGGCAGAAGCACGCTTATCGCTCCAATTTCCCACAACATTAGTCA
ACTCCGTTAGGCCCTTCATTGAAAGAAATGAGGTCATCAAATGTCTTCCA
ATGTGAGATTTTGGGCCATTTTTTATAGCAAAGATTGAATAAGGCGCATT
TTTCTTCAAAGCTTTATTGTACGATCTGACTAAGTTATCTTTTAATAATT
GGTATTCCTGTTTATTGCTTGAAGAATTGCCGGTCCTATTTACTCGTTTT
AGGACTGGTTCAGAATTCATCGATGCTCACTCAAAGGTCGGTAATACGGT
TATCCACAGAATCAGGGGATAACGCAGGAAAGAACATGTGAGCAAAGGC
CAGCAAAAGGCCAGGAACCGTAAAAAGGCCGCGTTGCTGGCGTTTTTCCA
TAGGCTCCGCCCCCCTGACGAGCATCACAAAAATCGACGCTCAAGTCAGA
GGTGGCGAAACCCGACAGGACTATAAAGATACCAGGCGTTTCCCCCTGGA
AGCTCCCTCGTGCGCTCTCCTGTTCCGACCCTGCCGCTTACCGGATACCT
GTCCGCCTTTCTCCCTTCGGGAAGCGTGGCGCTTTCTCATAGCTCACGCT
GTAGGTATCTCAGTTCGGTGTAGGTCGTTCGCTCCAAGCTGGGCTGTGTG
CACGAACCCCCCGTTCAGCCCGACCGCTGCGCCTTATCCGGTAACTATCG
```

-continued
```
TCTTGAGTCCAACCCGGTAAGACACGACTTATCGCCACTGGCAGCAGCCA

CTGGTAACAGGATTAGCAGAGCGAGGTATGTAGGCGGTGCTACAGAGTTC

TTGAAGTGGTGGCCTAACTACGGCTACACTAGAAGGACAGTATTTGGTAT

CTGCGCTCTGCTGAAGCCAGTTACCTTCGGAAAAAGAGTTGGTAGCTCTT

GATCCGGCAAACAAACCACCGCTGGTAGCGGTGGTTTTTTTGTTTGCAAG

CAGCAGATTACGCGCAGAAAAAAAGGATCTCAAGAAGATCCTTTGATCTT

TTCTACGGGGTCTGACGCTCAGTGGAACGAAAACTCACGTTAAGGGATTT

TGGTCATGAGATTATCAAAAAGGATCTTCACCTAGATCCTTTTAAATTAA

AAATGAAGTTTTAAATCAATCTAAAGTATATATGAGTAAACTTGGTCTGA

CAGTTACCAATGCTTAATCAGTGAGGCACCTATCTCAGCGATCTGTCTAT

TTCGTTCATCCATAGTTGCCTGACTCCCCGTCGTGTAGATAACTACGATA

CGGGAGGGCTTACCATCTGGCCCCAGTGCTGCAATGATACCGCGAGACCC

ACGCTCACCGGCTCCAGATTTATCAGCAATAAACCAGCCAGCCGGAAGGG

CCGAGCGCAGAAGTGGTCCTGCAACTTTATCCGCCTCCATCCAGTCTATT

AATTGTTGCCGGGAAGCTAGAGTAAGTAGTTCGCCAGTTAATAGTTTGCG

CAACGTTGTTGCCATTGCTACAGGCATCGTGGTGTCACGCTCGTCGTTTG

GTATGGCTTCATTCAGCTCCGGTTCCCAACGATCAAGGCGAGTTACATGA

TCCCCCATGTTGTGCAAAAAAGCGGTTAGCTCCTTCGGTCCTCCGATCGT

TGTCAGAAGTAAGTTGGCCGCAGTGTTATCACTCATGGTTATGGCAGCAC

TGCATAATTCTCTTACTGTCATGCCATCCGTAAGATGCTTTTCTGTGACT

GGTGAGTACTCAACCAAGTCATTCTGAGAATAGTGTATGCGGCGACCGAG

TTGCTCTTGCCCGGCGTCAATACGGGATAATACCGCGCCACATAGCAGAA

CTTTAAAAGTGCTCATCATTGGAAAACGTTCTTCGGGGCGAAAACTCTCA

AGGATCTTACCGCTGTTGAGATCCAGTTCGATGTAACCCACTCGTGCACC

CAACTGATCTTCAGCATCTTTTACTTTCACCAGCGTTTCTGGGTGAGCAA

AAACAGGAAGGCAAAATGCCGCAAAAAAGGGAATAAGGGCGACACGGAAA

TGTTGAATACTCATACTCTTCCTTTTTCAATATTATTGAAGCATTTATCA

GGGTTATTGTCTCATGAGCGGATACATATTTGAATGTATTTAGAAAAATA

AACAAATAG
```

The nucleic acid of SEQ ID NO: 2 (carried by plasmid pCLS16715) codes for the TALEN arm that binds to the DNA target site of SEQ ID NO: 4 (cf. FIG. 1B). Hence, the nucleic acid of SEQ ID NO: 2 comprises a sequence, which codes for adjacent units of TAL effector tandem repeat that determine recognition of the DNA target site of SEQ ID NO: 4, and which codes for an endonuclease. The endonuclease is the monomer of a dimeric endonuclease, i.e., a FokI monomer. The sequence, which codes for adjacent units of TAL effector tandem repeat and for an endonuclease, is preceded by a promoter and an enhancer, and is followed by a terminator. The nucleic acid of SEQ ID NO: 2 further comprises a sequence, which codes for a selection marker, i.e., a leucine selection marker.

The nucleic acid of SEQ ID NO: 2 further comprises a replication origin, i.e., the 2-micron replication origin.

More particularly, the nucleic acid of SEQ ID NO: 2 (carried by plasmid pCLS16715) comprises:
  a GAL10 enhancer at positions 43-408 [SEQ ID NO: 37, as in plasmid pCLS9996];
  a CYC1 promoter at positions 409-648 [SEQ ID NO: 38, as in plasmid pCLS9996];
  a sequence coding for a TALEN arm (TALEN arm that binds to the DNA target site of SEQ ID NO: 4) at positions 663-3476 [SEQ ID NO: 50];
  an ADH1 terminator at positions 3525-3844 [SEQ ID NO: 51];
  a sequence coding for the LEU2 selection marker at positions 4946-6040 [SEQ ID NO: 52];
  the 2-micron replication origin at positions 7583-8927 [SEQ ID NO: 53].

The sequences of SEQ ID NO: 37 (GAL10 enhancer) and of SEQ ID NO: 38 (CYC1 promoter) are described above.
The sequences of SEQ ID NOs: 50-53 are:

```
(coding for the TALEN arm that binds to the
DNA target site of SEQ ID NO: 4)
                                       SEQ ID NO: 50
ATGGGCGATCCTAAAAAGAAACGTAAGGTCATCGATTACCCATACGATGT

TCCAGATTACGCTATCGATATCGCCGATCTACGCACGCTCGGCTACAGCC

AGCAGCAACAGGAGAAGATCAAACCGAAGGTTCGTTCGACAGTGGCGCAG

CACCACGAGGCACTGGTCGGCCACGGGTTTACACACGCGCACATCGTTGC

GTTAAGCCAACACCCGGCAGCGTTAGGGACCGTCGCTGTCAAGTATCAGG

ACATGATCGCAGCGTTGCCAGAGGCGACACACGAAGCGATCGTTGGCGTC

GGCAAACAGTGGTCCGGCGCACGCGCTCTGGAGGCCTTGCTCACGGTGGC

GGGAGAGTTGAGAGGTCCACCGTTACAGTTGGACACAGGCCAACTTCTCA

AGATTGCAAAACGTGGCGGCGTGACCGCAGTGGAGGCAGTGCATGCATGG

CGCAATGCACTGACGGGTGCCCCGCTCAACTTGACCCCCAGCAGGTGGT

GGCCATCGCCAGCAATAATGGTGGCAAGCAGGCGCTGGAGACGGTCCAGC

GGCTGTTGCCGGTGCTGTGCCAGGCCCACGGCTTGACCCCCCAGCAGGTG

GTGGCCATCGCCAGCAATGGCGGTGGCAAGCAGGCGCTGGAGACGGTCCA

GCGGCTGTTGCCGGTGCTGTGCCAGGCCCACGGCTTGACCCCCCAGCAGG

TGGTGGCCATCGCCAGCAATAATGGTGGCAAGCAGGCGCTGGAGACGGTC

CAGCGGCTGTTGCCGGTGCTGTGCCAGGCCCACGGCTTGACCCCGGAGCA

GGTGGTGGCCATCGCCAGCAATATTGGTGGCAAGCAGGCGCTGGAGACGG

TGCAGGCGCTGTTGCCGGTGCTGTGCCAGGCCCACGGCTTGACCCCCCAG

CAGGTGGTGGCCATCGCCAGCAATGGCGGTGGCAAGCAGGCGCTGGAGAC

GGTCCAGCGGCTGTTGCCGGTGCTGTGCCAGGCCCACGGCTTGACCCCGG

AGCAGGTGGTGGCCATCGCCAGCCACGATGGCGGCAAGCAGGCGCTGGAG

ACGGTCCAGCGGCTGTTGCCGGTGCTGTGCCAGGCCCACGGCTTGACCCC

GGAGCAGGTGGTGGCCATCGCCAGCCACGATGGCGGCAAGCAGGCGCTGG

AGACGGTCCAGCGGCTGTTGCCGGTGCTGTGCCAGGCCCACGGCTTGACC

CCGGAGCAGGTGGTGGCCATCGCCAGCCACGATGGCGGCAAGCAGGCGCT

GGAGACGGTCCAGCGGCTGTTGCCGGTGCTGTGCCAGGCCCACGGCTTGA

CCCCGGAGCAGGTGGTGGCCATCGCCAGCCACGATGGCGGCAAGCAGGCG

CTGGAGACGGTCCAGCGGCTGTTGCCGGTGCTGTGCCAGGCCCACGGCTT

GACCCCGGAGCAGGTGGTGGCCATCGCCAGCCACGATGGCGGCAAGCAGG

CGCTGGAGACGGTCCAGCGGCTGTTGCCGGTGCTGTGCCAGGCCCACGGC
```

TTGACCCCGGAGCAGGTGGTGGCCATCGCCAGCCACGATGGCGGCAAGCA
GGCGCTGGAGACGGTCCAGCGGCTGTTGCCGGTGCTGTGCCAGGCCCACG
GCTTGACCCCGGAGCAGGTGGTGGCCATCGCCAGCAATATTGGTGGCAAG
CAGGCGCTGGAGACGGTGCAGGCGCTGTTGCCGGTGCTGTGCCAGGCCCA
CGGCTTGACCCCCAGCAGGTGGTGGCCATCGCCAGCAATAATGGTGGCA
AGCAGGCGCTGGAGACGGTCCAGCGGCTGTTGCCGGTGCTGTGCCAGGCC
CACGGCTTGACCCCGGAGCAGGTGGTGGCCATCGCCAGCCACGATGGCGG
CAAGCAGGCGCTGGAGACGGTCCAGCGGCTGTTGCCGGTGCTGTGCCAGG
CCCACGGCTTGACCCCGGAGCAGGTGGTGGCCATCGCCAGCAATATTGGT
GGCAAGCAGGCGCTGGAGACGGTGCAGGCGCTGTTGCCGGTGCTGTGCCA
GGCCCACGGCTTGACCCCTCAGCAGGTGGTGGCCATCGCCAGCAATGGCG
GCGGCAGGCCGGCGCTGGAGAGCATTGTTGCCCAGTTATCTCGCCCTGAT
CCGGCGTTGGCCGCGTTGACCAACGACCACCTCGTCGCCTTGGCCTGCCT
CGGCGGGCGTCCTGCGCTGGATGCAGTGAAAAAGGGATTGGGGGATCCTA
TCAGCCGTTCCCAGCTGGTGAAGTCCGAGCTGGAGGAGAAGAAATCCGAG
TTGAGGCACAAGCTGAAGTACGTGCCCCACGAGTACATCGAGCTGATCGA
GATCGCCCGGAACAGCACCCAGGACCGTATCCTGGAGATGAAGGTGATGG
AGTTCTTCATGAAGGTGTACGGCTACAGGGGCAAGCACCTGGGCGGCTCC
AGGAAGCCCGACGGCGCCATCTACACCGTGGGCTCCCCCATCGACTACGG
CGTGATCGTGGACACCAAGGCCTACTCCGGCGGCTACAACCTGCCCATCG
GCCAGGCCGACGAAATGCAGAGGTACGTGGAGGAGAACCAGACCAGGAAC
AAGCACATCAACCCCAACGAGTGGTGGAAGGTGTACCCCTCCAGCGTGAC
CGAGTTCAAGTTCCTGTTCGTGTCCGGCCACTTCAAGGGCAACTACAAGG
CCCAGCTGACCAGGCTGAACCACATCACCAACTGCAACGGCGCCGTGCTG
TCCGTGGAGGAGCTCCTGATCGGCGGCGAGATGATCAAGGCCGGCACCCT
GACCCTGGAGGAGGTGAGGAGGAAGTTCAACAACGGCGAGATCAACTTCG
CGGCCGACTGA
(ADH1 terminator)
SEQ ID NO: 51
TTTGGACTTCTTCGCCAGAGGTTTGGTCAAGTCTCCAATCAAGGTTGTCG
GCTTGTCTACCTTGCCAGAAATTTACGAAAAGATGGAAAAGGGTCAAATC
GTTGGTAGATACGTTGTTGACACTTCTAAATAAGCGAATTTCTTATGATT
TATGATTTTTATTATTAAATAAGTTATAAAAAAAATAAGTGTATACAAAT
TTTAAAGTGACTCTTAGGTTTTAAAACGAAAATTCTTATTCTTGAGTAAC
TCTTTCCTGTAGGTCAGGTTGCTTTCTCAGGTATAGCATGAGGTCGCTCT
TATTGACCACACCTCTACCG
(coding for the LEU2 selection marker)
SEQ ID NO: 52
ATGTCTGCCCCTAAGAAGATCGTCGTTTTGCCAGGTGACCACGTTGGTCA
AGAAATCACAGCCGAAGCCATTAAGGTTCTTAAAGCTATTTCTGATGTTC
GTTCCAATGTCAAGTTCGATTTCGAAAATCATTTAATTGGTGGTGCTGCT
ATCGATGCTACAGGTGTCCCACTTCCAGATGAGGCGCTGGAAGCCTCCAA GAAGGTTGATGCCGTTTTGTTAGGTGCTGTGGGTGGTCCTAAATGGGGTA
CCGGTAGTGTTAGACCTGAACAAGGTTTACTAAAAATCCGTAAAGAACTT
CAATTGTACGCCAACTTAAGACCATGTAACTTTGCATCCGACTCTCTTTT
AGACTTATCTCCAATCAAGCCACAATTTGCTAAAGGTACTGACTTCGTTG
TTGTCAGAGAATTAGTGGGAGGTATTTACTTTGGTAAGAGAAAGGAAGAC
GATGGTGATGGTGTCGCTTGGGATAGTGAACAATACACCGTTCCAGAAGT
GCAAAGAATCACAAGAATGGCCGCTTTCATGGCCCTACAACATGAGCCAC
CATTGCCTATTTGGTCCTTGGATAAAGCTAATGTTTTGGCCTCTTCAAGA
TTATGGAGAAAAACTGTGGAGGAAACCATCAAGAACGAATTCCCTACATT
GAAGGTTCAACATCAATTGATTGATTCTGCCGCCATGATCCTAGTTAAGA
ACCCAACCCACCTAAATGGTATTATAATCACCAGCAACATGTTTGGTGAT
ATCATCTCCGATGAAGCCTCCGTTATCCCAGGTTCCTTGGGTTTGTTGCC
ATCTGCGTCCTTGGCCTCTTTGCCAGACAAGAACACCGCATTTGGTTTGT
ACGAACCATGCCACGGTTCTGCTCCAGATTTGCCAAAGAATAAGGTCAAC
CCTATCGCCACTATCTTGTCTGCTGCAATGATGTTGAAATTGTCATTGAA
CTTGCCTGAAGAAGGTAAGGCCATTGAAGATGCAGTTAAAAAGGTTTTGG
ATGCAGGTATCAGAACTGGTGATTTAGGTGGTTCCAACAGTACCACGGAA
GTCGGTGATGCTGTCGCCGAAGAAGTTAAGAAAATCCTTGCTTAA
(2-Micron replication origin)
SEQ ID NO: 53
AACGAAGCATCTGTGCTTCATTTTGTAGAACAAAAATGCAACGCGAGAGC
GCTAATTTTTCAAACAAAGAATCTGAGCTGCATTTTTACAGAACAGAAAT
GCAACGCGAAAGCGCTATTTTACCAACGAAGAATCTGTGCTTCATTTTTG
TAAAACAAAAATGCAACGCGAGAGCGCTAATTTTTCAAACAAAGAATCTG
AGCTGCATTTTTACAGAACAGAAATGCAACGCGAGAGCGCTATTTTACCA
ACAAAGAATCTATACTTCTTTTTTGTTCTACAAAAATGCATCCCGAGAGC
GCTATTTTTCTAACAAAGCATCTTAGATTACTTTTTTTCTCCTTTGTGCG
CTCTATAATGCAGTCTCTTGATAACTTTTTGCACTGTAGGTCCGTTAAGG
TTAGAAGAAGGCTACTTTGGTGTCTATTTTCTCTTCCATAAAAAAGCCT
GACTCCACTTCCCGCGTTTACTGATTACTAGCGAAGCTGCGGGTGCATTT
TTTCAAGATAAAGGCATCCCCGATTATATTCTATACCGATGTGGATTGCG
CATACTTTGTGAACAGAAAGTGATAGCGTTGATGATTCTTCATTGGTCAG
AAAATTATGAACGGTTTCTTCTATTTTGTCTCTATATACTACGTATAGGA
AATGTTTACATTTTCGTATTGTTTTCGATTCACTCTATGAATAGTTCTTA
CTACAATTTTTTTGTCTAAAGAGTAATACTAGAGATAAACATAAAAAATG
TAGAGGTCGAGTTTAGATGCAAGTTCAAGGAGCGAAAGGTGGATGGGTAG
GTTATATAGGGATATAGCACAGAGATATATAGCAAAGAGATACTTTTGAG
CAATGTTTGTGGAAGCGGTATTCGCAATATTTTAGTAGCTCGTTACAGTC
CGGTGCGTTTTTGGTTTTTTGAAAGTGCGTCTTCAGAGCGCTTTTGGTTT
TCAAAAGCGCTCTGAAGTTCCTATACTTTCTAGAGAATAGGAACTTCGGA
ATAGGAACTTCAAAGCGTTTCCGAAAACGAGCGCTTCCGAAAATGCAACG
CGAGCTGCGCACATACAGCTCACTGTTCACGTCGCACCTATATCTGCGTG -continued

```
TTGCCTGTATATATATACATGAGAAGAACGGCATAGTGCGTGTTTATG

CTTAAATGCGTACTTATATGCGTCTATTTATGTAGGATGAAAGGTAGTCT

AGTACCTCCTGTGATATTATCCCATTCCATGCGGGGTATCGTATGCTTCC

TTCAGCACTACCCTTTAGCTGTTCTATATGCTGCCACTCCTCAATTGGAT

TAGTCTCATCCTTCAATGCTATCATTTCCTTTGATATTGGATCAT
```

In plasmid pCLS16715, the sequence coding for the TALEN arm (SEQ ID NO: 50) comprises:
 a sequence coding for 15 adjacent units of TAL effector tandem repeat, and
 a sequence coding for an endonuclease.

The 15 adjacent units of TAL effector tandem repeat are a N- to C-ordered series of 15 adjacent units each consisting of 34 amino acids. The last C-terminal unit of 34 amino acids is followed by one (truncated) unit of 20 amino acids.

The ordered series of 15 adjacent units determines the recognition of a specific DNA target site (of 15 nucleotides, i.e., of SEQ ID NO: 4), whereas the (truncated) unit of 20 amino acids is not involved in the specific recognition of said DNA target site.

The sequence coding for said 15 adjacent units of 34 amino acids is at positions 481-2010 within the TALEN coding sequence of SEQ ID NO: 50, i.e., is:

```
[SEQ ID NO: 54]
TTGACCCCCCAGCAGGTGGTGGCCATCGCCAGCAATAATGGTGGCAAGCA

GGCGCTGGAGACGGTCCAGCGGCTGTTGCCGGTGCTGTGCCAGGCCCACG

GCTTGACCCCCCAGCAGGTGGTGGCCATCGCCAGCAATGGCGGTGGCAAG

CAGGCGCTGGAGACGGTCCAGCGGCTGTTGCCGGTGCTGTGCCAGGCCCA

CGGCTTGACCCCCCAGCAGGTGGTGGCCATCGCCAGCAATAATGGTGGCA

AGCAGGCGCTGGAGACGGTCCAGCGGCTGTTGCCGGTGCTGTGCCAGGCC

CACGGCTTGACCCCGGAGCAGGTGGTGGCCATCGCCAGCAATATTGGTGG

CAAGCAGGCGCTGGAGACGGTGCAGGCGCTGTTGCCGGTGCTGTGCCAGG

CCCACGGCTTGACCCCCCAGCAGGTGGTGGCCATCGCCAGCAATGGCGGT

GGCAAGCAGGCGCTGGAGACGGTCCAGCGGCTGTTGCCGGTGCTGTGCCA

GGCCCACGGCTTGACCCCGGAGCAGGTGGTGGCCATCGCCAGCCACGATG

GCGGCAAGCAGGCGCTGGAGACGGTCCAGCGGCTGTTGCCGGTGCTGTGC

CAGGCCCACGGCTTGACCCCGGAGCAGGTGGTGGCCATCGCCAGCCACGA

TGGCGGCAAGCAGGCGCTGGAGACGGTCCAGCGGCTGTTGCCGGTGCTGT

GCCAGGCCCACGGCTTGACCCCGGAGCAGGTGGTGGCCATCGCCAGCCAC

GATGGCGGCAAGCAGGCGCTGGAGACGGTCCAGCGGCTGTTGCCGGTGCT

GTGCCAGGCCCACGGCTTGACCCCGGAGCAGGTGGTGGCCATCGCCAGCC

ACGATGGCGGCAAGCAGGCGCTGGAGACGGTCCAGCGGCTGTTGCCGGTG

CTGTGCCAGGCCCACGGCTTGACCCCGGAGCAGGTGGTGGCCATCGCCAG

CCACGATGGCGGCAAGCAGGCGCTGGAGACGGTCCAGCGGCTGTTGCCGG

TGCTGTGCCAGGCCCACGGCTTGACCCCGGAGCAGGTGGTGGCCATCGCC

AGCCACGATGGCGGCAAGCAGGCGCTGGAGACGGTCCAGCGGCTGTTGCC

GGTGCTGTGCCAGGCCCACGGCTTGACCCCGGAGCAGGTGGTGGCCATCG

CCAGCAATATTGGTGGCAAGCAGGCGCTGGAGACGGTGCAGGCGCTGTTG

CCGGTGCTGTGCCAGGCCCACGGCTTGACCCCCCAGCAGGTGGTGGCCAT

CGCCAGCAATAATGGTGGCAAGCAGGCGCTGGAGACGGTCCAGCGGCTGT

TGCCGGTGCTGTGCCAGGCCCACGGCTTGACCCCGGAGCAGGTGGTGGCC

ATCGCCAGCCACGATGGCGGCAAGCAGGCGCTGGAGACGGTCCAGCGGCT

GTTGCCGGTGCTGTGCCAGGCCCACGGCTTGACCCCGGAGCAGGTGGTGG

CCATCGCCAGCAATATTGGTGGCAAGCAGGCGCTGGAGACGGTGCAGGCG

CTGTTGCCGGTGCTGTGCCAGGCCCACGGC.
```

The sequence of one of said 15 adjacent units of 34 amino acids (coding sequence comprised in SEQ ID NO: 54) is:

```
                                     [SEQ ID NO: 46]
    LTPQQVVAIASXXGGKQALETVQRLLPVLCQAHG,
    or
                                     [SEQ ID NO: 55]
    LTPEQVVAIASXXGGKQALETVQALLPVLCQAHG,
    or
                                     [SEQ ID NO: 25]
    LTPEQVVAIASXXGGKQALETVQRLLPVLCQAHG,
    or wherein XX is the RVD of the unit.
```

The N- to C-ordered series of RVDs formed by the RVDs respectively contained in the 15 adjacent units of TAL effector tandem repeat is:
 NN; NG; NN; NI; NG; HD; HD; HD; HD; HD; HD; NI; NN; HD; NI.

The N- to C-ordered series of RVDs determines the recognition of the DNA target site of SEQ ID NO: 4, i.e., GTGATCCCCCCAGCA (cf. Table 5 above; cf. FIG. 1B).

The sequence coding for said truncated unit of 20 amino acids is the sequence of SEQ ID NO: 47 (coding for the unit of SEQ ID NO: 48; same coding and amino acid sequences as in plasmid pCLS9996), and is at positions 2011-2070 within the TALEN coding sequence of SEQ ID NO: 50.

The sequence coding for the FokI monomer (same FokI monomer as in the plasmid pCLS9996) is the sequence of SEQ ID NO: 3 (coding for the FokI monomer of SEQ ID NO: 49), and is at positions 2212-2808 within the TALEN coding sequence of SEQ ID NO: 50.

Sequence Data for the DNA Target Sites:

```
5'-3' sequence of the DNA target site of
the left-hand TALE (cf. FIG. 1B) =
                                     [SEQ ID NO: 4]
GTGATCCCCCCAGCA Sequence complementary to the sequence of the
DNA target site of the left-hand TALE (5'-
                                     [SEQ ID NO: 5]
3') = TGCTGGGGGATCAC
```

Portion of the DNA target site of the left-hand TALE that is the sequence of the 5' end of the tandem repeat:

```
                                     [SEQ ID NO: 6]
                    CAGCA,
```

Portion of the DNA target site of the left-hand TALE that is the gene sequence that is immediately adjacent to the 5' end of the tandem repeat (outside of the tandem repeat sequence):

```
                                                    [SEQ ID NO: 7]
GTGATCCCCC

5'-3' sequence of the spacer (cf. FIG. 1B) =
                                                    [SEQ ID NO: 8]
GCAGCAGCAGCAGCAGCAGC Sequence of the spacer (5'-3') on the
complementary strand (5'-3') =
                                                    [SEQ ID NO: 9]
GCTGCTGCTGCTGCTGCTGC 5'-3' sequence of the DNA target site
of the right-hand TALE (cf. FIG. 1B) =
                                                    [SEQ ID NO: 10]
GCTGCTGCTGCTGCT Sequence complementary to the DNA target
site of the right-hand TALE (5'-3') =
                                                    [SEQ ID NO: 11]
AGCAGCAGCAGCAGC Sequence of the split left TALE DNA-binding
domain (5'-3') =
                                                    [SEQ ID NO: 12]
TCGCTG-

CAGGTCGGCCTCAGCCTGGCCGAAAGAAAGAAATGGTCTGTGATCCCCC-

CAGCAGCAGC

Sequence complementary to the split left TALE
DNA-binding domain (5'-3') =
                                                    [SEQ ID NO: 13]
GCTGCTGCTG-

GTCCAGCCGGAGTCGGACCGGCTTTCTTTCTTTACCAGACACTAGGGGG-

CAGCGA
```

Molecular analysis of survivors after TALEN induction. Please see FIGS. 2A-AD.

FIG. 2A: Survival after galactose induction. Cells were grown in YPLactate for 5 hours (one generation), then plated on SC-Leu plates supplemented with 200 μg/mL G418 sulfate, containing either 20 g/L glucose or galactose. Survival was determined as the ratio of CFU on galactose plates over CFU on glucose plates, after 3-5 days of growth at 30° C.

FIG. 2B: Molecular analysis of heterozygous diploids (SUP4-opa1/sup4-(CAG))[(CAG)$_{13}$=SEQ ID NO: 27]. Red and white colonies were picked, total genomic DNA was extracted, digested with Eco RV, loaded on a 1% agarose gel and run overnight at 1 V/cm. The gel was vacuum transferred to a HYBOND-XL® nylon membrane (AMERSHAM) and hybridized with a randomly-labeled probe specific of a unique region downstream of SUP4. After washing, the membrane was overnight exposed on a FUJIFILM FLA-9000.

FIG. 2C: DNA extracted from survivors was PCR amplified using primers su3/su9 and in vitro digested using restriction enzyme I-Sce I (I) or Pst I (P). For each clone, numbered 1 to 20, the two lanes show the result of restriction with one of the two enzymes. When both alleles are present, bands of slightly different sizes corresponding to uncut alleles are visible in both lanes (arrow labeled "Uncut"), along with restriction products of cut alleles (arrows labeled "Cut"). When only the SUP4-opa1 allele is present, no cut product is detected in the 'I' lane (clones 8 and 11 to 20). Note that these 20 survivors correspond to the same clones as in FIG. 2B.

Figure 2D:
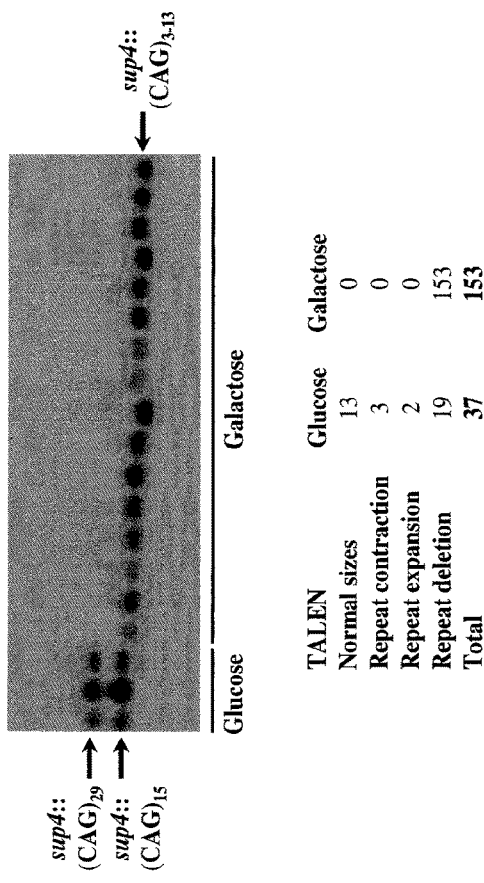

FIG. 2D: Molecular analysis of homozygous diploids (sup4-(CAG)/sup4-(CAG)). Same as FIG. 2B, except that total genomic DNA was digested with Ssp I.

[(CAG)$_{29}$=SEQ ID NO: 28; (CAG)$_{15}$=SEQ ID NO: 29; (CAG)$_{3}$=SEQ ID NO: 30]

Karyotypes and sequencing of TALEN-induced yeast colonies. Please see FIGS. 3A-3D. FIG. 3A: Sanger sequencing of survivors. PCR fragment amplified with su3/su9 (FIG. 2C) was sequenced using a primer (su7) located ca. 210 bp upstream of the repeat tract.

Upper and lower graphs: when only one allele was present, one unique sequence was read [upper graph, homozygous (CTG)$_9$/(CTG)$_9$ ((CTG)$_9$=SEQ ID NO: 14); the sequence reads:

```
                                        (SEQ ID NO: 15)]
        TAGCCGGGAATG(CTG)₉GGGGGATCACAGACCATTTCTTTCTT.
```

When two alleles of different lengths were present, the sequence was blurry and unreadable after the shortest of the two repeat tracts [lower graph, heterozygous (CTG)$_9$/(CTG)$_n$ ((CTG)$_9$=SEQ ID NO: 14); the sequence reads:

```
                                        (SEQ ID NO: 16)]
        TAGCCGGGAATG(CTG)₉GGGGGATCACATACTTTTTTTTCTTTCG.
```

The freeware 4PEAKS was used to visualize sequences.

Histogram at the bottom of FIG. 3B: length distribution of alleles in homozygous and heterozygous survivors to TALEN induction. The values read as shown in Table 1 below.

TABLE 1

| Final length of | Number | |
|---|---|---|
| repeat tract | Heterozygotes | Homozygotes |
| 3 | 0 | 4 |
| 4 | 0 | 4 |
| 5 | 1 | 4 |
| 6 | 1 | 4 |
| 7 | 10 | 4 |
| 8 | 9 | 16 |
| 9 | 4 | 6 |
| 10 | 3 | 4 |
| 11 | 2 | 0 |
| 12 | 1 | 0 |
| 13 | 5 | 0 |
| 20 | 1 | 0 |

Note that for heterozygous alleles only the length of the shortest repeat can be precisely known, hence the statistical difference observed between the two distributions is even more important than shown.

FIG. 3B: Two models proposing how heterozygous and homozygous repeats may be formed following TALEN induction.

FIG. 3C: Deep sequencing of yeast genomes from yeast colonies isolated on glucose or galactose plates. Each of the 15 yeast genomes was re-sequenced to 700× coverage, on the average (see Table 2 below). For each colony, the number of unique SNPs and insertions/deletions is indicated.

TABLE 2

Illumina sequencing data

| Origin | Library | Total reads | Initial read length (bp) | Read length after trimming (bp) | Median sequencing depth |
|---|---|---|---|---|---|
| Galactose | GAL1 | $298 \times 10^6$ | 110 | 82 | 1601 X |
|  | GAL2 | $119.6 \times 10^6$ | 110 | 82 | 677 X |
|  | GAL3 | $134.4 \times 10^6$ | 110 | 82 | 780 X |
|  | GAL4 | $117.8 \times 10^6$ | 110 | 82 | 675 X |
|  | GAL5 | $262.2 \times 10^6$ | 110 | 82 | 765 X |
|  | GAL6 | $167.6 \times 10^6$ | 110 | 82 | 975 X |
|  | GAL7 | $155.4 \times 10^6$ | 110 | 82 | 1779 x |
| Glucose | GLU1 | $41.2 \times 10^6$ | 110 | 83 | 457 X |
|  | GLU2 | $41.2 \times 10^6$ | 110 | 83 | 457 x |
|  | GLU3 | $70 \times 10^6$ | 110 | 83 | 394 X |
|  | GLU4 | $118 \times 10^6$ | 110 | 83 | 648 X |
|  | GLU5 | $54 \times 10^6$ | 110 | 83 | 303 X |
|  | GLU6 | $28 \times 10^6$ | 110 | 83 | 156 X |
|  | GLU7 | $44 \times 10^6$ | 110 | 83 | 249 X |
|  | GLU8 | $100 \times 10^6$ | 110 | 83 | 588 X |

Each library corresponds to one individual colony, collected on glucose or galactose plates (Origin), grown in non-selective rich medium, whose DNA was extracted and sonicated to an average size of 500 bp (BIORUPTOR, maximum power (H), 30" ON/30" OFF cycles, 9 cycles). DNA ends were subsequently repaired with T4 DNA polymerase (15 units, NEBIOLABS) and KLENOW DNA polymerase (5 units, NEBIOLABS) and phosphorylated with T4 DNA kinase (50 units, NEBIOLABS). Repaired DNA was purified on two MINELUTE columns (QIAGEN) and eluted in 16 μl (32 μl final for each library). Addition of a 3' dATP was performed with KLENOW DNA polymerase (exo-) (15 units, NEBIOLABS) and home-made adapters containing a 4-bp unique tag used for multiplexing, were ligated with 2 μl T4 DNA ligase (NEBIOLABS, high concentration, $2 \times 10^6$ units/ml). DNA was size fractionated on a PIPPIN PREP (SAGE SCIENCE) and the fraction containing 400-600 bp DNA fragments was recovered in LOBIND microtubes (EPPENDORF). DNA was PCR amplified with ILLUMINA primers PE1.0 and PE2.0 and PHUSION DNA polymerase (1 unit, THERMO SCIENTIFIC). Depending on PCR efficiency, 9, 12 or 15 PCR cycles were performed on each library. Twenty-four PCR reactions were pooled, for each library, and purified on QIAGEN purification columns (two columns were used for 24 PCR reactions). Elution was performed in 60 μl (twice 30 μl) and DNA was quantified on a spectrophotometer and on an agarose gel.

Two multiplexed libraries were loaded on each lane of a HISEQ 2000 (ILLUMINA), and 110 bp paired-end reads were generated. Reads quality was evaluated by FASTQC v.0.10.1 [http://www.bioinformatics.babraham.ac.uk/projects/fastqc/] and trimmed off using the paired-end mode of TRIMMOMATIC v0.30 [http://www.usadellab.org/cms/index.php?page=trimmomatic].

TRIMMED reads were mapped along S288C chromosomes reference sequence (GENBANK NC_001133 to NC_001148, PLN 6 Dec. 2008), plus the two SUP4 alleles (SUP4-opa1 and sup4-(CAG)) using the paired-end mapping mode of BWA v0.6.2 (Li and Durbin 2009) with default parameters. The output SAM files were converted and sorted to BAM files using SAMTOOLS v0.1.18 (Li et al. 2009).

The command IndelRealigner from GATK v2.2 (DePristo et al. 2011) was used to realigne the reads. Duplicated reads were removed using the option "MarkDuplicates" implemented in Picard v1.81 [http://picard.sourceforge.net/].

Reads uniquely mapped to the reference sequence with a minimum mapping quality of 30 (PHRED-scaled) were kept. MPILEUP files were generated by SAMTOOLS without BAQ adjustments. SNPs and INDELs were called by the options "mpileup2snp" and "mpileup2indel" of Varscan2 v2.3.5 (Koboldt et al. 2012) with a minimum depth of 5 reads and a threshold of 0.3 for minimum variant allele frequency (strains are diploids). Mismatches were kept when they represented at least 20% of the reads supporting the variant on each strand. They were manually examined and compared between all sequenced libraries for interpretation.

FIG. 3D: Pulse-field gel electrophoresis of red and white colonies after galactose induction. Karyotypes are identical among all clones and do not show any large chromosomal rearrangement, neither on chromosome X (bearing SUP4) nor on any other chromosome.

FIG. 4:

Left: strains GFY6161-3C (MATα leu2Δ1 his3Δ200 lys2Δ202 ade2-opa1 sup4::$(CAG)_{30}$) and GFY6162-3D (MATα ura3Δ851 leu2Δ1 his3Δ200 trp1Δ65 ade2-opa1 sup4::$(CAG)_{100}$) were respectively transformed with pCLS9996 (KANMX marker) or pCLS16715 (LEU2 marker). Seven transformants were analyzed by Southern blot, for each strain, to estimate repeat length variability after transformation. Transformant 4 in strain GFY6162-3C shows extensive contractions of the repeat tract, but all other transformants exhibit stable trinucleotide repeats after transformation. Right: Transformants GFY6162-3C/1 and GFY6162-3D/2 were crossed, and diploids were selected on glucose SC-Leu plates supplemented with G418 sulfate (200 μg/ml). Twelve independent diploids were analyzed by Southern blot, as previously. None of the diploids contained the repeat band around 100 triplets, showing that it was contracted during or right after the cross, even though cells were crossed on glucose medium. In this particular cross, diploid #5 was selected for further induction experiments. [$(CTG)_{122}$=SEQ ID NO: 31; $(CTG)_{72}$=SEQ ID NO: 32; $(CTG)_{32}$=SEQ ID NO: 33; $(CTG)_{2}$=SEQ ID NO: 34]

Example 2

Myotonic dystrophy (DM) is caused by a CTG repeat expansion in the 3'UTR of the DM protein kinase (DMPK) gene [$(CTG)_n \cdot (CAG)_n$ repeat]. The size of the CTG repeat, which increases from generation to generation with sometimes very large expansions, is generally correlated with clinical severity and age at onset, providing a molecular basis for the anticipation phenomenon observed in DM1 families.

Transgenic mice carrying the human DMPK gene with a normal CTG repeat (i.e., 5-37 repeat units) or with an expanded CTG repeat (e.g., 200-3,000 CTG repeat units) were generated and bred as described in Gantelet et al. 2007, Seznec et al. 2001, Gomes-Pereira et al. 2007, Panaite et al. 2011, Panaite et al. 2013.

Transgenic mice carrying about 20 CTG repeat units (DM20 mice) are control mice, which do not show the DM1 phenotype.

Transgenic mice carrying 200-3,000 CTG repeat units develop the DM1 phenotype, ranging from mild DM1 phenotype (e.g., mice, which carry about 500 CTG repeat units) to severe DM1 phenotype (e.g., mice, which carry more than 1,300 CTG repeat units).

Fibroblast primary cells have been isolated from DM20 mice and mice carrying different lengths of expanded repeat (e.g., about 500 CTG repeat units; more than 1,300 CTG repeat units), and have been cultured on a culture medium.

Human cells have been collected from healthy donors having a normal DMPK CTG repeat length, as well as from DM1 patients at different stages of the disease.

Plasmids coding for DNA-binding polypeptides of the application, such as the TALEN described in example 1 above, have been transfected into the mouse fibroblast primary cells or into the human cells.

Plasmids coding for DNA-binding polypeptides of the application, such as the TALEN described in example 1 above, have been administered to the mice, e.g., by intra-veinous injection.

The effect of the TALEN on the repeat length has been determined by Southern blot analysis and/or PCR, e.g., as described in Jansen et al. 1994.

BIBLIOGRAPHIC REFERENCES

Bedell, V. M. et al. 2012. In vivo genome editing using a high-efficiency TALEN system. Nature 491, 114-118, doi:nature11537 [pii] 10.1038/nature11537.

Beurdeley, M. et al. 2013. Compact designer TALENs for efficient genome engineering. Nat. Commun. 4, 1762, doi:ncomms2782 [pii] 10.1038/ncomms2782.

Boch, J. et al. 2009. Breaking the code of DNA binding specificity of TAL-type III effectors. Science 326, 1509-1512, doi:1178811 [pii] 10.1126/science.1178811.

Bogdanove and Voytas. 2011. TAL effectors: Customizable proteins for DNA targeting. Science 33, 1843-1846.

Cade, L. et al. 2012. Highly efficient generation of heritable zebrafish gene mutations using homo- and heterodimeric TALENs. Nucleic Acids Res. 40, 8001-8010, doi:gks518 [pii] 10.1093/nar/gks518.

Cermak, T. et al. 2011. Efficient design and assembly of custom TALEN and other TAL effector-based constructs for DNA targeting. Nucleic Acids Res. 39, e82, doi: gkr218 [pii] 10.1093/nar/gkr218.

Chen, S. et al. 2013. A large-scale in vivo analysis reveals that TALENs are significantly more mutagenic than ZFNs generated using context-dependent assembly. Nucleic Acids Res. 41, 2769-2778, doi:gks1356 [pii] 10.1093/nar/gks1356.

Christian, M. et al. 2010. Targeting DNA double-strand breaks with TAL effector nucleases. *Genetics* 186, 757-761, doi:genetics.110.120717 [pii] 10.1534/genetics.110.120717.

DePristo, M. A. et al. 2011. A framework for variation discovery and genotyping using next-generation DNA sequencing data. Nat. Genet. 43, 491-498, doi:ng.806 [pii] 10.1038/ng.806.

Durfec et al. 2008. The complete genome sequence of *Escherichia coli* DH10B: insights into the biology of a laboratory workhorse. J. Bacteriol. 190(7): 2597-2606.

Gantelet et al. 2007. The expansion of 300 CTG repeats in myotonic dystrophy transgenic mice does not induce sensory or motor neuropathy. Acta Neuropathol. 114: 175-185.

Giniger, E., Varnum, S. M. & Ptashne, M. 1985. Specific DNA binding of GAL4, a positive regulatory protein of yeast. *Cell* 40, 767-774, doi:0092-8674(85)90336-8 [pii].

Gomes-Pereira et al. 2007. CTG trinucleotide repeat "big jumps": large expansions, small mice. PLoS Genet. 3: e52.

Jansen et al. 1994. Gonosomal mosaicism in myotonic dystrophy patients: involvement of mitotic events in (CTG)n repeat variation and selection against extreme expansion in sperm. Am. J. Hum. Genet. 54: 575-585.

Koboldt, D. C. et al. 2012. VarScan 2: somatic mutation and copy number alteration discovery in cancer by exome sequencing. *Genome Res.* 22, 568-576, doi:gr.129684.111 [pii] 10.1101/gr.129684.111.

Li, H. and Durbin, R. 2009. Fast and accurate short read alignment with Burrows-Wheeler transform. Bioinformatics 25: 1754-1760, doi:btp324 [pii] 10.1093/bioinformatics/btp324.

Li., H. et al. 2009. The sequence alignment/map format and SAMtools. Bioinformatics 25: 2078-2079, doi:btp352 [pii] 10.1093/bioinformatics/btp352.

Li, T. et al. 2011. TAL nucleases (TALNs): hybrid proteins composed of TAL effectors and FokI DNA-cleavage domain. Nucleic Acids Res. 39, 359-372, doi:gkq704 [pii] 10.1093/nar/gkq704.

Lynch, M. et al. 2008. A genome-wide view of the spectrum of spontaneous mutations in yeast. Proc. Natl. Acad. Sci. U.S.A. 105, 9272-9277, doi:0803466105 [pii] 10.1073/pnas.0803466105.

Moscou, M. J. & Bogdanove, A. J. 2010. A simple cipher governs DNA recognition by TAL effectors. Science 326, 1501, doi:1178817 [pii] 10.1126/science.1178817 (2009).

McKusick, V. A. 1998. Mendelian Inheritance in Man; A Catalog of Human Genes and Genetic Disorders. Baltimore, Md., U.S.A., Johns Hopkins University Press, ISBN 0-8018-5742-2.

McMurray. Mechanisms of trinucleotide repeat instability during human development. Nat. Rev. Genet. 11(11): 786-799.

O'Hoy, K. L. et al. 1993. Reduction in size of the myotonic dystrophy trinucleotide repeat mutation during transmission. Science 259, 809-812.

Panaite et al. 2011. Peripheral neuropathy is linked to a severe form of myotonic dystrophy in transgenic mice. J. Neuropathol. Exp. Neurol. 70: 678-685.

Panaite et al. 2013. Functional and histopathological identification of the respiratory failure in a DMSXL transgenic mouse model of myotonic dystrophy. Dis. Model Mech. 6(3): 622-631.

Philippe S. et al. 2006. Lentiviral vectors with a defective integrase allow efficient and sustained transgene expression in vitro and in vivo. PNAS 103(47): 17684-17689.

Qiu, Z. et al. 2013. High-efficiency and heritable gene targeting in mouse by transcription activator-like effector nucleases. Nucleic Acids Res., doi:gkt258 [pii] 10.1093/nar/gkt258. Remington: The Science and Practice of Pharmacy", $20^{th}$ edition, Mack Publishing Co.; and "Pharmaceutical Dosage Forms and Drug Delivery Systems", Ansel, Popovich and Allen Jr., Lippincott Williams and Wilkins.

Richard, G.-F., Dujon, B. & Haber, J. E. 1999. Double-strand break repair can lead to high frequencies of deletions within short CAG/CTG trinucleotide repeats. Mol. Gen. Genet. 261, 871-882.

Richard, G.-F., Goellner, G. M., McMurray, C. T. & Haber, J. E. 2000. Recombination-induced CAG trinucleotide repeat expansions in yeast involve the MRE11/RAD50/XRS2 complex. EMBO J. 19, 2381-2390.

Richard, G.-F., Cyncynatus, C. & Dujon, B. 2003. Contractions and expansions of CAG/CTG trinucleotide repeats occur during ectopic gene conversion in yeast, by a MUS81-independent mechanism. J. Mol. Biol. 326, 769-782 (2003).

Seznec et al. 2001. Mice transgenic for the human myotonic dystrophy region with expanded CTG repeats display muscular and brain abnormalities. Hum. Mol. Genet. 10: 2717-2726.

WO 94/18313 and its national counterparts including its US counterpart(s) (including the US continuation and divisional applications).

WO 95/09233 and its national counterparts including its US counterpart(s) (including the US continuation and divisional applications).

WO 99/55892 and its national counterparts including its US counterpart(s) (including the US continuation and divisional applications).

WO 2006/010834 and its national counterparts including its US counterpart(s) (including the US continuation and divisional applications).

WO 2009/019612 and its national counterparts including its US counterpart(s) (including the US continuation and divisional applications).

WO 2011/072246 and its national counterparts, including its US counterpart(s) (including the US continuation and divisional applications).

WO 2010/079430 and its national counterparts, including its US counterpart(s) (including the US continuation and divisional applications).

WO 2012/015938 and its national counterparts, including its US national counterpart(s) (including the US continuation and divisional applications).

WO 2013/068430 and its national counterparts including its US counterpart(s) (including the US continuation and divisional applications).

SEQUENCE LISTING

```
<160> NUMBER OF SEQ ID NOS: 56

<210> SEQ ID NO 1
<211> LENGTH: 8810
<212> TYPE: DNA
<213> ORGANISM: Artificial
<220> FEATURE:
<223> OTHER INFORMATION: plasmid pCLS9996

<400> SEQUENCE: 1
gcgcacattt ccccgaaaag tgccacctga cgtccgatca aaaatcatcg cttcgctgat      60
taattacccc agaaataagg ctaaaaaact aatcgcatta tcatcctatg gttgttaatt     120
tgattcgttc atttgaaggt ttgtggggcc aggttactgc caatttttcc tcttcataac     180
cataaaagct agtattgtag aatctttatt gttcggagca gtgcggcgcg aggcacatct     240
gcgtttcagg aacgcgaccg gtgaagacga ggacgcacgg aggagagtct tccttcggag     300
ggctgtcacc cgctcggcgg cttctaatcc gtacttcaat atagcaatga gcagttaagc     360
gtattactga aagttccaaa gagaaggttt ttttaggcta atcgacctcg agcagatccg     420
ccaggcgtgt atatagcgtg gatggccagg caactttagt gctgacacat acaggcatat     480
atatatgtgt gcgacgacac atgatcatat ggcatgcatg tgctctgtat gtatataaaa     540
ctcttgtttt cttcttttct ctaaatattc tttccttata cattaggtcc tttgtagcat     600
aaattactat acttctatag acacgcaaac acaaatacac agcggccttg ccaccatggg     660
cgatcctaaa aagaaacgta aggtcatcga taaggagacc gccgctgcca agttcgagag     720
acagcacatg gacagcatcg atatcgccga tctacgcacg ctcggctaca gccagcagca     780
acaggagaag atcaaaccga aggttcgttc gacagtggcg cagcaccacg aggcactggt     840
cggccacggg tttacacacg cgcacatcgt tgcgttaagc caacacccgg cagcgttagg     900
gaccgtcgct gtcaagtatc aggacatgat cgcagcgttg ccagaggcga cacacgaagc     960
gatcgttggc gtcggcaaac agtggtccgg cgcacgcgct ctggaggcct tgctcacggt    1020
ggcgggagag ttgagaggtc caccgttaca gttggacaca ggccaacttc tcaagattgc    1080
aaaacgtggc ggcgtgaccg cagtggaggc agtgcatgca tggcgcaatg cactgacggg    1140
tgccccgctc aacttgaccc cccagcaggt ggtggccatc gccagcaata atggtggcaa    1200
gcaggcgctg gagacggtcc agcggctgtt gccggtgctg tgccaggccc acggcttgac    1260
cccggagcag gtggtggcca tcgccagcca cgatggcggc aagcaggcgc tggagacggt    1320
ccagcggctg ttgccggtgc tgtgccaggc ccacggcttg accccccagc aggtggtggc    1380
```

-continued

```
catcgccagc aatggcggtg gcaagcaggc gctggagacg gtccagcggc tgttgccggt    1440
gctgtgccag gcccacggct tgaccccca gcaggtggtg gccatcgcca gcaataatgg     1500
tggcaagcag gcgctggaga cggtccagcg gctgttgccg gtgctgtgcc aggcccacgg    1560
cttgaccccg gagcaggtgg tggccatcgc cagccacgat ggcggcaagc aggcgctgga    1620
gacggtccag cggctgttgc cggtgctgtg ccaggcccac ggcttgaccc ccagcaggt    1680
ggtggccatc gccagcaatg gcggtggcaa gcaggcgctg gagacggtcc agcggctgtt   1740
gccggtgctg tgccaggccc acggcttgac ccccagcag gtggtggcca tcgccagcaa    1800
taatggtggc aagcaggcgc tggagacggt ccagcggctg ttgccggtgc tgtgccaggc   1860
ccacggcttg accccggagc aggtggtggc catcgccagc cacgatggcg gcaagcaggc   1920
gctggagacg tccagcggc tgttgccggt gctgtgccag gcccacgct tgaccccca     1980
gcaggtggtg gccatcgcca gcaatggcgg tggcaagcag gcgctggaga cggtccagcg   2040
gctgttgccg gtgctgtgcc aggcccacgg cttgaccccc cagcaggtgg tggccatcgc    2100
cagcaataat ggtggcaagc aggcgctgga cggtccagc cggctgttgc cggtgctgtg    2160
ccaggcccac ggcttgaccc cggagcaggt ggtggccatc gccagccacg atggcggcaa   2220
gcaggcgctg gagacggtcc agcggctgtt gccggtgctg tgccaggccc acggcttgac   2280
ccccagcag gtggtggcca tcgccagcaa tggcggtggc aagcaggcgc tggagacggt   2340
ccagcggctg ttgccggtgc tgtgccaggc ccacggcttg accccccagc aggtggtggc   2400
catcgccagc aataatggtg gcaagcaggc gctggagacg gtccagcggc tgttgccggt    2460
gctgtgccag gcccacggct tgaccccgga caggtggtg gccatcgcca gccacgatgg   2520
cggcaagcag gcgctggaga cggtccagcg gctgttgccg gtgctgtgcc aggcccacgg   2580
cttgaccccc cagcaggtgg tggccatcgc cagcaatggc ggtggcaagc aggcgctgga   2640
gacggtccag cggctgttgc cggtgctgtg ccaggcccac ggcttgaccc ctcagcaggt   2700
ggtggccatc gccagcaatg gcggcggcag gccggcgctg gagagcattg ttgcccagtt    2760
atctcgccct gatccggcgt tggccgcgtt gaccaacgac cacctcgtcg ccttggcctg    2820
cctcggcggg cgtcctgcgc tggatgcagt gaaaaaggga ttgggggatc ctatcagccg    2880
ttcccagctg gtgaagtccg agctggagga aagaaatcc gagttgaggc acaagctgaa    2940
gtacgtgccc cacgagtaca tcgagctgat cgagatcgcc cggaacagca cccaggaccg    3000
tatcctggag atgaaggtga tggagttctt catgaaggtg tacggctaca ggggcaagca    3060
cctgggcggc tccaggaagc ccgacggcgc catctctacacc gtgggctccc ccatcgacta   3120
cggcgtgatc gtggacacca aggcctactc cggcggctac aacctgcccc acggccaggc   3180
cgacgaaatg cagaggtacg tggaggagaa ccagaccagg aacaagcaca tcaaccccaa   3240
cgagtggtgg aaggtgtacc cctccagcgt gaccgagttc aagttcctgt tcgtgtccgg   3300
ccacttcaag ggcaactaca aggcccagct gaccaggctg aaccacatca ccaactgcaa   3360
cggcgccgtg ctgtccgtgg aggagctcct gatcggcggc gagatgatca aggccggcac   3420
cctgacctg gaggaggtga ggaggaagtt caacaacggc gagatcaact tcgcggccga   3480
ctgataactc gagcgatcct ctagacgagc tcctcgagcc tgcagcagct gaagctttgg   3540
acttcttcgc cagaggtttg gtcaagtctc caatcaaggt tgtcggcttg tctaccttgc   3600
cagaaattta cgaaagatg gaaagggtc aaatcgttgg tagatacgtt gttgacactt    3660
ctaaataagc gaatttctta tgattttatga tttttattat taataagtt ataaaaaaaa    3720
taagtgtata caaattttaa agtgactctt aggttttaaa acgaaaattc ttattcttga    3780
```

```
gtaactctttc cctgtaggtc aggttgcttt ctcaggtata gcatgaggtc gctcttattg    3840
accacacctc taccggcatg caagcttggc gtaatcatgg tcatagctgt ttcctgtgtg    3900
aaattgttat ccgctcacaa ttccacacaa catacgagcc ggaagcataa agtgtaaagc    3960
ctggggtgcc taatgagtga gctaactcac attaattgcg ttgcgctcac tgcccgcttt    4020
ccagtcggga aacctgtcgt gccagcagat ctgtttagct tgcctcgtcc ccgccgggtc    4080
acccggccag cgacatggag gcccagaata ccctccttga cagtcttgac gtgcgcagct    4140
caggggcatg atgtgactgt cgcccgtaca tttagcccat acatccccat gtataatcat    4200
ttgcatccat acattttgat ggccgcacgg cgcgaagcaa aaattacggc tcctcgctgc    4260
agacctgcga gcagggaaac gctcccctca cagacgcgtt gaattgtccc cacgccgcgc    4320
ccctgtagag aaatataaaa ggttaggatt tgccactgag gttcttcttt catatacttc    4380 ctttttaaaat cttgctagga tacagttctc acatcacatc cgaacataaa caaccatgca    4440
tgggtaagga aagactcac gtttcgaggc cgcgattaaa ttccaacatg gatgctgatt    4500
tatatgggta taaatgggct cgcgataatg tcggcaatc aggtgcgaca atctatcgat    4560
tgtatgggaa gcccgatgcg ccagagttgt ttctgaaaca tggcaaaggt agcgttgcca    4620
atgatgttac agatgagatg gtcagactaa actggctgac ggaatttatg cctcttccga    4680
ccatcaagca ttttatccgt actcctgatg atgcatggtt actcaccact gcgatccccg    4740
gcaaaacagc attccaggta ttagaagaat atcctgattc aggtgaaaat attgttgatg    4800
cgctggcagt gttcctgcgc cggttgcatt cgattcctgt ttgtaattgt ccttttaaca    4860
gcgatcgcgt atttcgcctc gctcaggcgc aatcacgaat gaataacggt ttggttgatg    4920
cgagtgattt tgatgacgag cgtaatggct ggcctgttga acaagtctgg aaagaaatgc    4980
ataagctttt gccattctca ccggattcag tcgtcactca tggtgatttc tcacttgata    5040 accttattttt tgacgagggg aaattaatag gttgtattga tgttggacga gtcggaatcg    5100
cagaccgata ccaggatctt gccatcctat ggaactgcct cggtgagttt tctccttcat    5160
tacagaaacg cttttttcaa aaatatggta ttgataatcc tgatatgaat aaattgcagt    5220
ttcatttgat gctcgatgag ttttttctaat cagtactgac aataaaaaga ttcttgtttt    5280
caagaacttg tcatttgtat agtttttta tattgtagtt gttctatttt aatcaaatgt    5340
tagcgtgatt tatatttttt ttcgcctcga catcatctgc ccagatgcga agttaagtgc    5400
gcagaaagta atatcatgcg tcaatcgtat gtgaatgctg gtcgctatac tgctgtcgat    5460
tcgatactaa cgccgccatc cagtgtcgaa aacgagctcg aattcatcga tgatatcaga    5520
tccactagtg gcctatgcga ccgcggatct gccggtctcc ctatagtgag tcgtattaat    5580
ttcgataagc caggttaacc tgcattaatg aatcggccaa cgcgcgggga gaggcggttt    5640
gcgtattggg cgctcttccg cttcctcgct cactgactcg ctgcgctcgg tcgttcggct    5700
gcggcgagcg gtatcagcat cgatgaattc cacgactat agactatact agtatactcc    5760
gtctactgta cgatacactt ccgctcaggt ccttgtcctt taacgaggcc ttaccactct    5820
tttgttactc tattgatcca gctcagcaaa ggcagtgtga tctaagattc tatcttcgcg    5880
atgtagtaaa actagctaga ccgagaaaga gactagaaat gcaaaaggca cttctacaat    5940
ggctgccatc attattatcc gatgtgacgc tgcagcttct caatgatatt cgaatacgct    6000
ttgaggagat acagcctaat atccgacaaa ctgttttaca gatttacgat cgtacttgtt    6060
acccatcatt gaattttgaa catccgaacc tgggagtttt ccctgaaaca gatagtatat    6120
```

```
ttgaacctgt ataataatat atagtctagc gctttacgga agacaatgta tgtatttcgg    6180
ttcctggaga aactattgca tctattgcat aggtaatctt gcacgtcgca tccccggttc    6240
attttctgcg tttccatctt gcacttcaat agcatatctt tgttaacgaa gcatctgtgc    6300
ttcattttgt agaacaaaaa tgcaacgcga gagcgctaat ttttcaaaca agaatctga     6360 gctgcatttt tacagaacag aaatgcaacg cgaaagcgct attttaccaa cgaagaatct    6420
gtgcttcatt tttgtaaaac aaaaatgcaa cgcgagagcg ctaatttttc aaacaaagaa    6480
tctgagctgc atttttacag aacagaaatg caacgcgaga gcgctatttt accaacaaag    6540
aatctatact tctttttgt tctacaaaaa tgcatcccga gagcgctatt tttctaacaa     6600
agcatcttag attactttt ttctcctttg tgcgctctat aatgcagtct cttgataact     6660
ttttgcactg taggtccgtt aaggttagaa gaaggctact tggtgtcta tttctcttc     6720 cataaaaaaa gcctgactcc acttcccgcg tttactgatt actagcgaag ctgcgggtgc    6780
attttttcaa gataaaggca tccccgatta tattctatac cgatgtggat tgcgcatact    6840
ttgtgaacag aaagtgatag cgttgatgat tcttcattgg tcagaaaatt atgaacggtt    6900
tcttctattt tgtctctata tactacgtat aggaaatgtt tacattttcg tattgttttc    6960
gattcactct atgaatagtt cttactacaa ttttttttgtc taaagagtaa tactagagat    7020
aaacataaaa aatgtagagg tcgagtttag atgcaagttc aaggagcgaa aggtggatgg    7080
gtaggttata tagggatata gcacagagat atatagcaaa gagatacttt tgagcaatgt    7140
ttgtggaagc ggtattcgca atatttagt agctcgttac agtccggtgc gttttggtt     7200 ttttgaaagt gcgtcttcag agcgcttttg gttttcaaaa gcgctctgaa gttcctatac    7260
tttctagaga ataggaactt cggaatagga acttcaaagc gtttccgaaa acgagcgctt    7320
ccgaaaatgc aacgcgagct gcgcacatac agctcactgt tcacgtcgca cctatatctg    7380
cgtgttgcct gtatatatat atacatgaga agaacggcat agtgcgtgtt tatgcttaaa    7440
tgcgtactta tatgcgtcta tttatgtagg atgaaaggta gtctagtacc tcctgtgata    7500
ttatcccatt ccatgcgggg tatcgtatgc ttccttcagc actacccttt agctgttcta    7560
tatgctgcca ctcctcaatt ggattagtct catccttcaa tgctatcatt tcctttgata    7620
ttggatcata tgcatagtac cgagaaacta gtgcgaagta gtgatcaggt attgctgtta    7680
tctgatgagt atacgttgtc ctggccacgg cagaagcacg cttatcgctc caatttccca    7740
caacattagt caactccgtt aggcccttca ttgaaagaaa tgaggtcatc aaatgtcttc    7800
caatgtgaga ttttgggcca tttttttatag caaagattga ataaggcgca ttttttcttca    7860 aagctttatt gtacgatctg actaagttat cttttaataa ttggtattcc tgtttattgc    7920
ttgaagaatt gccggtccta tttactcgtt ttaggactgg ttcagaattc atcgatgctc    7980
actcaaaggt cggtaatacg gttatccaca gaatcagggg ataacgcagg aaagaacatg    8040
tgagcaaaag gccagcaaaa ggccaggaac cgtaaaaagg ccgcgttgct ggcgtttttc    8100
cataggctcc gcccccctga cgagcatcac aaaaatcgac gctcaagtca gaggtggcga    8160
aacccgacag gactataaag ataccaggcg tttccccctg gaagctccct cgtgcgctct    8220
cctgttccga ccctgccgct taccggatac ctgtccgcct ttctcccttc gggaagcgtg    8280
gcgctttctc atagctcacg ctgtaggtat ctcagttcgg tgtaggtcgt tcgctccaag    8340
ctgggctgtg tgcacgaacc ccccgttcag cccgaccgct gcgccttatc cggtaactat    8400
cgtcttgagt ccaacccggt aagacacgac ttatcgccac tggcagcagc cactggtaac    8460
aggattagca gagcgaggta tgtaggcggt gctacagagt tcttgaagtg gtggcctaac    8520
```

```
tacggctaca ctagaaggac agtatttggt atctgcgctc tgctgaagcc agttaccttc    8580
ggaaaaagag ttggtagctc ttgatccggc aaacaaacca ccgctggtag cggtggtttt    8640
tttgtttgca agcagcagat tacgcgcaga aaaaaggat ctcaagaaga tcctttgatc     8700
ttttctacgg ggtctgacgc tcagtggaac gaaaactcac gttaagggat tttggtcatg    8760
agcggataca tatttgaatg tatttagaaa aataaacaaa tagggggttcc              8810

<210> SEQ ID NO 2
<211> LENGTH: 11109
<212> TYPE: DNA
<213> ORGANISM: Artificial
<220> FEATURE:
<223> OTHER INFORMATION: plasmid pCLS16715

<400> SEQUENCE: 2
gggttccgcg cacatttccc cgaaaagtgc cacctgacgt ccgatcaaaa atcatcgctt      60
cgctgattaa ttaccccaga ataaggcta aaaaactaat cgcattatca tcctatggtt     120
gttaatttga ttcgttcatt tgaaggtttg tggggccagg ttactgccaa ttttcctct      180 tcataaccat aaaagctagt attgtagaat ctttattgtt cggagcagtg cggcgcgagg    240
cacatctgcg tttcaggaac gcgaccggtg aagacgagga cgcacggagg agagtcttcc    300
ttcggagggc tgtcacccgc tcggcggctt ctaatccgta cttcaatata gcaatgagca    360
gttaagcgta ttactgaaag ttccaaagag aaggtttttt taggctaatc gacctcgagc    420
agatccgcca ggcgtgtata tagcgtggat ggccaggcaa cttagtgct gacacataca     480 ggcatatata tatgtgtgcg acgacacatg atcatatggc atgcatgtgc tctgtatgta    540
tataaaactc ttgttttctt cttttctcta aatattcttt ccttatacat taggtccttt    600
gtagcataaa ttactatact tctatagaca cgcaaacaca aatacacagc ggccttgcca    660
ccatgggcga tcctaaaaag aaacgtaagg tcatcgatta cccatacgat gttccagatt    720
acgctatcga tatcgccgat ctacgcacgc tcggctacag ccagcagcaa caggagaaga    780
tcaaaccgaa ggttcgttcg acagtggcgc agcaccacga ggcactggtc ggccacgggt    840
ttacacacgc gcacatcgtt gcgttaagcc aacacccggc agcgttaggg accgtcgctg    900
tcaagtatca ggacatgatc gcagcgttgc cagaggcgac acacgaagcg atcgttggcg    960
tcggcaaaca gtggtccggc gcacgcgctc tggaggcctt gctcacggtg gcgggagagt   1020
tgagaggtcc accgttacag ttggacacag gccaacttct caagattgca aaacgtggcg   1080
gcgtgaccgc agtggaggca gtgcatgcat ggcgcaatgc actgacgggt gccccgctca   1140
acttgacccc ccagcaggtg gtggccatcg ccagcaataa tggtggcaag caggcgctgg   1200
agacggtcca gcgctgttg ccggtgctgt gccaggccca cggcttgacc cccagcagg    1260 tggtggccat cgccagcaat ggcggtggca agcaggcgct ggagacggtc cagcggctgt   1320
tgccggtgct gtgccaggcc cacgcttga ccccccagca ggtggtggcc atcgccagca    1380
ataatggtgg caagcaggcg ctggagacgg tccagcggct gttgccggtg ctgtgccagg   1440
cccacggctt gaccccggag caggtggtgg ccatcgccag caatattggt ggcaagcagg   1500
cgctggagac ggtgcaggcg ctgttgccgg tgctgtgcca gcccacggc ttgaccccc     1560 agcaggtggt ggccatcgcc agcaatggcg gtggcaagca ggcgctggag acggtccagc   1620
ggctgttgcc ggtgctgtgc caggcccacg gcttgacccc ggagcaggtg gtggccatcg   1680
ccagccacga tggcggcaag caggcgctgg agacggtcca gcggctgttg ccggtgctgt   1740
```

```
gccaggccca cggcttgacc ccggagcagg tggtggccat cgccagccac gatggcggca    1800
agcaggcgct ggagacggtc cagcggctgt tgccggtgct gtgccaggcc cacggcttga    1860
ccccggagca ggtggtggcc atcgccagcc acgatggcgg caagcaggcg ctggagacgg    1920
tccagcggct gttgccggtg ctgtgccagg cccacggctt gaccccggag caggtggtgg    1980
ccatcgccag ccacgatggc ggcaagcagg cgctggagac ggtccagcgg ctgttgccgg    2040
tgctgtgcca ggcccacggc ttgaccccgg agcaggtggt ggccatcgcc agccacgatg    2100
gcggcaagca ggcgctggag acggtccagc ggctgttgcc ggtgctgtgc caggcccacg    2160
gcttgacccc ggagcaggtg gtggccatcg ccagccacga tggcggcaag caggcgctgg    2220
agacggtcca gcggctgttg ccggtgctgt gccaggccca cggcttgacc ccggagcagg    2280
tggtggccat cgccagcaat attggtggca agcaggcgct ggagacggtg caggcgctgt    2340
tgccggtgct gtgccaggcc cacggcttga ccccccagca ggtggtggcc atcgccagca    2400
ataatggtgg caagcaggcg ctggagacgt ccagcggct gttgccggtg ctgtgccagg    2460
cccacggctt gaccccggag caggtggtgg ccatcgccag ccacgatggc ggcaagcagg    2520
cgctggagac ggtccagcgg ctgttgccgg tgctgtgcca ggcccacggc ttgaccccgg    2580
agcaggtggt ggccatcgcc agcaatattg gtggcaagca ggcgctggag acggtgcagg    2640
cgctgttgcc ggtgctgtgc caggcccacg gcttgacccc tcagcaggtg gtggccatcg    2700
ccagcaatgg cggcggcagg ccggcgctgg agagcattgt tgcccagtta tctcgccctg    2760
atccggcgtt ggccgcgttg accaacgacc acctcgtcgc cttggcctgc ctcggcgggc    2820
gtcctgcgct ggatgcagtg aaaaagggat tgggggatcc tatcagccgt tcccagctgg    2880
tgaagtccga gctggaggag aagaaatccg agttgaggca caagctgaag tacgtgcccc    2940
acgagtacat cgagctgatc gagatcgccc ggaacagcac ccaggaccgt atcctggaga    3000
tgaaggtgat ggagttcttc atgaaggtgt acggctacag gggcaagcac ctgggcggct    3060
ccaggaagcc cgacgcgcc atctacaccg tgggctcccc catcgactac ggcgtgatcg    3120
tggacaccaa ggcctactcc ggcggctaca acctgcccat cggccaggcc gacgaaatgc    3180
agaggtacgt ggaggagaac cagaccagga caagcacat caaccccaac gagtggtgga    3240
aggtgtaccc ctccagcgtg accgagttca gttcctgtt cgtgtccggc cacttcaagg    3300
gcaactacaa ggcccagctg accaggctga accacatcac caactgcaac ggcgccgtgc    3360
tgtccgtgga ggagctcctg atcggcggcg agatgatcaa ggccggcacc ctgaccctgg    3420
aggaggtgag gaggaagttc aacaacggcg agatcaactt cgcggccgac tgataactcg    3480
agcgatcctc tagacgagct cctcgagcct gcagcagctg aagctttgga cttcttcgcc    3540
agaggtttgg tcaagtctcc aatcaaggtt gtcggcttgt ctaccttgcc agaaatttac    3600
gaaaagatgg aaaagggtca atcgttggt agatacgttg ttgacacttc taaataagcg    3660
aatttcttat gatttatgat ttttattatt aaataagtta taaaaaaaat aagtgtatac    3720
aaattttaaa gtgactctta ggttttaaaa cgaaaattct tattcttgag taactctttc    3780
ctgtaggtca ggttgctttc tcaggtatag catgaggtcg ctcttattga ccacacctct    3840
accggcatgc aagcttggcg taatcatggt catagctgtt tcctgtgtga aattgttatc    3900
cgctcacaat tccacacaac atacgagccg aagcataaa gtgtaaagcc tggggtgcct    3960
aatgagtgag ctaactcaca ttaattgcgt tgcgctcact gcccgctttc cagtcgggaa    4020
acctgtcgtg ccagcagatc tattacatta tgggtggtat gttggaataa aaatcaacta    4080
tcatctacta actagtattt acgttactag tatattatca tatacggtgt tagaagatga    4140
```

```
cgcaaatgat gagaaatagt catctaaatt agtggaagct gaaacgcaag gattgataat      4200
gtaataggat caatgaatat taacatataa aatgatgata ataatattta tagaattgtg      4260
tagaattgca gattcccttt tatggattcc taaatcctcg aggagaactt ctagtatatc      4320
tacataccta atattattgc cttattaaaa atggaatccc aacaattaca tcaaaatcca      4380
cattctcttc aaaatcaatt gtcctgtact tccttgttca tgtgtgttca aaaacgttat      4440
atttatagga taattatact ctatttctca acaagtaatt ggttgtttgg ccgagcggtc      4500
taaggcgcct gattcaagaa atatcttgac cgcagttaac tgtgggaata ctcaggtatc      4560
gtaagatgca agagttcgaa tctcttagca accattattt ttttcctcaa cataacgaga      4620
acacacaggg gcgctatcgc acagaatcaa attcgatgac tggaaatttt ttgttaattt      4680
cagaggtcgc ctgacgcata tcctttttc aactgaaaaa ttgggagaaa aaggaaaggt      4740
gagagccgcg gaaccggctt ttcatataga atagagaagc gttcatgact aaatgcttgc      4800
atcacaatac ttgaagttga caatattatt taaggaccta ttgttttttc caataggtgg      4860
ttagcaatcg tcttactttc taacttttct tacctttac atttcagcaa tatatatata      4920
tatatttcaa ggatatacca ttctaatgtc tgcccctaag aagatcgtcg ttttgccagg      4980
tgaccacgtt ggtcaagaaa tcacagccga agccattaag gttcttaaag ctatttctga      5040
tgttcgttcc aatgtcaagt tcgatttcga aaatcattta attggtggtg ctgctatcga      5100
tgctacaggt gtcccacttc cagatgaggc gctggaagcc tccaagaagg ttgatgccgt      5160
tttgttaggt gctgtgggtg gtcctaaatg gggtaccggt agtgttagac ctgaacaagg      5220
tttactaaaa atccgtaaag aacttcaatt gtacgccaac ttaagaccat gtaactttgc      5280
atccgactct cttttagact tatctccaat caagccacaa tttgctaaag gtactgactt      5340
cgttgttgtc agagaattag tgggaggtat ttactttggt aagagaaagg aagacgatgg      5400
tgatggtgtc gcttgggata gtgaacaata caccgttcca gaagtgcaaa gaatcacaag      5460
aatggccgct ttcatggccc tacaacatga gccaccattg cctatttggt ccttggataa      5520
agctaatgtt ttggcctctt caagattatg gagaaaaact gtggaggaaa ccatcaagaa      5580
cgaattccct acattgaagg ttcaacatca attgattgat tctgccgcca tgatcctagt      5640
taagaaccca acccacctaa atggtattat aatcaccagc aacatgtttg gtgatatcat      5700
ctccgatgaa gcctccgtta tcccaggttc cttgggtttg ttgccatctg cgtccttggc      5760
ctctttgcca gacaagaaca ccgcatttgg tttgtacgaa ccatgccacg gttctgctcc      5820
agatttgcca aagaataagg tcaaccctat cgccactatc ttgtctgctg caatgatgtt      5880
gaaattgtca ttgaacttgc ctgaagaagg taaggccatt gaagatgcag ttaaaaaggt      5940
tttggatgca ggtatcagaa ctggtgattt aggtggttcc aacagtacca cggaagtcgg      6000
tgatgctgtc gccgaagaag ttaagaaaat ccttgcttaa aaagattctc ttttttttatg      6060 atatttgtac ataaacttta taaatgaaat tcataataga aacgacacga aattacaaaa      6120
tggaatatgt tcatagggta gacgaaacta tatacgcaat ctacatacat ttatcaagaa      6180
ggagaaaaag gaggatgtaa aggaatacag gtaagcaaat tgatactaat ggctcaacgt      6240
gataaggaaa agaattgca ctttaacatt aatattgaca aggaggaggg caccacacaa      6300
aaagttaggt gtaacagaaa atcatgaaac tatgattcct aatttatata ttggaggatt      6360
ttctctaaaa aaaaaaaaat acaacaaata aaaacactc aatgacctga ccatttgatg      6420
gagtttaagt caataccttc ttgaaccatt tcccataatg gtgaaagttc cctcaagaat      6480
```

```
tttactctgt cagaaacggc cttaacgacg tagtcgacct cctcttcagt actaaatcta    6540
ccaataccaa atctgatgga agaatgggct aatgcatcat ccttacccag cgcatgtaaa    6600
acataagaag gttctaggga agcagatgta caggctgaac ccgaggataa tgcgatatcc    6660
cttagtgcca tcaataaaga ttctccttcc acgtaggcga agaaacgtt aacacaccct    6720
ggataacgat gatctggaga tccgttcaac gtggtatgtt cagcggataa tagacctttg    6780
actaatttat cggatagtct tttgatgtga gcttggtcgt tgtcaaattc tttcttcatc    6840
aatctcgcag cttcaccaaa tcccgctacc aatgggggg ccaaagtacc agatctgctg    6900
cattaatgaa tcggccaacg cgcggggaga ggcggtttgc gtattgggcg ctcttccgct    6960
tcctcgctca ctgactcgct gcgctcggtc gttcggctgc ggcgagcggt atcagcatcg    7020
atgaattcca cggactatag actatactag tatactccgt ctactgtacg atacacttcc    7080
gctcaggtcc ttgtcctttta acgaggcctt accactcttt tgttactcta ttgatccagc    7140
tcagcaaagg cagtgtgatc taagattcta tcttcgcgat gtagtaaaac tagctagacc    7200
gagaaagaga ctagaaatgc aaaaggcact tctacaatgg ctgccatcat tattatccga    7260
tgtgacgctg cagcttctca atgatattcg aatacgcttt gaggagatac agcctaatat    7320
ccgacaaact gttttacaga tttacgatcg tacttgttac ccatcattga attttgaaca    7380
tccgaacctg ggagttttcc ctgaaacaga tagtatattt gaacctgtat aataatatat    7440
agtctagcgc tttacggaag acaatgtatg tatttcggtt cctggagaaa ctattgcatc    7500
tattgcatag gtaatcttgc acgtcgcatc cccggttcat tttctgcgtt ccatcttgc    7560
acttcaatag catatctttg ttaacgaagc atctgtgctt cattttgtag aacaaaaatg    7620
caacgcgaga gcgctaattt ttcaaacaaa gaatctgagc tgcattttta cagaacagaa    7680
atgcaacgcg aaagcgctat tttaccaacg aagaatctgt gcttcatttt tgtaaaacaa    7740
aaatgcaacg cgagagcgct aatttttcaa acaaagaatc tgagctgcat ttttacagaa    7800
cagaaatgca acgcgagagc gctattttac caacaaagaa tctatacttc ttttttgttc    7860
tacaaaaatg catcccgaga gcgctatttt tctaacaaag catcttagat tactttttt    7920
ctcctttgtg cgctctataa tgcagtctct tgataacttt ttgcactgta ggtccgttaa    7980
ggttagaaga aggctacttt ggtgtctatt ttctcttcca taaaaaaagc ctgactccac    8040
ttcccgcgtt tactgattac tagcgaagct gcgggtgcat ttttttcaaga taaaggcatc    8100
cccgattata ttctataccg atgtggattg cgcatacttt gtgaacagaa agtgatagcg    8160
ttgatgattc ttcattggtc agaaaattat gaacggtttc ttctattttg tctctatata    8220
ctacgtatag gaaatgttta cattttcgta ttgttttcga ttcactctat gaatagttct    8280
tactacaatt tttttgtcta aagagtaata ctagagataa acataaaaaa tgtagaggtc    8340
gagtttagat gcaagttcaa ggagcgaaag gtggatgggt aggttatata gggatatagc    8400
acagagatat atagcaaaga gatacttttg agcaatgttt gtggaagcgg tattcgcaat    8460
attttagtag ctcgttacag tccggtgcgt ttttggtttt ttgaaagtgc gtcttcagag    8520
cgcttttggt tttcaaaagc gctctgaagt tcctatactt tctagagaat aggaacttcg    8580
gaataggaac ttcaaagcgt ttccgaaaac gagcgcttcc gaaaatgcaa cgcgagctgc    8640
gcacatacag ctcactgttc acgtcgcacc tatatctgcg tgttgcctgt atatatatat    8700
acatgagaag aacggcatag tgcgtgttta tgcttaaatg cgtacttata tgcgtctatt    8760
tatgtaggat gaaaggtagt ctagtacctc ctgtgatatt atcccattcc atgcggggta    8820
tcgtatgctt ccttcagcac tacccttag ctgttctata tgctgccact cctcaattgg    8880
```

```
attagtctca tccttcaatg ctatcatttc ctttgatatt ggatcatatg catagtaccg   8940
agaaactagt gcgaagtagt gatcaggtat tgctgttatc tgatgagtat acgttgtcct   9000
ggccacggca gaagcacgct tatcgctcca atttcccaca acattagtca actccgttag   9060
gcccttcatt gaaagaaatg aggtcatcaa atgtcttcca atgtgagatt ttgggccatt   9120
ttttatagca aagattgaat aaggcgcatt tttcttcaaa gctttattgt acgatctgac   9180
taagttatct tttaataatt ggtattcctg tttattgctt gaagaattgc cggtcctatt   9240
tactcgtttt aggactggtt cagaattcat cgatgctcac tcaaaggtcg gtaatacggt   9300
tatccacaga atcaggggat aacgcaggaa agaacatgtg agcaaaaggc cagcaaaagg   9360
ccaggaaccg taaaaaggcc gcgttgctgg cgttttttcca taggctccgc cccctgacg   9420
agcatcacaa aaatcgacgc tcaagtcaga ggtggcgaaa cccgacagga ctataaagat   9480
accaggcgtt tccccctgga agctccctcg tgcgctctcc tgttccgacc ctgccgctta   9540
ccggatacct gtccgccttt ctcccttcgg aagcgtggc gctttctcat agctcacgct   9600
gtaggtatct cagttcggtg taggtcgttc gctccaagct gggctgtgtg cacgaacccc   9660
ccgttcagcc cgaccgctgc gccttatccg gtaactatcg tcttgagtcc aacccggtaa   9720
gacacgactt atcgccactg gcagcagcca ctggtaacag gattagcaga gcgaggtatg   9780
taggcggtgc tacagagttc ttgaagtggt ggcctaacta cggctacact agaaggacag   9840
tatttggtat ctgcgctctg ctgaagccag ttaccttcgg aaaaagagtt ggtagctctt   9900
gatccggcaa acaaaccacc gctggtagcg gtggtttttt tgtttgcaag cagcagatta   9960
cgcgcagaaa aaaggatct caagaagatc ctttgatctt ttctacgggg tctgacgctc  10020
agtggaacga aaactcacgt taagggattt tggtcatgag attatcaaaa aggatcttca  10080
cctagatcct tttaaattaa aaatgaagtt ttaaatcaat ctaaagtata tatgagtaaa  10140
cttggtctga cagttaccaa tgcttaatca gtgaggcacc tatctcagcg atctgtctat  10200
ttcgttcatc catagttgcc tgactccccg tcgtgtagat aactacgata cgggagggct  10260
taccatctgg ccccagtgct gcaatgatac cgcgagaccc acgctcaccg gctccagatt  10320
tatcagcaat aaaccagcca gccggaaggg ccgagcgcag aagtggtcct gcaactttat  10380
ccgcctccat ccagtctatt aattgttgcc gggaagctag agtaagtagt tcgccagtta  10440
atagtttgcg caacgttgtt gccattgcta caggcatcgt ggtgtcacgc tcgtcgtttg  10500
gtatggcttc attcagctcc ggttcccaac gatcaaggcg agttacatga tcccccatgt  10560
tgtgcaaaaa agcggttagc tccttcggtc ctccgatcgt tgtcagaagt aagttggccg  10620
cagtgttatc actcatggtt atggcagcac tgcataattc tcttactgtc atgccatccg  10680
taagatgctt ttctgtgact ggtgagtact caaccaagtc attctgagaa tagtgtatgc  10740
ggcgaccgag ttgctcttgc ccggcgtcaa tacgggataa taccgcgcca catagcagaa  10800
ctttaaaagt gctcatcatt ggaaaacgtt cttcggggcg aaaactctca aggatcttac  10860
cgctgttgag atccagttcg atgtaaccca ctcgtgcacc caactgatct tcagcatctt  10920
ttactttcac cagcgtttct gggtgagcaa aaacaggaag gcaaaatgcc gcaaaaaagg  10980
gaataagggc gacacggaaa tgttgaatac tcatactctt ccttttttcaa tattattgaa  11040
gcatttatca gggttattgt ctcatgagcg gatacatatt tgaatgtatt tagaaaaata  11100
aacaaatag                                                          11109
```

<210> SEQ ID NO 3

```
<211> LENGTH: 597
<212> TYPE: DNA
<213> ORGANISM: Flavovacterium

<400> SEQUENCE: 3
cagctggtga agtccgagct ggaggagaag aaatccgagt tgaggcacaa gctgaagtac      60
gtgccccacg agtacatcga gctgatcgag atcgcccgga acagcaccca ggaccgtatc    120
ctggagatga aggtgatgga gttcttcatg aaggtgtacg gctacagggg caagcacctg    180
ggcggctcca ggaagcccga cggcgccatc tacaccgtgg gctcccccat cgactacggc    240
gtgatcgtgg acaccaaggc ctactccggc ggctacaacc tgcccatcgg ccaggccgac    300
gaaatgcaga ggtacgtgga ggagaaccag accaggaaca agcacatcaa ccccaacgag    360
tggtggaagg tgtacccctc cagcgtgacc gagttcaagt tcctgttcgt gtccggccac    420
ttcaagggca actacaaggc ccagctgacc aggctgaacc acatcaccaa ctgcaacggc    480
gccgtgctgt ccgtggagga gctcctgatc ggcggcgaga tgatcaaggc cggcaccctg    540
accctggagg aggtgaggag gaagttcaac aacggcgaga tcaacttcgc ggccgac       597

<210> SEQ ID NO 4
<211> LENGTH: 15
<212> TYPE: DNA
<213> ORGANISM: Artificial
<220> FEATURE:
<223> OTHER INFORMATION: DNA target site of the left-hand TALE of Figure
      1B

<400> SEQUENCE: 4
gtgatccccc cagca                                                       15

<210> SEQ ID NO 5
<211> LENGTH: 15
<212> TYPE: DNA
<213> ORGANISM: Artificial
<220> FEATURE:
<223> OTHER INFORMATION: Sequence complementary to the DNA target site
      of SEQ ID NO: 4

<400> SEQUENCE: 5
tgctgggggg atcac                                                       15

<210> SEQ ID NO 6
<211> LENGTH: 5
<212> TYPE: DNA
<213> ORGANISM: Artificial
<220> FEATURE:
<223> OTHER INFORMATION: portion of the DNA target site of SEQ ID NO: 4
      that is the sequence of the 5' end of the DNA tandem repeat

<400> SEQUENCE: 6 cagca                                                                   5

<210> SEQ ID NO 7
<211> LENGTH: 10
<212> TYPE: DNA
<213> ORGANISM: Artificial
<220> FEATURE:
<223> OTHER INFORMATION: portion of the DNA target site of SEQ ID NO: 4
      that is the gene sequence that is immediately adjacent to the 5'
      end of the tandem repeat (outside of the tandem repeat sequence)

<400> SEQUENCE: 7
gtgatccccc                                                             10
```

```
<210> SEQ ID NO 8
<211> LENGTH: 20
<212> TYPE: DNA
<213> ORGANISM: Artificial
<220> FEATURE:
<223> OTHER INFORMATION: spacer of Figure 1B

<400> SEQUENCE: 8
gcagcagcag cagcagcagc                                              20

<210> SEQ ID NO 9
<211> LENGTH: 20
<212> TYPE: DNA
<213> ORGANISM: Artificial
<220> FEATURE:
<223> OTHER INFORMATION: sequence of the spacer on the complementary
      strand

<400> SEQUENCE: 9
gctgctgctg ctgctgctgc                                              20

<210> SEQ ID NO 10
<211> LENGTH: 15
<212> TYPE: DNA
<213> ORGANISM: Artificial
<220> FEATURE:
<223> OTHER INFORMATION: DNA target site of the right-hand TALE of
      Figure 1B

<400> SEQUENCE: 10
gctgctgctg ctgct                                                   15

<210> SEQ ID NO 11
<211> LENGTH: 15
<212> TYPE: DNA
<213> ORGANISM: Artificial
<220> FEATURE:
<223> OTHER INFORMATION: Sequence complementary to the DNA target site
      of SEQ ID NO: 10

<400> SEQUENCE: 11
agcagcagca gcagc                                                   15

<210> SEQ ID NO 12
<211> LENGTH: 65
<212> TYPE: DNA
<213> ORGANISM: Artificial
<220> FEATURE:
<223> OTHER INFORMATION: Split left TALE DNA-binding domain of Figure 1B

<400> SEQUENCE: 12
tcgctgcagg tcggcctcag cctggccgaa agaaagaaat ggtctgtgat cccccccagca  60 gcagc                                                              65

<210> SEQ ID NO 13
<211> LENGTH: 65
<212> TYPE: DNA
<213> ORGANISM: Artificial
<220> FEATURE:
<223> OTHER INFORMATION: Sequence complementary to SEQ ID NO: 12

<400> SEQUENCE: 13
gctgctgctg gtccagccgg agtcggaccg gctttctttc tttaccagac actaggggc   60 agcga                                                              65
```

```
<210> SEQ ID NO 14
<211> LENGTH: 27
<212> TYPE: DNA
<213> ORGANISM: Artificial
<220> FEATURE:
<223> OTHER INFORMATION: CTG repeat

<400> SEQUENCE: 14
ctgctgctgc tgctgctgct gctgctg                                        27

<210> SEQ ID NO 15
<211> LENGTH: 65
<212> TYPE: DNA
<213> ORGANISM: Artificial
<220> FEATURE:
<223> OTHER INFORMATION: DNA comprising a DNA direct tandem repeat
      consisting of 9 copies of the unit CTG

<400> SEQUENCE: 15
tagccgggaa tgctgctgct gctgctgctg ctgctgctgg ggggatcaca gaccatttct    60
ttctt                                                                65

<210> SEQ ID NO 16
<211> LENGTH: 68
<212> TYPE: DNA
<213> ORGANISM: Artificial
<220> FEATURE:
<223> OTHER INFORMATION: DNA comprising a DNA direct tandem repeat
      consisting of 9 copies of the unit CTG

<400> SEQUENCE: 16
tagccgggaa tgctgctgct gctgctgctg ctgctgctgg ggggatcaca tacttttttt    60
ttctttcg                                                             68

<210> SEQ ID NO 17
<211> LENGTH: 19
<212> TYPE: DNA
<213> ORGANISM: Artificial
<220> FEATURE:
<223> OTHER INFORMATION: mutation detected in yeast

<400> SEQUENCE: 17
aaaaaaaaaa aaaaaaaaa                                                 19

<210> SEQ ID NO 18
<211> LENGTH: 24
<212> TYPE: DNA
<213> ORGANISM: Artificial
<220> FEATURE:
<223> OTHER INFORMATION: mutation detected in yeast

<400> SEQUENCE: 18
aaaaaaaaaa aaaaaaaaaa aaaa                                           24

<210> SEQ ID NO 19
<211> LENGTH: 19
<212> TYPE: DNA
<213> ORGANISM: Artificial
<220> FEATURE:
<223> OTHER INFORMATION: mutation detected in yeast

<400> SEQUENCE: 19
tttttttttt ttttttttt                                                 19
```

```
<210> SEQ ID NO 20
<211> LENGTH: 13
<212> TYPE: DNA
<213> ORGANISM: Artificial
<220> FEATURE:
<223> OTHER INFORMATION: mutation detected in yeast

<400> SEQUENCE: 20
tttttttttt ttt                                                           13

<210> SEQ ID NO 21
<211> LENGTH: 15
<212> TYPE: DNA
<213> ORGANISM: Artificial
<220> FEATURE:
<223> OTHER INFORMATION: mutation detected in yeast

<400> SEQUENCE: 21
aagaaaaaaa aaaaa                                                         15

<210> SEQ ID NO 22
<211> LENGTH: 5
<212> TYPE: PRT
<213> ORGANISM: Artificial
<220> FEATURE:
<223> OTHER INFORMATION: linker

<400> SEQUENCE: 22

Gln Gly Pro Ser Gly
1               5

<210> SEQ ID NO 23
<211> LENGTH: 34
<212> TYPE: DNA
<213> ORGANISM: Artificial
<220> FEATURE:
<223> OTHER INFORMATION: DNA comprising a DNA direct tandem repeat
      consisting of 8 copies of the unit CAG

<400> SEQUENCE: 23
gtgatccccc cagcagcagc agcagcagca gcag                                    34

<210> SEQ ID NO 24
<211> LENGTH: 270
<212> TYPE: PRT
<213> ORGANISM: Artificial
<220> FEATURE:
<223> OTHER INFORMATION: TALE tandem repeat consisting of 8 copies of
      the unit of SEQ ID NO: 25 (the RVDs being HD, NG, NI, NN, NS, N*,
      HG and H* respectively)

<400> SEQUENCE: 24

Leu Thr Pro Glu Gln Val Val Ala Ile Ala Ser His Asp Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser Asn
65                  70                  75                  80

Ile Gly Gly Lys Gln Ala Leu Glu Thr Val Gln Arg Leu Leu Pro Val
                85                  90                  95
```

```
Leu Cys Gln Ala His Gly Leu Thr Pro Glu Gln Val Val Ala Ile Ala
            100                 105                 110

Ser Asn Asn Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser Asn Ser Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn Gly Gly Lys Gln Ala Leu Glu Thr Val Gln
            180                 185                 190

Arg Leu Leu Pro Val Leu Cys Gln Ala His Gly Leu Thr Pro Glu Gln
            195                 200                 205

Val Val Ala Ile Ala Ser His Gly Gly Lys Gln Ala Leu Glu Thr
210                 215                 220

Val Gln Arg Leu Leu Pro Val Leu Cys Gln Ala His Gly Leu Thr Pro
225                 230                 235                 240

Glu Gln Val Val Ala Ile Ala Ser His Gly Gly Lys Gln Ala Leu Glu
                245                 250                 255

Thr Val Gln Arg Leu Leu Pro Val Leu Cys Gln Ala His Gly
            260                 265                 270

<210> SEQ ID NO 25
<211> LENGTH: 34
<212> TYPE: PRT
<213> ORGANISM: Artificial
<220> FEATURE:
<223> OTHER INFORMATION: TAL effector tandem repeat unit [XX is selected
      from the group consisting of HD, NG, NI, NN, NS, N*, HG, H*, IG,
      HA, ND, NK, HI, HN, NA, SN and YG (the symbol * denotes that the
      second X is missing)]
<220> FEATURE:
<221> NAME/KEY: MISC_FEATURE
<222> LOCATION: (12)..(13)
<223> OTHER INFORMATION: XX is the RVD of the TAL effector tandem repat
      unit; XX selected from the group consisting of HD, NG, NI, NN, NS,
      N*, HG, H*, IG, HA, ND, NK, HI, HN, NA, SN and YG (the symbol *
      denotes that the second X is missing)

<400> SEQUENCE: 25

Leu Thr Pro Glu Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 26
<211> LENGTH: 34
<212> TYPE: PRT
<213> ORGANISM: Artificial
<220> FEATURE:
<223> OTHER INFORMATION: TAL effector tandem repeat unit [XX is selected
      from the group consisting of HD, NG, NI, NN, NS, N*, HG, H*, IG,
      HA, ND, NK, HI, HN, NA, SN and YG (the symbol * denotes that the
      second X is missing)]
<220> FEATURE:
<221> NAME/KEY: MISC_FEATURE
<222> LOCATION: (12)..(13)
<223> OTHER INFORMATION: XX is the RVD of the TAL effector tandem repeat
      unit; XX is selected from the group consisting of HD, NG, NI, NN,
      NS, N*, HG, H*, IG, HA, ND, NK, HI, HN, NA, SN and YG (the symbol
      * denotes that the second X is missing)]
```

```
<400> SEQUENCE: 26

Leu Thr Pro Asp Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 27
<211> LENGTH: 39
<212> TYPE: DNA
<213> ORGANISM: Artificial
<220> FEATURE:
<223> OTHER INFORMATION: CAG repeat

<400> SEQUENCE: 27
cagcagcagc agcagcagca gcagcagcag cagcagcag                        39

<210> SEQ ID NO 28
<211> LENGTH: 87
<212> TYPE: DNA
<213> ORGANISM: Artificial
<220> FEATURE:
<223> OTHER INFORMATION: CAG repeat

<400> SEQUENCE: 28
cagcagcagc agcagcagca gcagcagcag cagcagcagc agcagcagca gcagcagcag   60
cagcagcagc agcagcagca gcagcag                                      87

<210> SEQ ID NO 29
<211> LENGTH: 45
<212> TYPE: DNA
<213> ORGANISM: Artificial
<220> FEATURE:
<223> OTHER INFORMATION: CAG repeat

<400> SEQUENCE: 29
cagcagcagc agcagcagca gcagcagcag cagcagcagc agcag                  45

<210> SEQ ID NO 30
<211> LENGTH: 9
<212> TYPE: DNA
<213> ORGANISM: Artificial
<220> FEATURE:
<223> OTHER INFORMATION: CAG repeat

<400> SEQUENCE: 30 cagcagcag                                                          9

<210> SEQ ID NO 31
<211> LENGTH: 366
<212> TYPE: DNA
<213> ORGANISM: Artificial
<220> FEATURE:
<223> OTHER INFORMATION: CTG repeat

<400> SEQUENCE: 31
ctgctgctgc tgctgctgct gctgctgctg ctgctgctgc tgctgctgct gctgctgctg   60
ctgctgctgc tgctgctgct gctgctgctg ctgctgctgc tgctgctgct gctgctgctg  120
ctgctgctgc tgctgctgct gctgctgctg ctgctgctgc tgctgctgct gctgctgctg  180
ctgctgctgc tgctgctgct gctgctgctg ctgctgctgc tgctgctgct gctgctgctg  240
ctgctgctgc tgctgctgct gctgctgctg ctgctgctgc tgctgctgct gctgctgctg  300
```

```
ctgctgctgc tgctgctgct gctgctgctg ctgctgctgc tgctgctgct gctgctgctg    360
ctgctg                                                                366
```

<210> SEQ ID NO 32
<211> LENGTH: 216
<212> TYPE: DNA
<213> ORGANISM: Artificial
<220> FEATURE:
<223> OTHER INFORMATION: CTG repeat

<400> SEQUENCE: 32

```
ctgctgctgc tgctgctgct gctgctgctg ctgctgctgc tgctgctgct gctgctgctg     60
ctgctgctgc tgctgctgct gctgctgctg ctgctgctgc tgctgctgct gctgctgctg    120
ctgctgctgc tgctgctgct gctgctgctg ctgctgctgc tgctgctgct gctgctgctg    180
ctgctgctgc tgctgctgct gctgctgctg ctgctg                              216
```

<210> SEQ ID NO 33
<211> LENGTH: 96
<212> TYPE: DNA
<213> ORGANISM: Artificial
<220> FEATURE:
<223> OTHER INFORMATION: CTG repeat

<400> SEQUENCE: 33

```
ctgctgctgc tgctgctgct gctgctgctg ctgctgctgc tgctgctgct gctgctgctg     60
ctgctgctgc tgctgctgct gctgctgctg ctgctg                               96
```

<210> SEQ ID NO 34
<211> LENGTH: 6
<212> TYPE: DNA
<213> ORGANISM: Artificial
<220> FEATURE:
<223> OTHER INFORMATION: CTG repeat

<400> SEQUENCE: 34

```
ctgctg                                                                 6
```

<210> SEQ ID NO 35
<211> LENGTH: 6
<212> TYPE: DNA
<213> ORGANISM: Artificial
<220> FEATURE:
<223> OTHER INFORMATION: CTG repeat

<400> SEQUENCE: 35

```
cagcag                                                                 6
```

<210> SEQ ID NO 36
<211> LENGTH: 4
<212> TYPE: DNA
<213> ORGANISM: Artificial
<220> FEATURE:
<223> OTHER INFORMATION: CTG repeat

<400> SEQUENCE: 36

```
gcag                                                                   4
```

<210> SEQ ID NO 37
<211> LENGTH: 366
<212> TYPE: DNA
<213> ORGANISM: Artificial
<220> FEATURE:

<223> OTHER INFORMATION: GAL10 enhancer

<400> SEQUENCE: 37

| | | |
|---|---|---|
| gatcaaaaat catcgcttcg ctgattaatt accccagaaa taaggctaaa aaactaatcg | 60 | |
| cattatcatc ctatggttgt taatttgatt cgttcatttg aaggtttgtg gggccaggtt | 120 | |
| actgccaatt tttcctcttc ataaccataa aagctagtat tgtagaatct ttattgttcg | 180 | |
| gagcagtgcg gcgcgaggca catctgcgtt tcaggaacgc gaccggtgaa gacgaggacg | 240 | |
| cacggaggag agtcttcctt cggagggctg tcacccgctc ggcggcttct aatccgtact | 300 | |
| tcaatatagc aatgagcagt taagcgtatt actgaaagtt ccaaagagaa ggttttttta | 360 | |
| ggctaa | 366 | |

<210> SEQ ID NO 38
<211> LENGTH: 240
<212> TYPE: DNA
<213> ORGANISM: Artificial
<220> FEATURE:
<223> OTHER INFORMATION: CYC1 promoter

<400> SEQUENCE: 38

| | |
|---|---|
| tcgacctcga gcagatccgc caggcgtgta tatagcgtgg atggccaggc aactttagtg | 60 |
| ctgacacata caggcatata tatatgtgtg cgacgacaca tgatcatatg gcatgcatgt | 120 |
| gctctgtatg tatataaaac tcttgttttc ttcttttctc taaatattct ttccttatac | 180 |
| attaggtcct ttgtagcata aattactata cttctataga cacgcaaaca caaatacaca | 240 |

<210> SEQ ID NO 39
<211> LENGTH: 2829
<212> TYPE: DNA
<213> ORGANISM: Artificial
<220> FEATURE:
<223> OTHER INFORMATION: sequence coding for the TALEN arm that
 recognizes the DNA target site of SEQ ID NO: 10

<400> SEQUENCE: 39

| | |
|---|---|
| atgggcgatc ctaaaaagaa acgtaaggtc atcgataagg agaccgccgc tgccaagttc | 60 |
| gagagacagc acatggacag catcgatatc gccgatctac gcacgctcgg ctacagccag | 120 |
| cagcaacagg agaagatcaa accgaaggtt cgttcgacag tggcgcagca ccacgaggca | 180 |
| ctggtcggcc acgggtttac acacgcgcac atcgttgcgt taagccaaca cccggcagcg | 240 |
| ttagggaccg tcgctgtcaa gtatcaggac atgatcgcag cgttgccaga ggcgacacac | 300 |
| gaagcgatct tggcgtcgg caaacagtgg tccggcgcac gcgctctgga ggccttgctc | 360 |
| acggtggcgg gagagttgag aggtccaccg ttacagttgg acacaggcca acttctcaag | 420 |
| attgcaaaac gtgcggcgt gaccgcagtg gaggcagtgc atgcatggcg caatgcactg | 480 |
| acgggtgccc cgctcaactt gaccccccag caggtggtgg ccatcgccag caataatggt | 540 |
| ggcaagcagg cgctggagac ggtccagcgg ctgttgccgg tgctgtgcca ggcccacggc | 600 |
| ttgaccccgg agcaggtggt ggccatcgcc agccacgatg gcggcaagca ggcgctggag | 660 |
| acggtccagc ggctgttgcc ggtgctgtgc caggcccacg gcttgacccc ccagcaggtg | 720 |
| gtggccatcg ccagcaatgg cggtggcaag caggcgctgg agacggtcca gcggctgttg | 780 |
| ccggtgctgt gccaggccca cggcttgacc ccccagcagg tggtggccat cgccagcaat | 840 |
| aatggtggca gcaggcgct ggagacggtc agcggctgt tgccggtgct gtgccaggcc | 900 |
| cacggcttga ccccggagca ggtggtggcc atcgccagcc acgatggcgg caagcaggcg | 960 |

```
ctggagacgg tccagcggct gttgccggtg ctgtgccagg cccacggctt gacccccag       1020 caggtggtgg ccatcgccag caatggcggt ggcaagcagg cgctggagac ggtccagcgg      1080
ctgttgccgg tgctgtgcca ggcccacggc ttgacccccc agcaggtggt ggccatcgcc      1140
agcaataatg gtggcaagca ggcgctggag acggtccagc ggctgttgcc ggtgctgtgc      1200
caggcccacg gcttgacccc ggagcaggtg gtggccatcg ccagccacga tggcggcaag      1260
caggcgctgg agacggtcca gcggctgttg ccggtgctgt gccaggccca cggcttgacc      1320
ccccagcagg tggtggccat cgccagcaat ggcggtggca agcaggcgct ggagacggtc      1380
cagcggctgt gccggtgct gtgccaggcc acggcttga ccccccagca ggtggtggcc       1440
atcgccagca ataatggtgg caagcaggcg ctggagacgg tccagcggct gttgccggtg      1500
ctgtgccagg cccacggctt gaccccggag caggtggtgg ccatcgccag ccacgatggc      1560
ggcaagcagg cgctggagac ggtccagcgg ctgttgccgg tgctgtgcca ggcccacggc      1620 ttgaccccc agcaggtggt ggccatcgcc agcaatggcg gtggcaagca ggcgctggag       1680
acggtccagc ggctgttgcc ggtgctgtgc caggcccacg gcttgacccc ccagcaggtg      1740
gtggccatcg ccagcaataa tggtggcaag caggcgctgg agacggtcca gcggctgttg      1800
ccggtgctgt gccaggccca cggcttgacc ccggagcagg tggtggccat cgccagccac      1860
gatggcggca agcaggcgct ggagacggtc cagcggctgt gccggtgct gtgccaggcc       1920 cacggcttga ccccccagca ggtggtggcc atcgccagca atggcggtgg caagcaggcg      1980
ctggagacgg tccagcggct gttgccggtg ctgtgccagg cccacggctt gacccctcag      2040
caggtggtgg ccatcgccag caatggcggc ggcaggccgg cgctggagag cattgttgcc      2100
cagttatctc gccctgatcc ggcgttggcc gcgttgacca acgaccacct cgtcgccttg      2160
gcctgcctcg gcgggcgtcc tgcgctggat gcagtgaaaa agggattggg ggatcctatc      2220
agccgttccc agctggtgaa gtccgagctg aggagaaga atccgagtt gaggcacaag        2280 ctgaagtacg tgccccacga gtacatcgag ctgatcgaga tcgcccggaa cagcacccag      2340
gaccgtatcc tggagatgaa ggtgatggag ttcttcatga aggtgtacgg ctacagggg       2400 aagcacctgg gcggctccag gaagcccgac ggcgccatct acaccgtggg ctcccccatc      2460
gactacggcg tgatcgtgga caccaaggcc tactccggcg gctacaacct gcccatcggc      2520
caggccgacg aaatgcagag gtacgtggag gagaaccaga ccaggaacaa gcacatcaac      2580
cccaacgagt ggtggaaggt gtaccctcc agcgtgaccg agttcaagtt cctgttcgtg       2640
tccggccact tcaagggcaa ctacaaggcc agctgacca ggctgaacca catcaccaac       2700
tgcaacggcg ccgtgctgtc cgtggaggag ctcctgatcg gcggcgagat gatcaaggcc      2760 ggcacccctga ccctggagga ggtgaggagg aagttcaaca cggcgagat caacttcgcg      2820 gccgactga                                                             2829
```

<210> SEQ ID NO 40
<211> LENGTH: 320
<212> TYPE: DNA
<213> ORGANISM: Artificial
<220> FEATURE:
<223> OTHER INFORMATION: ADH1 terminator

<400> SEQUENCE: 40

```
tattgaccac acctctaccg gcatgcaagc ttggcgtaat catggtcata gctgtttcct        60
gtgtgaaatt gttatccgct cacaattcca cacaacatac gagccggaag cataaagtgt       120
aaagcctggg gtgcctaatg agtgagctaa ctcacattaa ttgcgttgcg ctcactgccc       180
```

```
gctttccagt cgggaaacct gtcgtgccag cagatctgtt tagcttgcct cgtccccgcc      240
gggtcacccg gccagcgaca tggaggccca gaataccctc cttgacagtc ttgacgtgcg      300
cagctcaggg gcatgatgtg                                                 320
```

<210> SEQ ID NO 41
<211> LENGTH: 383
<212> TYPE: DNA
<213> ORGANISM: Artificial
<220> FEATURE:
<223> OTHER INFORMATION: TEF promoter

<400> SEQUENCE: 41

```
tgaggttctt ctttcatata cttcctttta aaatcttgct aggatacagt tctcacatca      60
catccgaaca taaacaacca tgcatgggta aggaaaagac tcacgtttcg aggccgcgat     120
taaattccaa catggatgct gatttatatg ggtataaatg ggctcgcgat aatgtcgggc     180
aatcaggtgc gacaatctat cgattgtatg ggaagcccga tgcgccagag ttgtttctga     240
aacatggcaa aggtagcgtt gccaatgatg ttacagatga tggtcaga ctaaactggc       300 tgacggaatt tatgcctctt ccgaccatca agcattttat ccgtactcct gatgatgcat     360
ggttactcac cactgcgatc ccc                                             383
```

<210> SEQ ID NO 42
<211> LENGTH: 807
<212> TYPE: DNA
<213> ORGANISM: Artificial
<220> FEATURE:
<223> OTHER INFORMATION: sequence coding for the KANMX selection marker

<400> SEQUENCE: 42

```
ggcaaaacag cattccaggt attagaagaa tatcctgatt caggtgaaaa tattgttgat      60
gcgctggcag tgttcctgcg ccggttgcat tcgattcctg tttgtaattg tcctttttaac    120 agcgatcgcg tatttcgcct cgctcaggcg caatcacgaa tgaataacgg tttggttgat     180
gcgagtgatt ttgatgacga gcgtaatggc tggcctgttg aacaagtctg gaaagaaatg     240
cataagcttt tgccattctc accggattca gtcgtcactc atggtgattt ctcacttgat     300
aaccttattt ttgacgaggg gaaattaata ggttgtattg atgttggacg agtcggaatc     360
gcagaccgat accaggatct tgccatccta tggaactgcc tcggtgagtt ttctccttca     420
ttacagaaac ggcttttttca aaaatatggt attgataatc ctgatatgaa taaattgcag    480
tttcatttga tgctcgatga ttttttctaa tcagtactga caataaaaag attcttgttt    540
tcaagaactt gtcatttgta tagttttttt atattgtagt tgttctattt taatcaaatg    600
ttagcgtgat ttatatttt tttcgcctcg acatcatctg cccagatgcg aagttaagtg     660
cgcagaaagt aatatcatgc gtcaatcgta tgtgaatgct ggtcgctata ctgctgtcga    720
ttcgatacta acgccgccat ccagtgtcga aaacgagctc gaattcatcg atgatatcag    780
atccactagt ggcctatgcg accgcgg                                        807
```

<210> SEQ ID NO 43
<211> LENGTH: 213
<212> TYPE: DNA
<213> ORGANISM: Artificial
<220> FEATURE:
<223> OTHER INFORMATION: TEF terminator

<400> SEQUENCE: 43

```
atctgccggt ctccctatag tgagtcgtat taatttcgat aagccaggtt aacctgcatt    60
aatgaatcgg ccaacgcgcg gggagaggcg gtttgcgtat tgggcgctct tccgcttcct   120
cgctcactga ctcgctgcgc tcggtcgttc ggctgcggcg agcggtatca gcatcgatga   180
attccacgga ctatagacta tactagtata ctc                                213

<210> SEQ ID NO 44
<211> LENGTH: 1345
<212> TYPE: DNA
<213> ORGANISM: Artificial
<220> FEATURE:
<223> OTHER INFORMATION: 2-Micron replication origin

<400> SEQUENCE: 44 gctattttc taacaaagca tcttagatta ctttttttct cctttgtgcg ctctataatg     60
cagtctcttg ataacttttt gcactgtagg tccgttaagg ttagaagaag ctactttgg   120 tgtctatttt ctcttccata aaaaagcct gactccactt cccgcgttta ctgattacta    180
gcgaagctgc gggtgcattt tttcaagata aaggcatccc cgattatatt ctataccgat   240
gtggattgcg catactttgt gaacagaaag tgatagcgtt gatgattctt cattggtcag   300
aaaattatga acgtttctt ctattttgtc tctatatact acgtatagga aatgtttaca    360
ttttcgtatt gttttcgatt cactctatga atagttctta ctacaatttt tttgtctaaa   420
gagtaatact agagataaac ataaaaatg tagaggtcga gtttagatgc aagttcaagg    480
agcgaaaggt ggatgggtag gttatatagg gatatagcac agagatatat agcaaagaga   540
tacttttgag caatgtttgt ggaagcggta ttcgcaatat tttagtagct cgttacagtc   600
cggtgcgttt ttggtttttt gaaagtgcgt cttcagagcg cttttggttt tcaaaagcgc   660
tctgaagttc ctatactttc tagagaatag gaacttcgga ataggaactt caaagcgttt   720
ccgaaaacga gcgcttccga aaatgcaacg cgagctgcgc acatacagct cactgttcac   780
gtcgcaccta tatctgcgtg ttgcctgtat atatatat atgagaagaa cggcatagtg    840
cgtgtttatg cttaaatgcg tacttatatg cgtctattta tgtaggatga aggtagtct    900 agtacctcct gtgatattat cccattccat gcggggtatc gtatgcttcc ttcagcacta   960 cccttagct gttctatatg ctgccactcc tcaattggat tagtctcatc cttcaatgct   1020
atcattccct tgatattgg atcatatgca tagtaccgag aaactagtgc gaagtagtga   1080
tcaggtattg ctgttatctg atgagtatac gttgtcctgg ccacggcaga agcacgctta   1140
tcgctccaat ttcccacaac attagtcaac tccgttaggc ccttcattga agaaatgag   1200 gtcatcaaat gtcttccaat gtgagatttt gggccatttt ttatagcaaa gattgaataa   1260
ggcgcatttt tcttcaaagc tttattgtac gatctgacta agttatcttt taataattgg   1320
tattcctgtt tattgcttga agaat                                         1345

<210> SEQ ID NO 45
<211> LENGTH: 1530
<212> TYPE: DNA
<213> ORGANISM: Artificial
<220> FEATURE:
<223> OTHER INFORMATION: sequence coding for the TAL effector tandem
      repeat of the TALEN arm that binds to the DNA target site of SEQ
      ID NO: 10 (15 adjacent units of 34 amino acids)

<400> SEQUENCE: 45
ttgacccccc agcaggtggt ggccatcgcc agcaataatg gtggcaagca ggcgctggag     60
acggtccagc ggctgttgcc ggtgctgtgc caggcccacg gcttgacccc ggagcaggtg    120
```

```
gtggccatcg ccagccacga tggcggcaag caggcgctgg agacggtcca gcggctgttg    180
ccggtgctgt gccaggccca cggcttgacc ccccagcagg tggtggccat cgccagcaat    240
ggcggtggca agcaggcgct ggagacggtc agcggctgt tgccggtgct gtgccaggcc    300
cacggcttga ccccccagca ggtggtggcc atcgccagca ataatggtgg caagcaggcg    360
ctggagacgg tccagcggct gttgccggtg ctgtgccagg cccacggctt gaccccggag    420
caggtggtgg ccatcgccag ccacgatggc ggcaagcagg cgctggagac ggtccagcgg    480
ctgttgccgg tgctgtgcca ggccacggc ttgaccccc agcaggtggt ggccatcgcc    540
agcaatggcg gtggcaagca ggcgctggag acggtccagc ggctgttgcc ggtgctgtgc    600
caggcccacg gcttgacccc cagcaggtg gtggccatcg ccagcaataa tggtggcaag    660 caggcgctg agacggtcca gcggctgttg ccggtgctgt gccaggccca cggcttgacc    720
ccggagcagg tggtggccat cgccagccac gatggcggca agcaggcgct ggagacggtc    780
cagcggctgt tgccggtgct gtgccaggcc cacggcttga ccccccagca ggtggtggcc    840
atcgccagca atggcggtgg caagcaggcg ctggagacgg tccagcggct gttgccggtg    900
ctgtgccagg cccacggctt gaccccccag caggtggtgg ccatcgccag caataatggt    960
ggcaagcagg cgctggagac ggtccagcgg ctgttgccgg tgctgtgcca ggcccacggc   1020
ttgaccccgg agcaggtggt ggccatcgcc agccacgatg gcggcaagca ggcgctggag   1080
acggtccagc ggctgttgcc ggtgctgtgc caggcccacg gcttgacccc ccagcaggtg   1140
gtggccatcg ccagcaatgg cggtggcaag caggcgctgg agacggtcca gcggctgttg   1200
ccggtgctgt gccaggccca cggcttgacc ccccagcagg tggtggccat cgccagcaat   1260
aatggtggca agcaggcgct ggagacggtc agcggctgt tgccggtgct gtgccaggcc   1320
cacggcttga ccccggagca ggtggtggcc atcgccagcc acgatggcgg caagcaggcg   1380
ctggagacgg tccagcggct gttgccggtg ctgtgccagg cccacggctt gaccccccag   1440
caggtggtgg ccatcgccag caatggcggt ggcaagcagg cgctggagac ggtccagcgg   1500
ctgttgccgg tgctgtgcca ggcccacggc                                    1530
```

<210> SEQ ID NO 46
<211> LENGTH: 34
<212> TYPE: PRT
<213> ORGANISM: Artificial
<220> FEATURE:
<223> OTHER INFORMATION: TAL effector tandem repeat unit [XX is selected
      from the group consisting of HD, NG, NI, NN, NS, N*, HG, H*, IG,
      HA, ND, NK, HI, HN, NA, SN and YG (the symbol * denotes that the
      second X is missing)]
<220> FEATURE:
<221> NAME/KEY: MISC_FEATURE
<222> LOCATION: (12)..(13)
<223> OTHER INFORMATION: XX is the RVD of the TAL effector tandem repeat
      unit; XX is selected from the group consisting of HD, NG, NI, NN,
      NS, N*, HG, H*, IG, HA, ND, NK, HI, HN, NA, SN and YG (the symbol
      * denotes that the second X is missing)

<400> SEQUENCE: 46

Leu Thr Pro Gln Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 47

```
<211> LENGTH: 60
<212> TYPE: DNA
<213> ORGANISM: Artificial
<220> FEATURE:
<223> OTHER INFORMATION: (non-specific) C-terminal truncated unit of 20
      amino acids of the TALEN arm that binds to the DNA target site of
      SEQ ID NO: 10

<400> SEQUENCE: 47
ttgacccctc agcaggtggt ggccatcgcc agcaatggcg gcggcaggcc ggcgctggag    60

<210> SEQ ID NO 48
<211> LENGTH: 20
<212> TYPE: PRT
<213> ORGANISM: Artificial
<220> FEATURE:
<223> OTHER INFORMATION: (non-specific) C-terminal truncated unit of 20
      amino acids of the TALEN arm that binds to the DNA target site of
      SEQ ID NO: 10

<400> SEQUENCE: 48

Leu Thr Pro Gln Gln Val Val Ala Ile Ala Ser Asn Gly Gly Gly Arg
1               5                   10                  15

Pro Ala Leu Glu
            20

<210> SEQ ID NO 49
<211> LENGTH: 199
<212> TYPE: PRT
<213> ORGANISM: Artificial
<220> FEATURE:
<223> OTHER INFORMATION: FokI monomer

<400> SEQUENCE: 49

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe Ala Ala Asp
        195
```

<210> SEQ ID NO 50
<211> LENGTH: 2811
<212> TYPE: DNA
<213> ORGANISM: Artificial
<220> FEATURE:
<223> OTHER INFORMATION: sequence coding for the TALEN arm that binds to the DNA target site of SEQ ID NO: 4

<400> SEQUENCE: 50

| | | | | | |
|---|---|---|---|---|---|
| atgggcgatc | ctaaaaagaa | acgtaaggtc | atcgattacc | catacgatgt | tccagattac | 60 |
| gctatcgata | tcgccgatct | acgcacgctc | ggctacagcc | agcagcaaca | ggagaagatc | 120 |
| aaaccgaagg | ttcgttcgac | agtggcgcag | caccacgagg | cactggtcgg | ccacgggttt | 180 |
| acacacgcgc | acatcgttgc | gttaagccaa | cacccggcag | cgttagggac | cgtcgctgtc | 240 |
| aagtatcagg | acatgatcgc | agcgttgcca | gaggcgacac | acgaagcgat | cgttggcgtc | 300 |
| ggcaaacagt | ggtccggcgc | acgcgctctg | gaggccttgc | tcacggtggc | gggagagttg | 360 |
| agaggtccac | cgttacagtt | ggacacaggc | caacttctca | agattgcaaa | acgtggcggc | 420 |
| gtgaccgcag | tggaggcagt | gcatgcatgg | cgcaatgcac | tgacgggtgc | cccgctcaac | 480 |
| ttgacccccc | agcaggtggt | ggccatcgcc | agcaataatg | gtggcaagca | ggcgctggag | 540 |
| acggtccagc | ggctgttgcc | ggtgctgtgc | caggcccacg | gcttgacccc | ccagcaggtg | 600 |
| gtggccatcg | ccagcaatgg | cggtggcaag | caggcgctgg | agacggtcca | gcggctgttg | 660 |
| ccggtgctgt | gccaggccca | cggcttgacc | cccagcagg | tggtggccat | cgccagcaat | 720 |
| aatggtggca | agcaggcgct | ggagacggtc | agcggctgt | tgccggtgct | gtgccaggcc | 780 |
| cacggcttga | ccccggagca | ggtggtggcc | atcgccagca | atattggtgg | caagcaggcg | 840 |
| ctggagacgg | tgcaggcgct | gttgccggtg | ctgtgccagg | cccacggctt | gacccccag | 900 |
| caggtggtgg | ccatcgccag | caatggcggt | ggcaagcagg | cgctggagac | ggtccagcgg | 960 |
| ctgttgccgg | tgctgtgcca | ggcccacggc | ttgaccccgg | agcaggtggt | ggccatcgcc | 1020 |
| agccacgatg | gcggcaagca | ggcgctggag | acggtccagc | ggctgttgcc | ggtgctgtgc | 1080 |
| caggcccacg | gcttgacccc | ggagcaggtg | gtggccatcg | ccagccacga | tggcggcaag | 1140 |
| caggcgctgg | agacggtcca | gcggctgttg | ccggtgctgt | gccaggccca | cggcttgacc | 1200 |
| ccggagcagg | tggtggccat | cgccagccac | gatggcggca | agcaggcgct | ggagacggtc | 1260 |
| cagcggctgt | tgccggtgct | gtgccaggcc | cacggcttga | ccccggagca | ggtggtggcc | 1320 |
| atcgccagcc | acgatggcgg | caagcaggcg | ctggagacgg | tccagcggct | gttgccggtg | 1380 |
| ctgtgccagg | cccacggctt | gaccccggag | caggtggtgg | ccatcgccag | ccacgatggc | 1440 |
| ggcaagcagg | cgctggagac | ggtccagcgg | ctgttgccgg | tgctgtgcca | ggcccacggc | 1500 |
| ttgaccccgg | agcaggtggt | ggccatcgcc | agccacgatg | gcggcaagca | ggcgctggag | 1560 |
| acggtccagc | ggctgttgcc | ggtgctgtgc | caggcccacg | gcttgacccc | ggagcaggtg | 1620 |
| gtggccatcg | ccagcaatat | tggtggcaag | caggcgctgg | agacggtgca | ggcgctgttg | 1680 |
| ccggtgctgt | gccaggccca | cggcttgacc | cccagcagg | tggtggccat | cgccagcaat | 1740 |
| aatggtggca | agcaggcgct | ggagacggtc | agcggctgt | tgccggtgct | gtgccaggcc | 1800 |
| cacggcttga | ccccggagca | ggtggtggcc | atcgccagcc | acgatggcgg | caagcaggcg | 1860 |
| ctggagacgg | tccagcggct | gttgccggtg | ctgtgccagg | cccacggctt | gacccccggag | 1920 |
| caggtggtgg | ccatcgccag | caatattggt | ggcaagcagg | cgctggagac | ggtgcaggcg | 1980 |
| ctgttgccgg | tgctgtgcca | ggcccacggc | ttgacccctc | agcaggtggt | ggccatcgcc | 2040 |

| | | | | |
|---|---|---|---|---|
| agcaatggcg | gcggcaggcc | ggcgctggag | agcattgttg | cccagttatc | tcgccctgat | 2100 |
| ccggcgttgg | ccgcgttgac | caacgaccac | ctcgtcgcct | tggcctgcct | cggcgggcgt | 2160 |
| cctgcgctgg | atgcagtgaa | aaagggattg | ggggatccta | tcagccgttc | ccagctggtg | 2220 |
| aagtccgagc | tggaggagaa | gaaatccgag | ttgaggcaca | agctgaagta | cgtgccccac | 2280 |
| gagtacatcg | agctgatcga | gatcgcccgg | aacagcaccc | aggaccgtat | cctggagatg | 2340 |
| aaggtgatgg | agttcttcat | gaaggtgtac | ggctacaggg | gcaagcacct | gggcggctcc | 2400 |
| aggaagcccg | acggcgccat | ctacaccgtg | ggctccccca | tcgactacgg | cgtgatcgtg | 2460 |
| gacaccaagg | cctactccgg | cggctacaac | ctgcccatcg | gccaggccga | cgaaatgcag | 2520 |
| aggtacgtgg | aggagaacca | gaccaggaac | aagcacatca | cccccaacga | gtggtggaag | 2580 |
| gtgtaccccct | ccagcgtgac | cgagttcaag | ttcctgttcg | tgtccggcca | cttcaagggc | 2640 |
| aactacaagc | ccagctgac | caggctgaac | cacatcacca | actgcaacgg | cgccgtgctg | 2700 |
| tccgtggagg | agctcctgat | cggcggcgag | atgatcaagg | ccggcaccct | gaccctggag | 2760 |
| gaggtgagga | ggaagttcaa | caacggcgag | atcaacttcg | cggccgactg | a | 2811 |

<210> SEQ ID NO 51
<211> LENGTH: 320
<212> TYPE: DNA
<213> ORGANISM: Artificial
<220> FEATURE:
<223> OTHER INFORMATION: ADH1 terminator

<400> SEQUENCE: 51

| | | | | |
|---|---|---|---|---|
| tttggacttc | ttcgccagag | gtttggtcaa | gtctccaatc | aaggttgtcg | gcttgtctac | 60 |
| cttgccagaa | atttacgaaa | agatggaaaa | gggtcaaatc | gttggtagat | acgttgttga | 120 |
| cacttctaaa | taagcgaatt | tcttatgatt | tatgattttt | attattaaat | aagttataaa | 180 |
| aaaaataagt | gtatacaaat | tttaaagtga | ctcttaggtt | ttaaaacgaa | aattcttatt | 240 |
| cttgagtaac | tctttcctgt | aggtcaggtt | gctttctcag | gtatagcatg | aggtcgctct | 300 |
| tattgaccac | acctctaccg | | | | | 320 |

<210> SEQ ID NO 52
<211> LENGTH: 1095
<212> TYPE: DNA
<213> ORGANISM: Artificial
<220> FEATURE:
<223> OTHER INFORMATION: sequence coding for the LEU2 selection marker

<400> SEQUENCE: 52

| | | | | |
|---|---|---|---|---|
| atgtctgccc | ctaagaagat | cgtcgttttg | ccaggtgacc | acgttggtca | agaaatcaca | 60 |
| gccgaagcca | ttaaggttct | taaagctatt | tctgatgttc | gttccaatgt | caagttcgat | 120 |
| ttcgaaaatc | atttaattgg | tggtgctgct | atcgatgcta | caggtgtccc | acttccagat | 180 |
| gaggcgctgg | aagcctccaa | gaaggttgat | gccgttttgt | taggtgctgt | gggtggtcct | 240 |
| aaatggggta | ccggtagtgt | tagacctgaa | caaggtttac | taaaaatccg | taaagaactt | 300 |
| caattgtacg | ccaacttaag | accatgtaac | tttgcatccg | actctctttt | agacttatct | 360 |
| ccaatcaagc | acaatttgc | taaaggtact | gacttcgttg | ttgtcagaga | attagtggga | 420 |
| ggtatttact | ttggtaagag | aaaggaagac | gatggtgatg | gtgtcgcttg | ggatagtgaa | 480 |
| caatacaccg | ttcagaaagt | gcaaagaatc | acaagaatgg | ccgctttcat | ggccctacaa | 540 |
| catgagccac | cattgcctat | ttggtccttg | gataaagcta | atgttttggc | ctcttcaaga | 600 |
| ttatggagaa | aaactgtgga | ggaaaccatc | aagaacgaat | tccctacatt | gaaggttcaa | 660 |

```
catcaattga ttgattctgc cgccatgatc ctagttaaga acccaaccca cctaaatggt      720
attataatca ccagcaacat gtttggtgat atcatctccg atgaagcctc cgttatccca      780
ggttccttgg gtttgttgcc atctgcgtcc ttggcctctt tgccagacaa gaacaccgca      840
tttggtttgt acgaaccatg ccacggttct gctccagatt tgccaaagaa taaggtcaac      900
cctatcgcca ctatcttgtc tgctgcaatg atgttgaaat tgtcattgaa cttgcctgaa      960
gaaggtaagg ccattgaaga tgcagttaaa aaggttttgg atgcaggtat cagaactggt     1020
gatttaggtg gttccaacag taccacggaa gtcggtgatg ctgtcgccga agaagttaag     1080
aaaatccttg cttaa                                                      1095

<210> SEQ ID NO 53
<211> LENGTH: 1345
<212> TYPE: DNA
<213> ORGANISM: Artificial
<220> FEATURE:
<223> OTHER INFORMATION: 2-Micron replication origin

<400> SEQUENCE: 53
aacgaagcat ctgtgcttca ttttgtagaa caaaaatgca acgcgagagc gctaattttt       60
caaacaaaga atctgagctg catttttaca gaacagaaat gcaacgcgaa agcgctattt      120
taccaacgaa gaatctgtgc ttcattttg taaaacaaaa atgcaacgcg agagcgctaa      180 ttttcaaac aaagaatctg agctgcattt ttacagaaca gaaatgcaac gcgagagcgc      240
tattttacca acaagaatc tatacttctt ttttgttcta caaaaatgca tcccgagagc      300 gctattttc taacaaagca tcttagatta cttttttct cctttgtgcg ctctataatg      360
cagtctcttg ataactttt gcactgtagg tccgttaagg ttagaagaag gctactttgg      420
tgtctatttt ctcttccata aaaaaagcct gactccactt cccgcgttta ctgattacta      480
gcgaagctgc gggtgcattt ttcaagata aaggcatccc cgattatatt ctataccgat      540
gtggattgcg catactttgt gaacagaaag tgatagcgtt gatgattctt cattggtcag      600
aaaattatga acggtttctt ctattttgtc tctatatact acgtatagga atgtttaca      660 ttttcgtatt gttttcgatt cactctatga atagttctta ctacaatttt tttgtctaaa      720
gagtaatact agagataaac ataaaaaatg tagaggtcga gtttagatgc aagttcaagg      780
agcgaaaggt ggatgggtag gttatatagg gatatagcac agagatatat agcaaagaga      840 tactttgag caatgtttgt ggaagcggta ttcgcaatat tttagtagct cgttacagtc      900
cggtgcgttt ttggtttttt gaaagtgcgt cttcagagcg cttttggttt tcaaaagcgc      960
tctgaagttc ctatactttc tagagaatag aacttcgga ataggaactt caaagcgttt     1020
ccgaaaacga gcgcttccga aaatgcaacg cgagctgcgc acatacagct cactgttcac     1080
gtcgcaccta tatctgcgtg ttgcctgtat atatatatac atgagaagaa cggcatagtg     1140
cgtgtttatg cttaaatgcg tacttatatg cgtctattta tgtaggatga aaggtagtct     1200
agtacctcct gtgatattat cccattccat gcggggtatc gtatgcttcc ttcagcacta     1260
ccctttagct gttctatatg ctgccactcc tcaattggat tagtctcatc cttcaatgct     1320
atcatttcct ttgatattgg atcat                                           1345

<210> SEQ ID NO 54
<211> LENGTH: 1530
<212> TYPE: DNA
<213> ORGANISM: Artificial
<220> FEATURE:
```

<223> OTHER INFORMATION: sequence coding for the TAL effector tandem repeat of the TALEN arm that binds to the DNA target site of SEQ ID NO: 4 (15 adjacent units of 34 amino acids)

<400> SEQUENCE: 54

```
ttgacccccc agcaggtggt ggccatcgcc agcaataatg gtggcaagca ggcgctggag    60
acggtccagc ggctgttgcc ggtgctgtgc caggcccacg gcttgacccc ccagcaggtg   120
gtggccatcg ccagcaatgg cggtggcaag caggcgctgg agacggtcca gcggctgttg   180
ccggtgctgt gccaggccca cggcttgacc cccagcagg tggtggccat cgccagcaat   240
aatggtggca agcaggcgct ggagacggtc agcggctgt tgccggtgct gtgccaggcc   300
cacggcttga ccccggagca ggtggtggcc atcgccagca atattggtgg caagcaggcg   360
ctggagacgg tgcaggcgct gttgccggtg ctgtgccagg cccacggctt gaccccccag   420
caggtggtgg ccatcgccag caatggcggt ggcaagcagg cgctggagac ggtccagcgg   480
ctgttgccgg tgctgtgcca ggcccacggc ttgaccccgg agcaggtggt ggccatcgcc   540
agccacgatg gcggcaagca ggcgctggag acggtccagc ggctgttgcc ggtgctgtgc   600
caggcccacg gcttgacccc ggagcaggtg gtggccatcg ccagccacga tggcggcaag   660
caggcgctgg agacggtcca gcggctgttg ccggtgctgt gccaggccca cggcttgacc   720
ccggagcagg tggtggccat cgccagccac gatggcggca agcaggcgct ggagacggtc   780
cagcggctgt tgccggtgct gtgccaggcc cacggcttga ccccggagca ggtggtggcc   840
atcgccagcc acgatggcgg caagcaggcg ctggagacgg tccagcggct gttgccggtg   900
ctgtgccagg cccacggctt gaccccggag caggtggtgg ccatcgccag ccacgatggc   960
ggcaagcagg cgctggagac ggtccagcgg ctgttgccgg tgctgtgcca ggcccacggc  1020
ttgaccccgg agcaggtggt ggccatcgcc agccacgatg gcggcaagca ggcgctggag  1080
acggtccagc ggctgttgcc ggtgctgtgc caggcccacg gcttgacccc ggagcaggtg  1140
gtggccatcg ccagcaatat tggtggcaag caggcgctgg agacggtgca ggcgctgttg  1200
ccggtgctgt gccaggccca cggcttgacc cccagcagg tggtggccat cgccagcaat  1260
aatggtggca agcaggcgct ggagacggtc agcggctgt tgccggtgct gtgccaggcc  1320
cacggcttga ccccggagca ggtggtggcc atcgccagcc acgatggcgg caagcaggcg  1380
ctggagacgg tccagcggct gttgccggtg ctgtgccagg cccacggctt gaccccggag  1440
caggtggtgg ccatcgccag caatattggt ggcaagcagg cgctggagac ggtgcaggcg  1500
ctgttgccgg tgctgtgcca ggcccacggc                                  1530
```

<210> SEQ ID NO 55
<211> LENGTH: 34
<212> TYPE: PRT
<213> ORGANISM: Artificial
<220> FEATURE:
<223> OTHER INFORMATION: TAL effector tandem repeat unit [XX is selected from the group consisting of HD, NG, NI, NN, NS, N*, HG, H*, IG, HA, ND, NK, HI, HN, NA, SN and YG (the symbol * denotes that the second X is missing)]
<220> FEATURE:
<221> NAME/KEY: MISC_FEATURE
<222> LOCATION: (12)..(13)
<223> OTHER INFORMATION: XX is the RVD of the TAL effector tandem repeat unit; XX is selected from the group consisting of HD, NG, NI, NN, NS, N*, HG, H*, IG, HA, ND, NK, HI, HN, NA, SN and YG (the symbol * denotes that the second X is missing)

<400> SEQUENCE: 55

Leu Thr Pro Glu Gln Val Val Ala Ile Ala Ser Xaa Xaa Gly Gly Lys

```
1               5              10              15
Gln Ala Leu Glu Thr Val Gln Ala Leu Leu Pro Val Leu Cys Gln Ala
            20              25              30
His Gly

<210> SEQ ID NO 56
<211> LENGTH: 14
<212> TYPE: PRT
<213> ORGANISM: Artificial
<220> FEATURE:
<223> OTHER INFORMATION: (non-specific) C-terminal truncated unit of 14
      amino acids of the TALEN arm that binds to the DNA target site of
      SEQ ID NO: 10

<400> SEQUENCE: 56

Leu Thr Pro Gln Gln Val Val Ala Ile Ala Ser Asn Gly Gly
1               5              10
```

The invention claimed is:

1. A method for contracting a DNA tandem repeat expansion, comprising:
   A) providing a diploid eukaryotic cell comprising a chromosomal nucleic acid comprising a CAG/CTG DNA tandem repeat expansion comprising 30 triplets in its genome;
   B) contacting the DNA tandem repeat expansion with a TALE-Nuclease comprising a first and a second DNA-binding polypeptide that targets a CAG/CTG repeat sequence within the DNA tandem repeat expansion,
   to thereby form a cell in which the first and second DNA-binding polypeptides have induced the contraction of the CAG/CTG DNA tandem repeat expansion on both strands of the DNA such that the CAG/CTG DNA tandem repeat expansion is contracted to 3-13 triplet repeats.

2. The method of claim 1, wherein the diploid eukaryotic cell is the cell of a subject having or at risk of developing a disorder mediated by the presence of the DNA tandem repeat expansion in the nucleic acid of the genome of the subject.

3. The method of claim 2, wherein the DNA tandem repeat expansion of the subject is contacted in vitro.

4. The method of claim 2, wherein the DNA tandem repeat expansion of the subject is contacted in vivo.

5. The method of claim 1, wherein the TALE-Nuclease comprises at least one sequence selected from the group consisting of SEQ ID NOS: 25, 26, 46 and 55, and at least one of the sequences of TAL effector tandem repeat units of the DNA-binding polypeptide which is coded by the plasmid deposited at the Collection Nationale de Culture de Microorganismes (C.N.C.M.), Paris, France, under deposit number 1-4804 or under deposit number 1-4805.

6. The method of claim 1, wherein the DNA target site of the first DNA-binding polypeptide is the sequence of SEQ ID NO: 10 or 11, and/or wherein the DNA target site of the second DNA-binding polypeptide is the sequence of SEQ ID NO: 4 or 5.

7. The method of claim 1, wherein the first and second DNA-binding polypeptides are the polypeptides coded by the sequences of SEQ ID NOS: 1 and 2, respectively.

8. The method of claim 1, comprising introducing a first expression vector encoding the first DNA-binding polypeptide into the cell, introducing a second expression vector encoding the second DNA-binding polypeptide into the cell, and expressing the first and second DNA-binding polypeptides in the cell to thereby contact the DNA tandem repeat expansion with the first DNA-binding polypeptide and the second DNA-binding polypeptide.

9. The method of claim 1, comprising transforming the cell with a first lentiviral vector pseudotyped particle that directs expression of the first DNA-binding polypeptide, transforming the cell with a second lentiviral vector pseudotyped particle that directs expression of the second DNA-binding polypeptide, and expressing the first and second DNA-binding polypeptides in the cell to thereby contact the DNA tandem repeat expansion with the first DNA-binding polypeptide and the second DNA-binding polypeptide.

10. The method of claim 1, wherein the overall mutation rate in the diploid eukaryotic cell is not increased.

11. The method of claim 1, wherein the CAG/CTG DNA tandem repeat expansion comprises 40 triplets.

12. The method of claim 1, wherein the CAG/CTG DNA tandem repeat expansion comprises 52 triplets.

13. The method of claim 1, wherein the CAG/CTG DNA tandem repeat expansion comprises 100 triplets.

14. The method of claim 1, wherein the CAG/CTG DNA tandem repeat expansion comprises a hairpin, a triple helix, or a tetraplex secondary structure.

15. The method of claim 1, wherein the CAG/CTG DNA tandem repeat expansion is in the human DMPK gene.

16. The method of claim 1, wherein the sequence of each of the DNA target sites are independently selected from the group consisting of:
   i. a fragment of a strand of double-stranded DNA nucleic acid consisting of a portion of a DNA tandem repeat, wherein the fragment comprises more than one copy of a DNA sequence unit of the DNA tandem repeat expansion; and
   ii. a fragment of a strand of double-stranded DNA nucleic acid, which starts outside the sequence of the DNA tandem repeat expansion and ends within the sequence of the at least ono DNA tandem repeat expansion, or conversely, which starts within the sequence of the DNA tandem repeat expansion and ends outside the sequence of the DNA tandem repeat expansion.

* * * * *

UNITED STATES PATENT AND TRADEMARK OFFICE
CERTIFICATE OF CORRECTION

PATENT NO. : 11,384,346 B2
APPLICATION NO. : 16/003789
DATED : July 12, 2022
INVENTOR(S) : Guy-Franck Richard et al.

Page 1 of 1

It is certified that error appears in the above-identified patent and that said Letters Patent is hereby corrected as shown below:

In the Claims

Column 134:
Line 61, Claim 16, delete "at least ono".

Signed and Sealed this
Eleventh Day of October, 2022

Katherine Kelly Vidal
*Director of the United States Patent and Trademark Office*